United States Patent
Doyle et al.

(10) Patent No.: US 6,600,083 B2
(45) Date of Patent: Jul. 29, 2003

(54) PARA-XYLENE PRODUCTION PROCESS INTEGRATING PRESSURE SWING ADSORPTION AND CRYSTALLIZATION

(75) Inventors: Ruth Ann Doyle, Oswego, IL (US); Jeffrey T. Miller, Naperville, IL (US); Richard A. Wilsak, Naperville, IL (US); Scott A. Roberts, Naperville, IL (US); Giorgio Zoia, Chicago, IL (US)

(73) Assignee: BP Corporation North America Inc., Warrenville, IL (US)

( * ) Notice: Subject to any disclaimer, the term of this patent is extended or adjusted under 35 U.S.C. 154(b) by 0 days.

(21) Appl. No.: 09/901,735

(22) Filed: Jul. 10, 2001

(65) Prior Publication Data

US 2002/0107427 A1 Aug. 8, 2002

Related U.S. Application Data

(60) Provisional application No. 60/220,536, filed on Jul. 10, 2000, provisional application No. 60/238,217, filed on Oct. 5, 2000, and provisional application No. 60/289,313, filed on May 8, 2001.

(51) Int. Cl.[7] .............................. C07C 7/14; C07C 7/12
(52) U.S. Cl. .................. 585/828; 585/812; 585/813; 585/814; 585/815; 585/820; 585/825; 585/847
(58) Field of Search ................ 585/812, 813, 585/814, 815, 847, 820, 825, 828

(56) References Cited

U.S. PATENT DOCUMENTS

| | | | |
|---|---|---|---|
| 2,985,694 A | 5/1961 | Talbot et al. | 260/674 |
| 3,177,265 A | 4/1965 | Lammers | 260/674 |
| 3,467,724 A | 9/1969 | Laurich | 260/674 |
| 3,653,184 A | 4/1972 | Drinkard | 55/67 |
| 3,656,278 A | 4/1972 | Drinkard et al. | 55/67 |
| 3,662,013 A | 5/1972 | Machell et al. | 260/674 |
| 3,699,182 A | 10/1972 | Cattanach | 260/674 |

(List continued on next page.)

FOREIGN PATENT DOCUMENTS

| | | |
|---|---|---|
| CN | 1136549 | 11/1996 |
| EP | 138617 | 4/1985 |
| EP | 923512 | 6/1999 |
| FR | 2757507 | 12/1996 |
| GB | 1420796 | 1/1976 |

OTHER PUBLICATIONS

Namba, S., et al., "Novel purification method of commercial o- and m-xylenes by shape selective adsorption on HZSM-5", Microporous Materials, 8, 39 (1997).

Yan, T. Y., "Separation of p-Xylene and Ethylbenzene from C8 Aromatics Using Medium-Pore Zeolites", Ind. Eng. Chem. Res.., 28,: 572–576 (1989).

Choudhary, V. R., et al., "Single-Component Sorption/Diffusion of Cyclic Compounds from Their Bulk Liquid Phase in H-ZSM-5 Zeolite", Ind. Eng. Chem. Res., 36,: 1812–1818 (1997).

Wu, E. L., "Hydrocarbon Adsorption Characterization of Some High Silica Zeolite", Stud Surf. Sci. Catal. 28, 547 (1996).

Primary Examiner—Walter D. Grffin
Assistant Examiner—Tam M. Nguyen
(74) Attorney, Agent, or Firm—Mary Jo Kennedy; Thomas A. Yassen

(57) ABSTRACT

A pressure swing adsorption process to separate para-xylene and ethylbenzene from $C_8$ aromatics which uses a para-selective, non-acidic, medium pore molecular sieve of the MFI structure type and is operated isothermally in the vapor phase at elevated temperatures and pressures is integrated with crystallization to produce para-xylene product. A fixed bed of adsorbent is saturated with pX and EB, which are preferentially adsorbed, the feed is stopped, and lowering the partial pressure desorbs the pX and EB. The process effluent, which is rich in pX and EB, is crystallized to obtain para-xylene product.

64 Claims, 14 Drawing Sheets

U.S. PATENT DOCUMENTS

| | | | |
|---|---|---|---|
| 3,724,170 A | 4/1973 | Allen et al. | 55/67 |
| 3,729,523 A | 4/1973 | Grandio, Jr. et al. | 260/674 |
| 3,770,841 A | 11/1973 | Meyers, Jr. | 260/668 |
| 3,856,873 A | 12/1974 | Burress | 260/668 |
| 3,916,018 A | 10/1975 | Edison et al. | 260/674 |
| 3,960,520 A | 6/1976 | Allen | 55/59 |
| 4,098,836 A | 7/1978 | Dywer | 260/668 |
| 4,163,028 A | 7/1979 | Tabak et al. | 585/481 |
| 4,453,029 A | 6/1984 | Dessau | 585/828 |
| RE31,782 E | 12/1984 | Olson et al. | 585/481 |
| 4,899,011 A | 2/1990 | Chu et al. | 585/481 |
| 4,899,017 A | 2/1990 | Yan | 585/828 |
| 4,908,342 A | 3/1990 | McWilliams et al. | 502/68 |
| 5,001,296 A | 3/1991 | Howley et al. | 585/489 |
| 5,028,573 A | 7/1991 | Brown et al. | 502/66 |
| 5,284,992 A | 2/1994 | Hotier et al. | 585/805 |
| 5,329,060 A | 7/1994 | Swift | 585/805 |
| 5,329,061 A | 7/1994 | Swift | 585/805 |
| 5,367,099 A | 11/1994 | Beck et al. | 585/475 |
| 5,448,005 A | 9/1995 | Eccli et al. | 585/812 |
| 5,705,726 A | 1/1998 | Abichandani et al. | 585/481 |
| 5,908,967 A | 6/1999 | Benazzi et al. | 585/481 |
| 5,922,924 A | 7/1999 | Hotier et al. | 585/479 |
| 5,948,950 A | 9/1999 | Hotier et al. | 585/828 |
| 6,111,161 A | 8/2000 | MacPherson et al. | 585/812 |
| 6,147,272 A | 11/2000 | Mikitenko et al. | 585/812 |
| 6,150,292 A | 11/2000 | Merlen et al. | 502/66 |

PARA-XYLENE PRODUCTION PROCESS INTEGRATING PRESSURE SWING ADSORPTION AND CRYSTALLIZATION

This application claims the benefit of U.S. Provisional Application No. 60/220,536 filed Jul. 10, 2000, U.S. Provisional Application No. 60/238,217 filed Oct. 5, 2000, and U.S. Provisional Application No. 60/289,313 filed May 8, 2001, all of which are incorporated herein by reference in their entireties.

BACKGROUND OF THE INVENTION

The present invention relates to a process for producing para-xylene integrating pressure swing adsorption for separating para-xylene and ethylbenzene from mixed $C_8$ aromatics with recovery of para-xylene by crystallization. The present invention further relates to a process comprising using a pressure swing adsorption (PSA) process for separating para-xylene and ethylbenzene from mixed $C_8$ aromatics using a para-selective adsorbent and separating the para-xylene from the para-xylene/ethylbenzene effluent by fractional crystallization to obtain para-xylene product. The para-selective adsorbent is preferably a non-acidic, molecular sieve. The para-selective adsorbent is more preferably a non-acidic, medium pore, molecular sieve. The molecular sieve is preferably of the MFI structure type and the process is preferably operated in the vapor phase at elevated temperatures and pressures wherein the temperature is substantially isothermal. The present invention also relates to a method of pressure swing adsorption which includes a plurality of steps and which provides recovery from a mixture comprising $C_8$ aromatics of a substantially pure para-xylene or para-xylene and ethylbenzene product stream and a substantially pure meta-xylene and ortho-xylene product stream and separating the para-xylene from the para-xylene/ethylbenzene stream by fractional crystallization to obtain a substantially pure para-xylene product.

A pressure swing adsorption process to separate para-xylene and ethylbenzene from $C_8$ aromatics which uses a para-selective, non-acidic, medium pore molecular sieve of the MFI structure type and is operated isothermally in the vapor phase at elevated temperatures and pressures is used to produce a para-xylene-rich stream which is then subjected to crystallization to produce a para-xylene product. In the pressure swing adsorption step, a fixed bed of adsorbent is saturated with pX and EB, which are preferentially adsorbed, then the feed to the process is stopped. Lowering the partial pressure desorbs the pX and EB. The process effluent is rich in pX and EB. A stream of non-adsorbed mX and oX may be obtained prior to desorption of pX and EB. The mX/oX stream may be isomerized to produce an equilibrium mixture of xylenes and recycled to the PSA step.

It is known that certain high surface area, porous substances such as silica gel, activated charcoal, and molecular sieves, including zeolites and other molecular sieves, have certain selective adsorption characteristics useful in separating a hydrocarbon mixture into its component parts.

The selective sorption properties of molecular sieves and zeolites have been disclosed in earlier patents and in literature references. Crystalline molecular sieves and zeolites are shape-selective in that they will admit molecules of specific geometry while excluding other molecules.

The separation of xylene isomers has been of particular interest because of the usefulness of para-xylene in the manufacture of terephthalic acid which is used in the manufacture of polyester fabric. Other components of the $C_8$ aromatic hydrocarbon feedstream from which para-xylene (pX) is generally produced are ortho-xylene (oX), which is used in the manufacture of phthalic anhydride which is used to make phthalate based plasticizers; meta-xylene (mX), which is used in the manufacture of isophthalic acid used in the production of specialty polyester fibers, paints, and resins; and ethylbenzene (EB) which is used in the manufacture of styrene.

A refinery feedstock of aromatic $C_8$ mixtures containing ethylbenzene and xylenes will typically have the following content:

| | |
|---|---|
| ethylbenzene | about 0 wt % to about 50 wt % |
| para-xylene | about 0 wt % to about 25 wt % |
| ortho-xylene | about 0 wt % to about 35 wt % |
| meta-xylene | about 20 wt % to about 90 wt % |
| non-aromatics | about 0 wt % to about 10 wt % |
| $C_9^+$ aromatics | about 0 wt % to about 30 wt % |

Equilibrium mixtures of $C_8$ aromatic hydrocarbons generally contain about 22 weight percent para-xylene, about 21 weight percent ortho-xylene, and about 48 weight percent meta-xylene in the equilibrium mixture.

Processes to separate xylene isomers include low temperature crystallization, fractional distillation, selective sulfonation with subsequent hydrolysis and selective solvent separation; however, such processes require high operating costs.

The use of faujasite zeolites, which are large pore type X and Y type zeolites, as adsorbents in liquid phase, chromatographic-type separations is well known.

In the petrochemical production chain, one of the most important streams is the $C_6$ to $C_8$ aromatics stream containing benzene, toluene, and xylenes (BTX), which is a source of raw materials for high value downstream products. Of the $C_8$ aromatics, para-xylene (pX) is the most desirable. However, because the boiling points of ethylbenzene (EB), ortho-xylene (oX), meta-xylene (mX) and para-xylene (collectively referred to as "$C_8$ aromatics") are close, they are difficult to separate by fractional distillation. As a consequence, various alternative methods of separating pX from the $C_8$ aromatics have been developed. Common separation methods are fractional crystallization, which utilizes the difference in freezing points, and liquid phase adsorption (e.g., UOP's Parex process and IFP's Eluxyl process), which uses a faujasite zeolite to chromatographically separate pX from the other $C_8$ aromatics. The reject stream from the crystallization process or the raffinate from the adsorption process are depleted in pX, and contain relatively high proportions of EB, oX and mX. These streams are typically sent to a catalyst reactor, where the xylenes are isomerized to equilibrium, and at least a portion of the EB is converted to other products, which can be removed from the $C_8$ aromatics by fractional distillation.

Processes for making pX have typically included combinations of isomerization with fractional crystallization or adsorption separation. FIG. 1 is a schematic representation of known art combination of an isomerization catalyst reactor and a crystallization unit. Crystallization is a separation process that takes advantage of the fact that pX crystallizes before the other isomers, i.e., pX crystallizes at 13.3° C. (55.9° F.), whereas oX crystallizes at −25.2° C. (13.4° F.) and mX at −47.9° C. (−54.2° F.). In the physical system of the three isomers, there are two binary eutectics of importance, the pX/mX and the pX/oX. As pX is crystallized from the mixture, the remaining mixture (mother liquor) composition approaches one of these eutectic binaries, depending on the starting composition of the mixture. Therefore, in commercial practice, pX is crystallized so that the binary eutectic is only approached but not reached to avoid co-crystallization of the xylene isomers, which would lower the pX purity. Thus, the key disadvantage for crystallization is restricted pX recovery per pass, due to this eutectic limit of the $C_8$ stream. Typically, the concentration of pX in a mixed $C_8$ aromatic stream at equilibrium is about 22 wt %. In commercial crystallization operations, the eutectic point of this mixture limits the pX removed per pass to about 65% of that amount.

The problem of the eutectic limit for pX crystallization has been recognized for some time. U.S. Pat. No. 5,329,060 discloses that the eutectic point of the crystallization unit can be overcome by use of a selective adsorption zone that enriches the pX feed to the crystallizer by rejecting most of the mX, oX and EB to the isomerization reactor. Specifically, the disclosure teaches using a faujasite-based, liquid phase adsorption process that can either be selective for pX or selective for mX and oX. The result of this process is a stream enriched in pX, but still containing a substantial portion of mX and oX. Similarly, U.S. Pat. No. 5,922,924 discloses combining at least one liquid phase, simulated moving bed adsorption zone with crystallization to produce high purity pX. Again, pX is enriched, but the stream still contains significant mX and oX.

U.S. Pat. No. 3,699,182 discloses use of zeolite ZSM-5 in a process for selective separation of biphenyls from mixtures containing the same and para-disubstituted aromatic isomers from mixtures containing the same, particularly for separating $C_8$ aromatics using ZSM-5 zeolite.

U.S. Pat. No. 3,724,170 discloses chromatographic separation of C8 aromatic mixtures over zeolite ZSM-5 or ZSM-8, which has preferably been reacted with an organic radical-substituted silane, in at least two distinct stages whereby para-xylene and ethylbenzene are selectively absorbed whereas the meta-xylene and ortho-xylene are not adsorbed, removing the unadsorbed meta-xylene and ortho-xylene, eluting the para-xylene followed by the ethylbenzene.

British Pat. No. 1,420,796 discloses use of zeolite ZSM-5 or ZSM-8, preferably ZSM-5 or ZSM-8 zeolites which have been reacted with certain silanes, for adsorptive separation of para-xylene and ethylbenzene from a mixture of para-xylene, ortho-xylene, meta-xylene, and ethylbenzene by adsorption/desorption using two or more columns operated in a parallel manner so that when adsorption is being conducted in one column, desorption can be conducted in a parallel column under such conditions as to obtain a continuously operating process which is said to have faster results than use of a single column alone. It is stated that 250° C. (482° F.) is a preferred upper limit as operation above 250° C. (482° F.) may lead to catalytic conversion in the zeolite-containing column.

U.S. Pat. No. 3,729,523 discloses a process for separating and recovering each of the xylene isomers and ethylbenzene wherein a mixture of $C_8$ aromatic hydrocarbons, which may also contain $C_9$ and higher paraffins, is heated to 50°–500° F. (10°–260° C.) and subjected to an adsorption step to recover a first mixture of para-xylene and ethylbenzene and a second mixture comprising meta-xylene, ortho-xylene, and the $C_9$ and higher aromatics. The adsorption is preferably conducted in the presence of a molecular sieve or synthetic crystalline aluminosilicate zeolite as the adsorbent, with ZSM-5, the preferred zeolite. The para-xylene and ethylbenzene are adsorbed and may be recovered by heating the adsorbent, reducing the partial pressure of the sorbed material in the vapor or liquid surrounding the adsorbent, lowering the total pressure of the system or purging with a suitable inert gas or displacement liquid. The resulting para-xylene and ethylbenzene mixture is then subjected to crystallization to recover para-xylene and the mother liquor is subjected to distillation to recover the ethylbenzene.

Chinese Patent Application No. 1136549 discloses selectively adsorbing pX and EB from a $C_8$ isomer stream using silicalite-1 zeolite and then producing >99.5% purity mX and oX from the portion of the stream not adsorbed. In this process there is a substantial amount of contaminating feedstream in the voids of the silicalite-1 adsorbent which is not removed and comes off the adsorption bed along with the adsorbed pX and EB so that the desorbed stream is not substantially pure pX and EB but contains significant amounts of unseparated oX and mX.

U.S. Pat. No. 6,111,161 discloses a process for the production of high purity para-xylene from a charge containing $C_{7-9}$ aromatic hydrocarbons in which a first fraction is enriched to at least 30% weight with para-xylene and this fraction is purified by at least one high-temperature crystallization in at least one crystallization zone. Said first fraction is crystallized in a crystallization zone at high temperature T1 and advantageously between +10 and –25° C., crystals in suspension in a mother liquor are recovered, the crystals are separated from the mother liquor in at least a first separation zone, the crystals obtained are partially melted in at least a zone for partial melting and a suspension of crystals is recovered, the crystals in suspension are separated and washed in at least one separation and washing zone and pure para-xylene crystals and washing liquor are recovered, and pure crystals are optionally completely melted and a liquid stream of melted para-xylene is collected.

U.S. Pat. No. 5,448,005 discloses a process for producing high purity para-xylene from a high weight percent para-xylene feedstock, comprising at least about 70 wt % para-xylene and preferably at least about 80 wt % para-xylene which uses a single temperature crystallization production stage at a temperature in the range of from about 0° F. to about 50° F. and also uses scavenger stages to raise the para-xylene recovery rate. The single temperature production stage crystallizer of the process employs a wash using only para-xylene product.

It is generally recognized by those skilled in the art that using crystallization for separating and purifying pX from a mixture of $C_8$ aromatics suffers from the major disadvantage that the maximum recovery level per pass is limited to approximately 60–65% due to the existence of eutectics between pX and the other $C_8$ aromatic hydrocarbons, and that it is desirable to increase the para-xylene content of the stream going to the crystallizer above that typical of mixed xylenes (i.e., 22–24%).

For example, U.S. Pat. No. 5,284,992 describes increasing the para-xylene content of the stream going to the crystallizer by first separating the $C_8$ aromatic stream via simulated moving bed adsorption chromatography, which produces a stream containing 75–98% pX and a second stream containing a mixture of mX, oX and ethylbenzene.

U.S. Pat. No. 5,329,060 teaches combining crystallization with a similar chromatographic separation using Faujasite aluminosilicates or the closely related type X and type Y aluminosilicates, which are non para-selective molecular sieves.

U.S. Pat. No. 3,729,523 discloses a process for recovering high purity streams of all the $C_8$ aromatic xylene isomers including ethylbenzene by combining selective adsorption and crystallization.

Continuous liquid chromatography methods of separation (e.g., simulated countercurrent like UOP's PAREX) are complex and use a solvent (i.e., liquid desorbent) to remove the adsorbed phase. This results in the necessity of an additional column for separating by fractional distillation the desorbent for reuse. Fixed bed temperature (thermal) swing adsorption/desorption is limited by the long times (hours to days) necessary to increase or decrease the temperature of the adsorbent bed.

None of the prior art describes a pressure swing adsorption process for separating pX from a $C_8$ aromatic mixture. Pressure swing adsorption offers the advantage of reduced complexity, no liquid desorbent and opportunities for better synergy with the rest of the para-xylene unit (energy savings), e.g., directing the non-adsorbed phase (mX and oX) exiting the adsorption unit at high temperature directly to the xylene isomerization reactor.

None of these references discloses a process using pressure swing adsorption employing a para-selective adsorbent which is preferably a large crystal, non-acidic medium pore molecular sieve in combination with fractional crystallization and, optionally, isomerization, to obtain high purity para-xylene in high yield.

Molecular sieves are crystalline oxides having pore openings and internal cavities the size of some molecules. Zeolites, a sub-group of molecular sieves, are crystalline aluminosilicates. Another well known sub-group of molecular sieves are aluminophosphates or ALPOs. In general, molecular sieves are classified into three groups based on pore size: small pore molecular sieves with pore diameters from 3–4 Å; medium pore molecular sieves with pores diameters from 4–6 Å; and large pore molecular sieves with pore openings of 6–8 Å. In addition to the molecular size pores, molecular sieves have high adsorption energies and for many years have been used as adsorbents. By selection of the proper pore size, molecular sieves may selectively adsorb molecules of different size. This molecular sieving leads to adsorption and separation of the smaller molecule. Often molecular sieving selectivities are high, 100 or greater. The separation of branched from linear paraffins is a commercial process, which utilizes the small pore A zeolite.

Large pore molecular sieves have also been utilized in the separation of hydrocarbons. In large pore molecular sieves, however, all components diffuse into the pores and the separation is based on differences in adsorption energies. The molecule with the highest bond energy is preferentially adsorbed. Generally, adsorption selectivities are high only when molecules have very different heats of adsorption, for example water and paraffin. For molecules with similar heats of adsorption, the adsorption selectivities are low, ca. 1–4. Xylenes isomers, for example, have similar heats of adsorption in Y zeolite. Due to small differences in heats of adsorption and packing geometry in BaY, pX displays an adsorption selectivity of about 2 compared with the other $C_8$ aromatics. In order to separate pX in sufficient purity for chemical sale, i.e., greater than 99%, many separation stages must be conducted. This type of process operates on principles similar to that of chromatography. Commercial examples of separations of this type are the UOP Parex and IFP Eluxyl liquid phase adsorption processes, which utilize ion exchanged Y zeolites to separate pX from $C_8$ aromatics.

Adsorbents useful in the present invention are based on molecular sieves that selectively adsorb p-xylene within the channels and pores of the molecular sieve while not effectively adsorbing m-xylene and o-xylene $C_8$ isomers (i.e., total exclusion of the larger m-xylene and o-xylene or having much slower adsorption rates compared to p-xylene.).

Molecular sieves are ordered porous crystalline materials, typically formed from silica, alumina, and phosphorus oxide ($PO_4$) tetrahedra, that contain a crystalline structure with cavities interconnected by channels. The cavities and channels within the crystalline structure are uniform in size and may permit selective separation of hydrocarbons based upon molecular dimensions. Generally, the term "molecular sieve" includes a wide variety of natural and synthetic crystalline porous materials which typically are based on silica tetrahedra in combination with other tetrahedral oxide materials such as aluminum, boron, titanium, iron, gallium, and the like. In these structures networks of silicon and elements such as aluminum are cross-linked through sharing of oxygen atoms. Substitution of elements such as aluminum or boron for silicon in the molecular sieve structure produces a negative framework charge which must be balanced with positive ions such as alkali metal, alkaline earth metal, ammonium or hydrogen. Molecular sieve structures also may be formed based on phosphates in combination with other tetrahedrally substituted elements such as aluminum.

Adsorbents useful in this invention should not possess catalytic isomerization or conversion activity with respect to the $C_8$ aromatic feedstream. Thus, suitable molecular sieves should be non-acidic. If an element such as aluminum or gallium is substituted in the molecular sieve framework, the sieve should be exchanged with a non-acidic counter-ion, such as sodium, to create a non-acidic sieve adsorbent.

Examples of molecular sieves suitable as adsorbents useful in this invention include zeolitic materials containing pore dimensions in the range of 5 to 6 Å ($10^{-8}$ meter), typically 5.1 to 5.7 Å, and preferably 5.3 to 5.6 Å, as measured in cross axes of the pore. This range typically is referred to as "medium pore" and typically contains 10-ring tetrahedra structures. Typical examples of medium pore molecular sieves include those with MFI and MEL framework structures as classified in Meier and Olson, "Atlas of Zeolite Structure Types," International Zeolite Association (1987), incorporated herein by reference in its entirety. A small pore molecular sieve, such as A zeolite, which contains 8-ring structures does not have a sufficiently large pore opening to effectively adsorb para-xylene within the sieve. Most large pore molecular sieves, such as mordenite, Beta, LTL, or Y zeolite, that contain 12-ring structures do not adsorb para-xylene selectively with respect to ortho- and meta-xylenes. However, several 12 ring structures, having a smaller effective pore size, for example due to puckering, are potentially useful in the invention, such as structure types MTW (e.g., ZSM-12) and ATO (e.g., ALPO-31).

Specific examples of molecular sieves include ZSM-5 (MFI structure type) and ZSM-11 (MEL structure type) and related isotypic structures. Since suitable adsorbents should not be catalytically reactive to components in the feedstream, the preferable adsorbent useful in this invention is silicalite (MFI structure type), an essentially all silica molecular sieve, which contains minimal amounts of aluminum or other substituted elements. Typically, the silica/alumina ratio of suitable silicalite is above 200 and may range above 1000 depending on the contaminant level of aluminum used in the sieve's preparation. Other MFI and MEL sieves may be use to the extent they are made non-catalytically active. MFI-based molecular sieves are preferred in this invention with silicalite as the most preferred. Other potentially useful adsorbents include structure types MTU, FER EUO, MFS, TON, AEL, ATO, NES, and others with similar pore sizes.

A molecular sieve which is not catalytically reactive will typically exhibit less than 10% conversion of pX to mX and oX, and preferably less than 5%, and most preferably less than 1%, at the temperature of operation for the process of the invention.

Attempts have been made to use adsorption with zeolites such as ZSM-5 and ZSM-8 to separate ethylbenzene (EB), para-xylene (pX), meta-xylene (mX), and ortho-xylene (oX) from mixtures of $C_8$ aromatics; however, a major disadvantage of these processes is that the time required to effect desorption of the adsorbed components is too long to provide a commercially useful process. In addition, with acidic zeolites, such as HZSM-5, the high temperatures used to obtain rapid desorption cause catalytic reactions to occur converting pX to mX and oX and converting EB to benzene. Furthermore, with HZSM-5, traces of olefins, which are usually present in commercial feeds, irreversibly chemisorb lowering the adsorption capacity of the zeolite. As a result, frequent reconditioning of the adsorbent (e.g., removal of coke deposits) is required.

Due to the strong adsorption and reactivity of xylenes on acid sites of adsorbents such as HZSM-5, a commercial separation process has not been developed. We describe the use of silicalite in a high temperature process to effect the separation of para-xylene and ethylbenzene from a $C_8$ aromatic mixture without reaction of the adsorbed hydrocarbons. These adsorbent and process modifications solve the previous technical obstacles, which have limited commercial development of a molecular sieving, selective adsorption/desorption process for separation of $C_8$ aromatic hydrocarbons.

The process of the present invention overcomes disadvantages of known processes by using pressure swing adsorption at elevated temperature and pressure with a non-acidic, molecular sieve-containing adsorbent to accomplish a rapid adsorption and desorption of the desired components from a feedstream containing $C_8$ aromatics and provide a rapid separation of the desired components which is suitable for commercial use. A non-acidic molecular sieve, such as silicalite (MFI structure type with little to no aluminum), is used to selectively adsorb pX and EB. Desorption is significantly faster and reactions of the adsorbed molecules (pX and EB) do not occur. In addition, olefins do not adsorb on the silicalite, so the adsorption capacity of the adsorbent remains high and frequent reconditioning is not required.

The effluent stream of pX and EB obtained following pressure swing adsorption is has a higher concentration of pX than is typically obtained with isomerization, and, in optimum conditions, may be substantially free of mX and oX. When separation of $C_8$ aromatics by pressure swing adsorption is combined with crystallization, this has the advantage of enabling one to increase pX production capacity. Due to the higher concentrations of pX obtained with PSA, it will also be possible to reduce costs of purifying pX by conducting the crystallization of the para-xylene-containing product stream at higher temperatures, if desired. This would reduce energy consumption and may eliminate the need for extremely low-temperature ethylene-cooled crystallization facilities which would be a further cost savings.

The disclosed invention provides a novel and improved process for producing para-xylene employing a pressure swing adsorption unit containing an adsorbent selective for para-xylene and ethylbenzene in conjunction with crystallization technology for separating and recovering para-xylene to improve the overall yield and per pass recovery of para-xylene. The process of the present invention will allow the capacity of existing crystallization units to be increased at minimal capital investment and will also benefit new units, by reducing capital and utility and raw material costs.

Two commercial processes are practiced for separating para-xylene (pX) from the other $C_8$ aromatic isomers, fractional crystallization and liquid phase adsorption. The advantage of crystallization is high product purity; however, the key disadvantage is restricted pX recovery per pass, due to the eutectic limit of the $C_8$ stream. Typically, the concentration of pX in a mixed $C_8$ aromatic stream at equilibrium is about 22 wt %. In commercial crystallization operations, the eutectic point of this mixture limits the pX removed per pass to about 65%. The process of the present invention increases the efficiency of the crystallizer for removing pX by first passing the mixed $C_8$ aromatic stream through a pressure swing adsorption (PSA) unit to remove a significant portion of the meta-xylene (mX) and ortho-xylene (oX) in the stream. This increases the pX concentration in the crystallizer feed and lowers the temperature at which pX can be crystallized without co-crystallizing impurities, resulting in significantly more pX removed per pass. Furthermore, the pX-depleted stream gives lower xylene loss when isomerized in an isomerization reactor, which increases the overall yield of pX for the unit. Recovery of pX can be further enhanced by pretreatment of the feed to the PSA unit and/or to the isomerization reactor to reduce the concentration of EB in the feed. This can be accomplished by contacting the feed with an ethylbenzene conversion catalyst.

An additional catalyst reactor may be used to pretreat the $C_8$ aromatic feed to convert at least a portion of the ethylbenzene to xylenes or products which can be separated by fractional distillation from the $C_8$ aromatics prior to sending the $C_8$ aromatic feedstream to the PSA unit.

In one embodiment of the invention, an additional catalyst reactor may be used to treat the para-xylene-lean reject stream from the separation by crystallization of pX from the pX/EB stream from the PSA unit to convert at least a portion of the ethylbenzene in it to xylenes or products which can be separated by fractional distillation from the $C_8$ aromatics prior to sending the $C_8$ aromatic feedstream to the PSA unit.

The para-xylene production unit, in addition to a PSA unit (and, optionally, a separation/purification unit for separating pX from pX/EB) used in the process of the present invention may also contain a catalyst reactor for isomerization of aromatics and one or more distillation columns for separation of aromatics as well as a catalyst reactor for pretreatment of a $C_8$ aromatic feed to reduce the amount of ethylbenzene in the feed by ethylbenzene conversion.

The catalyst system in the additional catalyst reactor used to convert ethylbenzene can be any catalyst system suitable for ethylbenzene dealkylation, hydrodeethylation or hydroisomerization. Examples of catalyst systems for dealkylation are disclosed in Re. 31,782 and U.S. Pat. No. 4,908,342, incorporated herein by reference in their entireties. Examples of catalyst systems for hydrodeethylation are disclosed in U.S. Pat. No. 4,899,011 and U.S. Pat. No. 5,367,099 incorporated herein by reference in their entireties. Examples of catalyst systems for hydroisomerization are disclosed in U.S. Pat. Nos. 5,028,573, 6,150,292 and 5,908,967 incorporated herein by reference in their entireties.

Many of the chemical and physical properties of xylene isomers and ethylbenzene are very similar making separation difficult. The molecular size of these isomers, however, is slightly different and is determined by the position of methyl substitution. The kinetic diameter of para-xylene and ethylbenzene are approximately 6.0 Å; whereas meta-xylene and ortho-xylene are slightly larger, 6.8 Å. It has been known for many years that, based on these differences in size, medium pore zeolites, such as HZSM-5, can selectively adsorb para-xylene and ethylbenzene [See U.S. Pat. Nos. 3,653,184; 3,656,278; 3,770,841; 3,960,520; 4,453,029; 4,899,017; Wu, et al. STUD. SURF. SCI. CATAL., 28:547 (1996); Yan, T. Y., IND. ENG. CHEM. RES. 28:572(1989); and Choudhary, et al., IND. ENG. CHEM. RES. 36:1812 (1997)] However, a disadvantage of using HZSM-5 for such separations is that protonation of the aromatic ring by acid sites in ZSM-5 leads to formation of a strong chemical bond [Farneth, et al., LANGMUIR, 4:152(1988)] resulting in low desorption rates and long desorption times at low temperature. As a result, such excessively large amounts of ZSM-5 would be required for commercial scale separation of para-xylene and ethylbenzene under these conditions that such separations are not commercially feasible. Increasing the desorption temperature does increase the desorption rate, which lowers the amount of adsorbent needed; however, the acid sites on the HZSM-5 zeolite also have catalytic properties which cause undesirable isomerization of para-xylene to meta-xylene and ortho-xylene, significantly reducing para-xylene purity. Another disadvantage is that the acid sites strongly adsorb olefins which are typically present along with the $C_8$ aromatics in the feedstream, thus lowering the capacity of the adsorbent to adsorb para-xylene and ethylbenzene. These olefins can only be desorbed at high temperatures. Thus, there is either a loss of adsorption capacity at low temperature or a loss in selectivity at high temperature due to reactions catalyzed by the acid sites.

Disadvantages of the earlier processes are overcome in the present invention by using a pressure swing adsorption process for separating para-xylene and ethylbenzene from mixed $C_8$ aromatics using a non-acidic, medium pore molecular sieve, preferably of the MFI structure type and preferably operating in the vapor phase at elevated temperatures and pressures followed by separation and purification of the para-xylene by crystallization. The present invention uses a pressure swing adsorption process which includes a plurality of steps and which provides recovery from a mixture comprising $C_8$ aromatics of a para-xylene or para-xylene and ethylbenzene product stream containing higher concentrations of para-xylene or para-xylene and ethylbenzene than are obtainable by the typical isomerization processes as well as a meta-xylene and ortho-xylene product stream having enhanced amounts of mX and oX. The para-xylene is then separated from the para-xylene/ethylbenzene stream by fractional crystallization to obtain a substantially pure para-xylene product. An advantage of the process is that the PSA unit does an initial bulk separation of pX/EB from mX/oX prior to product purification by crystallization. In the process of the invention, mX and oX no longer go to the crystallization unit but are sent back to the catalyst section. The composition of the pX/EB stream comprises at least 50 mole percent pX/EB. Thus, with the present invention, more pX is recovered per pass and more pX can be produced.

We have found that non-acidic forms of ZSM-5, such as Na-ZSM-5, are preferred adsorbents over HZSM-5. In particular, silicalite is a preferred adsorbent over HZSM-5. Silicalite, an all silica, isostructural form of ZSM-5 has been shown to possess superior properties. Like ZSM-5, silicalite selectively adsorbs pX and EB; however, desorption is significantly faster, since the molecules are only adsorbed physically not chemically, as with HZSM-5. Moreover, pX does not isomerize, even at the elevated temperatures necessary to make the process economically practicable.

In silicalite, a silica analog of H-ZSM-5, pX and EB are selectively adsorbed due to their smaller size. However, unlike H-ZSM-5, silicalite contains no acid sites. As a result, pX and EB are desorbed at high temperature without reaction. At elevated temperature, the desorption rates are high and the cycle times are much shorter. As a result, much less adsorbent is required. Furthermore, the adsorption capacity does not decrease significantly with repeated adsorption/desorption cycles due to adsorption of olefins in the aromatic stream.

The present invention uses selective adsorption (adsorption of the smaller $C_8$ isomers) and selective desorption (i.e., no isomerization upon desorption) at substantially isothermal temperatures to provide a substantially pure product stream of para-xylene and ethylbenzene and a substantially pure stream of ortho-xylene and meta-xylene. The components in these streams can be further separated to provide substantially pure para-xylene, ethylbenzene, ortho-xylene, and meta-xylene products.

The problems of long desorption times or the need for excessively large amounts of adsorbent have made earlier attempts to separate C8 aromatics by molecular sieving commercially impracticable. In addition to these disadvantages, there is also the problem of how to remove $C_8$ aromatic feed that collects in non-selective voids, that is, feed which collects in the non-selective void volume (i.e., large mesopores in the adsorbent, interstitial space between adsorbent particles, and void space in the adsorbent vessel) so that the purity of the desorbed product stream will not be reduced by this material. The art has not recognized how to overcome this problem for $C_8$ aromatics.

The present invention has solved this problem by selectively separating the $C_8$ aromatic feed that is contained in the non-selective void volume so that a high purity stream of para-xylene and ethylbenzene is obtained following desorption. A high purity stream of mX and oX is also obtained by the process of the invention. In one embodiment of the invention this high purity stream of mX/oX is obtained by separating the mX/oX from the non-selective void volume prior to desorbing the pX/EB.

The use of the process of the present invention in para-xylene production facilities would significantly reduce the amount of meta-xylene and ortho-xylene sent to a crystallization section, thus opening up capacity and decreasing operating costs. This would increase the para-xylene concentration and yields. Having a stream with a greater concentration of para-xylene going to the crystallization section may also make it possible to eliminate a crystallizer. For example, a low-temperature ethylene unit might not be needed if a feed with a higher concentration of para-xylene is being crystallized to recover para-xylene. This would also save equipment costs and reduce the amount of energy necessary to conduct the crystallization and purification of para-xylene.

We have determined that PSA does not need to produce product quality pX in order to provide an advantage over existing technology. Rather, the PSA unit offers substantial benefits when used to concentrate pX in existing or new plants using crystallization for pX recovery. The process of the invention described in this disclosure comprises a pressure swing adsorption unit, and a crystallization section, wherein, the efficiency of the crystallizer for removing pX is improved by first passing the mixed $C_8$ aromatic stream through a PSA unit to remove a portion of the mX and oX in the stream, such that the pX-rich stream contains at least 50 mole % pX and EB relative to the other C8 aromatics. This increases the pX concentration in the crystallizer feed and lowers the temperature at which pX can be crystallized without co-crystallizing impurities, resulting in significantly more pX removed per pass. Furthermore, the pX-depleted stream from the PSA unit, if recycled to an isomerizer, gives lower xylene loss in the isomerization reactor, which increases the overall yield of pX for the unit. The para-xylene production unit, in addition to a PSA unit and a crystallization section used in the process of the present invention may also contain a catalyst reactor for isomerization of aromatics and one or more distillation columns for separation of aromatics as well as a catalyst reactor for pretreatment of a $C_8$ aromatic feed to reduce the amount of ethylbenzene in the feed by ethylbenzene conversion.

The present invention is therefore directed to a chemical plant and process which offers an improvement over the prior art for the recovery of pX from streams which comprise $C_8$ aromatics. The present invention resides in the specific application of a pressure swing adsorption unit and process in conjunction with a fractional crystallization process. This invention utilizes a molecular sieve adsorbent which is selective for pX and EB, and rejects mX and oX to produce an effluent stream comprising pX/EB at a concentration of 50 mole % or greater(relative to the total C8 aromatics).

In a preferred embodiment of the invention, the crystallization process used in combination with PSA has an advantage over other crystallization processes. It reduces the refrigeration requirements compared to designs disclosed in U.S. Pat. Nos. 6,111,161 and 5,448,005. Thus it requires less energy expenditure and provides a cost savings. It accomplishes this by separating some or most of the final product early in the separation sequence thereby reducing the amount of material that requires lower temperature refrigeration. It does not recycle cake back to the first crystallizer from the lower temperature stage(s), but rather uses a reslurry drum to sufficiently warm the crystals so that additional para-xylene product can be recovered without the need for more refrigeration. As calculated according to standard engineering practices, the refrigeration compressor horsepower for the invention can be as much as 13% less than that for comparable designs based on the teachings of U.S. Pat. No. 6,111,161. Combining the advantages of this crystallization process, in which pX in a feed containing higher concentrations of pX can be separated at higher temperatures, without the need for additional processing, with the advantages obtained by using PSA for separation of pX or pX and EB from a $C_8$ aromatic feed increases the overall advantages of the process of the present invention over known para-xylene production processes.

SUMMARY OF THE INVENTION

The present invention relates to a process for producing high purity para-xylene from mixed $C_8$ aromatics comprising subjecting the $C_8$ aromatic feed to a pressure swing adsorption (PSA) process to separate para-xylene or para-xylene and ethylbenzene from a mixture containing $C_8$ aromatics and then subjecting the stream of para-xylene or para-xylene and ethylbenzene recovered to crystallization to obtain high purity para-xylene.

The present invention also relates to a process for the production of substantially pure para-xylene from a feedstream comprising $C_8$ aromatics which contains para-xylene, meta-xylene, ortho-xylene, and ethylbenzene, said process comprising introducing a feedstream comprising $C_8$ aromatics into a pressure swing adsorption unit to produce a stream comprising para-xylene or para-xylene and EB and having no more than a total of about 50 mole percent of meta-xylene and ortho-xylene based on total $C_8$ aromatics in which the pX concentration is greater than that found in an equilibrium mixture of xylene isomers and a stream enriched in mX and oX having no more than a total of about 25 mole percent of para-xylene based on total $C_8$ aromatics; and passing at least a portion of the para-xylene-enriched stream to a crystallization unit to produce a high purity para-xylene product stream and a para-xylene-lean stream.

A para-xylene-lean reject stream from the crystallization unit which comprises $C_8$ aromatics may be sent to a catalyst reactor, where the xylenes are isomerized to equilibrium and where at least a portion of any ethylbenzene in the stream is converted to products which can be separated by fractional distillation from the $C_8$ aromatics. The para-xylene-lean reject stream may be combined with the mX/oX-rich effluent stream from the PSA prior to sending it to the isomerization reactor. An additional catalyst reactor may be used to pretreat the $C_8$ aromatic feed to convert at least a portion of the ethylbenzene to xylenes or products which can be separated by fractional distillation from the $C_8$ aromatics prior to sending the $C_8$ aromatic feedstream to the PSA unit. An additional catalyst reactor may be used to treat the para-xylene-lean reject stream from the crystallization unit to convert at least a portion of any ethylbenzene in the stream to xylenes or products which can be separated by fractional distillation from the $C_8$ aromatics prior to sending the $C_8$ aromatics to the PSA unit.

The PSA component of the present invention also relates to a pressure swing adsorption (PSA) process for separating para-xylene, or para-xylene and ethylbenzene, from mixed $C_8$ aromatics using an adsorbent comprising a para-selective adsorbent. The adsorbent is preferably a para-selective, non-acidic, molecular sieve. The adsorbent is more preferably a para-selective, non-acidic, medium pore molecular sieve. The para-selective, non-acidic medium pore molecular sieve is preferably selected from the group of molecular sieve structure types consisting of MFI, TON, MTT, EUO, MEL, and FER. The molecular sieve is preferably of the MFI structure type and the process is preferably operated in the vapor phase at elevated temperatures and pressures wherein the temperature is substantially isothermal. The para-xylene which has been separated from a $C_8$ aromatic mixture using the above PSA process is then purified by crystallization.

The PSA component of the present invention also relates to a pressure swing adsorption process for separating para-xylene from a feed comprising a gaseous mixture comprising meta-xylene and ortho-xylene under substantially isothermal conditions comprising:

(a) adsorbing the mixture onto an adsorbent comprising a para-selective adsorbent capable of selectively adsorbing para-xylene at a temperature and pressure at which at least 0.01 grams of para-xylene may be adsorbed per gram of adsorbent;

(b) producing a first effluent stream having an enriched concentration of ortho-xylene and meta-xylene;

(c) selectively removing feed from non-selective voids;

(d) selectively desorbing para-xylene by decreasing partial pressure of para-xylene; and (e) collecting a stream having an enriched concentration of para-xylene.

The present invention additionally relates to a pressure swing adsorption process for separating para-xylene from a feed comprising a gaseous mixture comprising para-xylene, meta-xylene, ortho-xylene, and ethylbenzene under substantially isothermal conditions comprising:

(a) adsorbing the mixture onto an adsorbent comprising a para-selective adsorbent capable of selectively adsorbing para-xylene and ethylbenzene at a temperature and pressure at which at least 0.01 grams of para-xylene may be adsorbed per gram of adsorbent;

(b) producing a first effluent stream having an enriched concentration of ortho-xylene and meta-xylene;

(c) selectively removing feed from non-selective voids;

(d) selectively desorbing para-xylene by decreasing partial pressure of para-xylene; and (e) collecting a stream having an enriched concentration of para-xylene and ethylbenzene.

The PSA component of the present invention further relates to a process for separating and recovering para-xylene from a gaseous mixture comprising $C_8$ aromatic hydrocarbons, the process comprising:

(a) introducing a gaseous mixture comprising meta-xylene, ortho-xylene, and para-xylene into a pressure swing adsorption unit and subjecting the mixture to pressure swing adsorption under substantially isothermal conditions using an adsorbent comprising a para-selective adsorbent capable of selectively adsorbing para-xylene at a temperature and pressure at which at least 0.01 grams of para-xylene and ethylbenzene may be adsorbed per gram of adsorbent to produce a meta-xylene and ortho-xylene-rich effluent stream comprising a mixture of ortho-xylene and meta-xylene, which contains no more than a total of about 20 mole percent of para-xylene based on total $C_8$ aromatics, and a para-xylene-rich effluent stream which contains no more than a total of about 50 mole percent of meta-xylene and ortho-xylene based on total $C_8$ aromatics;

(b) sending at least a portion of the para-xylene-rich stream to a crystallization unit and crystallizing said para-xylene-rich stream to produce a para-xylene product stream and a para-xylene-lean mother liquor stream;

(c) sending at least a portion of the meta-xylene and ortho-xylene-rich stream to an isomerization unit and isomerizing said stream to produce an isomerizate comprising an equilibrium mixture of xylenes;

(d) recycling at least a portion of the isomerizate from step (c) to step (a);

(e) sending at least a portion of the para-xylene-lean mother liquor stream from step (b) to an isomerization unit and isomerizing said stream to produce an isomerizate comprising an equilibrium mixture of xylenes; and (f) recycling at least a portion of the isomerizate from step (e) to step (a).

In the PSA process component of the invention, a stream having an enriched concentration of para-xylene will contain a greater concentration of para-xylene than the $C_8$ aromatic feedstream from which it was separated by PSA, and a stream having an enriched concentration of ortho-xylene and meta-xylene will contain a greater concentration of ortho-xylene and meta-xylene than the $C_8$ aromatic feedstream from which it was separated by PSA, and a stream having an enriched concentration of para-xylene and ethylbenzene will contain a greater concentration of para-xylene and ethylbenzene than the $C_8$ aromatic feedstream from which it was separated by PSA.

The PSA component of the present invention also relates to a process for separating and recovering para-xylene from a gaseous mixture comprising $C_8$ aromatic hydrocarbons, the process comprising:

(a) introducing a gaseous mixture comprising meta-xylene, ortho-xylene, para-xylene, and ethylbenzene into a pressure swing adsorption unit and subjecting the mixture to pressure swing adsorption under substantially isothermal conditions using an adsorbent comprising a para-selective adsorbent capable of selectively adsorbing para-xylene at a temperature and pressure at which at least 0.01 grams of para-xylene and ethylbenzene may be adsorbed per gram of adsorbent to produce a meta-xylene and ortho-xylene-rich effluent stream comprising a mixture of ortho-xylene and meta-xylene, which contains no more than a total of about 25 mole percent of para-xylene and ethylbenzene based on total $C_8$ aromatics, and a para-xylene-rich effluent stream comprising para-xylene and ethylbenzene, which contains no more than a total of about 50 mole percent of meta-xylene and ortho-xylene based on total $C_8$ aromatics;

(b) sending at least a portion of the para-xylene-rich stream to a crystallization unit and crystallizing said para-xylene-rich stream to produce a para-xylene product stream and a para-xylene-lean mother liquor stream;

(c) sending at least a portion of the meta-xylene and ortho-xylene-rich stream to an isomerization unit and isomerizing said stream to produce an isomerizate comprising an equilibrium mixture of xylenes;

(d) recycling at least a portion of the isomerizate from step (c) to step (a);

(e) sending at least a portion of the para-xylene-lean mother liquor stream from step (b) to an isomerization unit and isomerizing said stream to produce an isomerizate comprising an equilibrium mixture of xylenes; and (f) recycling at least a portion of the isomerizate from step (e) to step (a).

The invention also relates to the above process of wherein the gaseous mixture comprising meta-xylene, ortho-xylene, para-xylene, and ethylbenzene is contacted with an ethylbenzene conversion catalyst to remove at least a portion of the ethylbenzene prior to being subjected to pressure swing adsorption in step (a).

The invention also relates to the above process wherein at least a portion of the para-xylene-lean mother liquor stream from step (b) is contacted with an ethylbenzene conversion catalyst to remove at least a portion of any ethylbenzene in the para-xylene-lean mother liquor stream and to produce an ethylbenzene-lean effluent which is then recycled to step (a).

The invention also relates to a process for separating and recovering para-xylene from a gaseous mixture comprising $C_8$ aromatic hydrocarbons, the process comprising:

(a) introducing a gaseous mixture comprising meta-xylene, ortho-xylene, para-xylene, and ethylbenzene into a pressure swing adsorption unit and subjecting the mixture to pressure swing adsorption under substantially isothermal conditions using an adsorbent comprising a para-selective adsorbent capable of selectively adsorbing para-xylene at a temperature and pressure at which at least 0.01 grams of para-xylene and ethylbenzene may be adsorbed per gram of adsorbent to produce a meta-xylene and ortho-xylene-rich effluent stream comprising a mixture of ortho-xylene and meta-xylene, which contains no more than a total of about 25 mole percent of para-xylene and ethylbenzene based on total $C_8$ aromatics, and a para-xylene-rich effluent stream comprising para-xylene and ethylbenzene, which contains no more than a total of about 50 mole percent of meta-xylene and ortho-xylene based on total $C_8$ aromatics;

(b) sending at least a portion of the para-xylene-rich stream to a crystallization unit and crystallizing said para-xylene-rich stream to produce a para-xylene product stream and a para-xylene-lean mother liquor stream;

(c) sending at least a portion of the meta-xylene and ortho-xylene-rich stream to an isomerization unit and isomerizing said stream to produce an isomerizate comprising an equilibrium mixture of xylenes;

(d) recycling at least a portion of the isomerizate from step (c) to step (a);

(e) sending at least a portion of the para-xylene-lean mother liquor stream from step (b) to an ethylbenzene conversion unit and contacting it with an ethylbenzene conversion catalyst to remove at least a portion of any ethylbenzene in the para-xylene-lean mother liquor stream and to produce an ethylbenzene-lean effluent; and (f) combining at least a portion of the ethylbenzene-lean effluent produced in step (e) with the isomerizate from step (c) and recycling the combined effluents to step (a).

The present invention relates to a pressure swing adsorption method for separating para-xylene from a gaseous feed mixture containing meta-xylene and ortho-xylene under substantially isothermal conditions comprising:

(a) adsorbing the mixture onto an adsorbent containing a molecular sieve capable of selectively adsorbing para-xylene at a temperature and pressure at which at least 0.01 grams of para-xylene may be adsorbed per gram of molecular sieve contained in the adsorbent;

(b) producing a first effluent stream containing a mixture of ortho-xylene and meta-xylene, having no more than a total of about 25 mole percent of para-xylene based on total $C_8$ aromatics, preferably less than about 25 mole percent of para-xylene, more preferably no more than about 20 mole percent of para-xylene, more preferably less than about 20 mole percent of para-xylene, more preferably no more than about 15 mole percent of para-xylene, more preferably less than about 15 mole percent of para-xylene, more preferably no more than about 10 mole percent of para-xylene, more preferably less than about 10 mole percent of para-xylene, more preferably no more than about 5 mole percent of para-xylene, more preferably less than about 5 mole percent of para-xylene, more preferably no more than about 3 mole percent of para-xylene, more preferably less than about 3 mole percent of para-xylene, more preferably no more than about 1 mole percent of para-xylene, and most preferably less than about 1 mole percent of para-xylene based on total $C_8$ aromatics;

(c) selectively removing feed from the non-selective void volume;

(d) selectively desorbing para-xylene by decreasing partial pressure of para-xylene;

(e) collecting a stream containing para-xylene and having no more than a total of about 50 mole percent of meta-xylene and ortho-xylene based on total $C_8$ aromatics; preferably less than about 50 mole percent of meta-xylene and ortho-xylene, more preferably no more than about 45 mole percent of meta-xylene and ortho-xylene, more preferably less than about 45 mole percent of meta-xylene and ortho-xylene, more preferably no more than about 40 mole percent of meta-xylene and ortho-xylene, preferably less than about 40 mole percent of meta-xylene and ortho-xylene, more preferably no more than about 35 mole percent of meta-xylene and ortho-xylene, more preferably less than about 35 mole percent of meta-xylene and ortho-xylene, more preferably no more than about 30 mole percent of meta-xylene and ortho-xylene, more preferably less than about 30 mole percent of meta-xylene and ortho-xylene, more preferably no more than about 25 mole percent of meta-xylene and ortho-xylene, more preferably less than about 25 mole percent of meta-xylene and ortho-xylene, more preferably no more than about 20 mole percent of meta-xylene and ortho-xylene, more preferably less than about 20 mole percent of meta-xylene and ortho-xylene, more preferably no more than about 15 mole percent of meta-xylene and ortho-xylene, more preferably less than about 15 mole percent of meta-xylene and ortho-xylene, more preferably no more than about 10 mole percent of para-xylene, more preferably less than about 10 mole percent of meta-xylene and ortho-xylene, more preferably no more than about 5 mole percent of meta-xylene and ortho-xylene, and most preferably less than about 5 mole percent of meta-xylene and ortho-xylene based on total $C_8$ aromatics; and (f) subjecting the para-xylene-containing stream collected in step (e) to crystallization and recovering high purity para-xylene.

The meta-xylene and ortho-xylene-containing stream from step (b) may be contacted with a catalyst system comprising at least one catalyst which isomerizes meta-xylene and ortho-xylene to give an equilibrium mixture of meta-xylene, ortho-xylene, and para-xylene which may then be sent to the PSA unit for separation.

A practice of the invention involves principally proceeding by repeated cycles comprising in an individual cycle the above steps (a) through (e) to obtain a $C_8$ aromatic stream containing at least about 50 mole percent para-xylene; preferably at least about 55 mole percent para-xylene, more preferably at least about 60 mole percent para-xylene, more preferably at least about 65 mole percent para-xylene, more preferably at least about 70 mole percent para-xylene, more preferably at least about 75 mole percent para-xylene, more preferably at least about 80 mole percent para-xylene, more preferably at least about 85 mole percent para-xylene, more preferably at least about 90 mole percent para-xylene, and more preferably at least about 95 mole percent para-xylene which may then be subjected to crystallization to obtain a purified para-xylene product.

In step (a) of the process of the present invention described above, it is preferable that at least 0.01 g of para-xylene be adsorbed per gram of para-selective adsorbent contained in the adsorbent; more preferable that at least 0.02 g of para-xylene be adsorbed per gram of para-selective adsorbent contained in the adsorbent; and even more preferable that at least 0.03 g of para-xylene be adsorbed per gram of para-selective adsorbent contained in the adsorbent.

Preferably, the first effluent stream mixture of ortho-xylene and meta-xylene produced in the process of the invention, as, for example, in step (b) above, will contain no more than about 25 mole percent of para-xylene based on total $C_8$ aromatics, preferably less than about 25 mole percent of para-xylene, more preferably no more than about 20 mole percent of para-xylene, more preferably less than about 20 mole percent of para-xylene, more preferably no more than about 15 mole percent of para-xylene, more preferably less than about 15 mole percent of para-xylene, more preferably no more than about 10 mole percent of para-xylene, more preferably less than about 10 mole percent of para-xylene, more preferably no more than about 5 mole percent of para-xylene, more preferably less than about 5 mole percent of para-xylene, more preferably no more than about 3 mole percent of para-xylene, more preferably less than about 3 mole percent of para-xylene, and still more preferably no more than about 1 mole percent of para-xylene, and even more preferably less than about 1 mole percent of para-xylene.

Preferably, the para-xylene-containing stream collected in the process of the invention, as, for example, in step (e) above, will contain no more than a total of about 50 mole percent of meta-xylene and ortho-xylene based on total $C_8$ aromatics, preferably less than a total of about 50 mole percent of meta-xylene and ortho-xylene, more preferably no more than a total of about 45 mole percent of meta-xylene and ortho-xylene, preferably less than a total of about 45 mole percent of meta-xylene and ortho-xylene, more preferably no more than a total of about 40 mole percent of meta-xylene and ortho-xylene, preferably less than a total of about 40 mole percent of meta-xylene and ortho-xylene, more preferably no more than a total of about 30 mole percent of meta-xylene and ortho-xylene, preferably less than a total of about 30 mole percent of meta-xylene and ortho-xylene, preferably no more than a total of about 25 mole percent of meta-xylene and ortho-xylene; preferably less than a total of about 25 mole percent of meta-xylene and ortho-xylene; more preferably no more than a total of about 20 mole percent of meta-xylene and ortho-xylene, preferably less than a total of about 20 mole percent of meta-xylene and ortho-xylene, more preferably no more than a total of about 15 mole percent of meta-xylene and ortho-xylene, preferably less than a total of about 15 mole percent of meta-xylene and ortho-xylene, more preferably no more than a total of about 10 mole percent of meta-xylene and ortho-xylene, preferably less than a total of about 10 mole percent of meta-xylene and ortho-xylene, more preferably no more than a total of about 5 mole percent of meta-xylene and ortho-xylene, and most preferably less than a total of about 5 mole percent of meta-xylene and ortho-xylene based on total $C_8$ aromatics.

In the most preferred embodiments of the invention, the effluent product stream containing para-xylene, or para-xylene and ethylbenzene, will be substantially free of meta-xylene and ortho-xylene, and the effluent product stream containing meta-xylene and ortho-xylene will be substantially free of para-xylene, or substantially free of para-xylene and ethylbenzene.

The molecular sieve is preferably a para-selective, non-acidic medium pore molecular sieve. Preferably, the molecular sieve comprises silicalite, and more preferably, the molecular sieve comprises orthorhombic crystals of silicalite having an average minimum dimension of at least about 0.2 μm.

In one embodiment of the invention, the adsorbent comprises a para-selective, adsorbent and a binder. The binder is preferably selected from the group consisting of clay, alumina, silica, titania, zirconia, silica-alumina, silica-magnesia, silica-zirconia, silica-thoria, silica-beryllia, silica-titania, silica-alumina-thoria, silica-alumina-zirconia, silica-alumina-magnesia, silica-magnesia-zirconia, and aluminum phosphate.

A para-selective adsorbent is an adsorbent that, when subjected to an equal molar mixture of $C_8$ aromatics at 50° C., adsorbs pX and EB preferentially over mX and oX, such that the total pX and EB in the adsorbate is at least about 75% relative to the total $C_8$ aromatics.

A preferred para-selective adsorbent, when subjected to an equal molar mixture of $C_8$ aromatics at 50° C., will adsorb pX and EB preferentially over mX and oX, such that the total pX and EB in the adsorbate is greater than about 75% relative to the total $C_8$ aromatics.

A more preferred para-selective adsorbent, when subjected to an equal molar mixture of $C_8$ aromatics at 50° C., will adsorb pX and EB preferentially over mX and oX, such that the total pX and EB in the adsorbate is at least about 80% relative to the total $C_8$ aromatics, even more preferably, at least about 85% relative to the total $C_8$ aromatics, still more preferably, at least about 90% relative to the total $C_8$ aromatics; and yet more preferably, at least about 95% relative to the total $C_8$ aromatics; and most preferably, at least about 97% relative to the total $C_8$ aromatics.

In the present invention the pressure swing adsorption operating temperature is preferably at least about 350° F., preferably about 350° F. to about 750° F., more preferably from about 400° F. to about 750° F. more preferably from about 450° F. to about 750° F. and the operating pressure is at least about 30 psia (206 kPa), preferably about 50 psia (345 kPa) to about 400 psia, more preferably from about 100 psia to about 400 psia (from about 206 kPa to about 2760 kPa).

In the process of the present invention, the para-xylene or para-xylene and ethylbenzene rich stream from the pressure swing adsorption unit is fed to a fractional crystallization unit. Crystallization is conducted by passing the mixture into a crystallizer maintained at a temperature sufficient to induce crystallization of pX, generally between about 40° F. and −130° F. The lower the temperature, the more pX that can be removed from the system. An advantage of the process of the invention is that a significant portion of the mX and oX are removed by the PSA unit. As a result, the temperature at which pX can be crystallized without co-crystallization of impurities is lowered substantially, allowing a higher percentage of pX product to be removed from the system per pass. Crystallization can be done in one stage or multiple stages. When the para-xylene concentration in the stream from the pressure swing adsorption unit is sufficiently, high, crystallization of para-xylene may be conducted at temperatures of about 10° F. to abut 55° F.

In a preferred embodiment of the invention, the para-xylene-enriched stream from the PSA unit is crystallized in a first crystallizer at a temperature of about 10° F. to about 55° F.; an effluent comprising para-xylene crystals in a mother liquor is recovered, and the para-xylene crystals are separated from the mother liquor in a first separation unit, washed with liquid para-xylene, and completely melted to give a liquid para-xylene product of high purity. The filtrate from this first crystallization is subjected to fractional crystallization to recover additional para-xylene product.

The present invention additionally relates to a pressure swing adsorption method to separate para-xylene and ethylbenzene from a gaseous feed mixture containing meta-xylene and ortho-xylene under substantially isothermal conditions comprising:

(a) adsorbing the mixture onto an adsorbent containing a molecular sieve capable of selectively sorbing para-xylene and ethylbenzene at a temperature and pressure at which at least 0.01 grams of para-xylene and ethylbenzene may be adsorbed per gram of molecular sieve;

(b) producing a first effluent stream containing a mixture of ortho-xylene and meta-xylene having no more than a total of about 25 mole percent of para-xylene and ethylbenzene based on total $C_8$ aromatics, preferably less than about 25 mole percent of para-xylene and ethylbenzene, more preferably no more than about 20 mole percent of para-xylene and ethylbenzene, more preferably less than about 20 mole percent of para-xylene and ethylbenzene, more preferably no more than about 15 mole percent of para-xylene and ethylbenzene, more preferably less than about 15 mole percent of para-xylene and ethylbenzene, more preferably no more than about 10 mole percent of para-xylene and ethylbenzene, more preferably less than about 10 mole percent of para-xylene and ethylbenzene, more preferably no more than about 5 mole percent of para-xylene and ethylbenzene, more preferably less than about 5 mole percent of para-xylene and ethylbenzene, more preferably no more than about 3 mole percent of para-xylene and ethylbenzene, more preferably less than about 3 mole percent of para-xylene and ethylbenzene, more preferably no more than about 1 mole percent of para-xylene and ethylbenzene, and most preferably less than about 1 mole percent of para-xylene and ethylbenzene based on total $C_8$ aromatics;

(c) selectively removing feed from the non-selective void volume;

(d) selectively desorbing para-xylene and ethylbenzene by decreasing partial pressure of para-xylene and ethylbenzene; and (e) collecting a stream containing para-xylene and ethylbenzene and having no more than a total of about 50 mole percent of meta-xylene and ortho-xylene based on total $C_8$ aromatics.

(f) subjecting the para-xylene and ethylbenzene-containing stream collected in step (e) to crystallization and recovering high purity para-xylene.

In one embodiment of the present invention, the effluent stream containing a mixture of ortho-xylene and meta-xylene may be contacted with a catalyst system comprising at least one catalyst which isomerizes meta-xylene and ortho-xylene to give an equilibrium mixture of meta-xylene, ortho-xylene, and para-xylene which may then be sent to the PSA unit for separation. When the gaseous feed stream additionally contains ethylbenzene, the meta-xylene and ortho-xylene-containing effluent stream may be contacted with a catalyst system comprising at least one catalyst which converts at least a portion of any ethylbenzene in the stream to products that can be separated from the xylenes by distillation and which isomerizes meta-xylene and ortho-xylene to give an equilibrium mixture of meta-xylene, ortho-xylene, and para-xylene which may then be sent to the PSA unit for separation.

A para-xylene-lean reject stream from the crystallization unit which comprises $C_8$ aromatics may be sent to a catalyst reactor, where the xylenes are isomerized to equilibrium and where at least a portion of the ethylbenzene is converted to products which can be separated by fractional distillation from the $C_8$ aromatics. The catalyst or combination of catalysts in the reactor can be any that are suitable for xylene isomerization and ethylbenzene conversion, as known to those skilled in the art. Examples of such catalysts are described in EP 138,617, U.S. Pat. No. 5,001,296, U.S. Re. 31,782, U.S. Pat. Nos. 4,098,836 and 4,899,011 incorporated herein by reference in their entireties. Suitable isomerization conditions include a temperature of about 250° C. to about 500° C., preferably about 340° C. to about 430° C., a pressure of about atmospheric to about 400 psig, preferably in the range of about 100 psig to about 300 psig, a hydrogen to hydrocarbon mole ratio of about 0.5:1 to about 10:1, and a liquid weight hourly space velocity of about 0.5 to about 100 $hr^{-1}$. The para-xylene-lean reject stream may be combined with the mX/oX-rich effluent stream from the PSA prior to sending it to the isomerization reactor.

An additional catalyst reactor may be used to pretreat the $C_8$ aromatic feed to convert at least a portion of the ethylbenzene to products which can be separated by fractional distillation from the $C_8$ aromatics prior to sending the $C_8$ aromatic feedstream to the PSA unit.

In an alternate embodiment, an additional catalyst reactor may be used to treat the para-xylene-lean reject stream from the crystallizer to convert at least a portion of the ethylbenzene in it to xylenes or products which can be separated by fractional distillation from the $C_8$ aromatics prior to sending the $C_8$ aromatic feedstream to the PSA unit.

The catalyst system in the additional catalyst reactor used to convert ethylbenzene can be any catalyst system suitable for ethylbenzene dealkylation, hydrodeethylation or hydroisomerization. Examples of catalyst systems for dealkylation are disclosed in Re. 31,782 and U.S. Pat. No. 4,908,342, incorporated herein by reference in their entireties. Examples of catalyst systems for hydrodeethylation are disclosed in U.S. Pat. Nos. 4,899,011 and 5,367,099 incorporated herein by reference in their entireties. Examples of catalyst systems for hydroisomerization are disclosed in U.S. Pat. Nos. 5,028,573, 6,150,292 and 5,908,967 incorporated herein by reference in their entireties.

A practice of the invention involves principally proceeding by repeated cycles comprising in an individual cycle the above steps (a) through (e) to produce an effluent stream comprising para-xylene and ethylbenzene containing no more than a total of about 50 mole percent of meta-xylene and ortho-xylene based on total $C_8$ aromatics from which para-xylene is separated and purified via crystallization, and another effluent stream comprising meta-xylene and ortho-xylene containing no more than a total of about 20 mole percent of para-xylene based on total $C_8$ aromatics which is contacted with an isomerization catalyst system to produce an equilibrium mixture of meta-xylene, ortho-xylene, and para-xylene.

In step (a) of the process of the present invention described above, it is preferable that at least 0.01 g of para-xylene and ethylbenzene be adsorbed per gram of molecular sieve contained in the adsorbent; more preferable that at least 0.02 g of para-xylene and ethylbenzene be adsorbed per gram of molecular sieve contained in the adsorbent; still more preferable that at least 0.03 g of para-xylene and ethylbenzene be adsorbed per gram of molecular sieve contained in the adsorbent.

The present invention also relates to a process for separating a mixture of organic compounds having normal boiling points in a temperature range from about 80° C. to about 160° C., which process comprises:

(a) providing an adsorbent bed comprising a molecular sieve which exhibits capacity to selectively adsorb and desorb para-xylene and ethylbenzene under substantially isothermal conditions of temperature at operating pressure, disposed in a vessel having at least one inlet and at least one outlet such that gas entering an inlet passes through the adsorbent bed to an outlet, and containing a purge gas substantially free of $C_8$ aromatic compounds;

(b) flowing a gaseous feed mixture comprising xylenes and ethylbenzene into the bed through one or more of the vessel inlets, and collecting an effluent from one or more of the outlets comprising purge gas substantially free of $C_8$ aromatic compounds while selectively adsorbing para-xylene and ethylbenzene from the gaseous mixture under substantially isothermal conditions in the bed;

(c) continuing the flow of gaseous feed and collecting from one or more of the outlets and segregating a second effluent comprising m-xylene and o-xylene having no more than about 25 mole percent of p-xylene and ethylbenzene based on total $C_8$ aromatics;

(d) stopping the feed mixture flowing into the bed through one or more inlets just prior to breakthrough (i.e., the adsorption front is close to the exit end of the adsorbent column), and flowing purge gas preferably in a direction counter to the direction of the $C_8$ aromatic feed, while maintaining substantially isothermal conditions in the bed, and collecting from one or more of the outlets an effluent gaseous mixture of $C_8$ aromatic feed until effluent at the outlet contains no more than about 50 mole percent of meta-xylene and ortho-xylene based on total $C_8$ aromatics;

(e) continuing the flow of purge gas and collecting from one or more of the outlets and segregating an effluent comprising ethylbenzene and p-xylene which contains no more than about 50 mole percent of meta-xylene and ortho-xylene based on total $C_8$ aromatics;

(f) subjecting the para-xylene-containing stream collected in step (e) to crystallization and recovering high purity para-xylene; and (h) optionally, contacting the meta-xylene and ortho-xylene-containing stream from step (c) with a catalyst system, comprising at least one catalyst, which converts at least a portion of the ethylbenzene in the stream to products that can be separated from the xylenes by distillation and which isomerizes meta-xylene and ortho-xylene to produce an equilibrium mixture of meta-xylene, ortho-xylene, and para-xylene In a preferred embodiment of the above process, in step (d) the effluent gaseous mixture of $C_8$ aromatic feed will be collected until the effluent at the outlet is substantially free of meta-xylene and ortho-xylene.

A practice of the invention involves principally proceeding by repeated cycles comprising in an individual cycle the above steps (a) through (e) to produce an effluent stream comprising para-xylene and ethylbenzene containing no more than a total of about 50 mole percent of meta-xylene and ortho-xylene based on total $C_8$ aromatics from which para-xylene is separated and purified via crystallization, and another effluent stream comprising meta-xylene and ortho-xylene containing no more than a total of about 25 mole percent of para-xylene which is contacted with a catalyst system, comprising at least one catalyst, which converts at least a portion of the ethylbenzene in the stream to products that can be separated from the xylenes by distillation and which isomerizes meta-xylene and ortho-xylene to give an equilibrium mixture of meta-xylene, ortho-xylene, and para-xylene to produce an equilibrium mixture of meta-xylene, ortho-xylene, and para-xylene.

In a preferred embodiment of the process, the flow of the purge gas is counter current to the flow of the gaseous feed mixture.

In one embodiment of the process, steps (b) through (e) are repeated with a cycle time of from about 2 minutes to about 200 minutes, preferably with a cycle time of from about 3 minutes to about 50 minutes, more preferably with a cycle time of from about 3 minutes to about 30 minutes.

In an embodiment of the process at least a portion of the effluent gaseous mixture collected in step (d) is admixed with the gaseous feed mixture in subsequent cycles.

In another embodiment of the process, the purge gas comprises hydrogen, and steps (b) through (e) are repeated with a cycle time of from about 3 minutes to about 30 minutes under substantially isothermal conditions at a temperature of about 350° F. to about 750° F. and at constant operating pressure at a pressure of at least about 30 psia to about 400 psia.

An additional embodiment of the invention comprises a process for separating a mixture of ethylbenzene and the isomers of xylene, which process comprises:

(a) providing an adsorbent bed comprising a molecular sieve which exhibits capacity to selectively adsorb and desorb para-xylene and ethylbenzene under substantially isothermal conditions at operating pressure, disposed in a vessel having at least one inlet and at least one outlet such that gas entering an inlet passes through the particulate bed to an outlet and pressurizing the vessel with a mixture comprising meta-xylene and ortho-xylene to a preselected pressure for adsorption;

(b) flowing a gaseous feed mixture comprising xylene isomers and ethylbenzene into the adsorbent bed through one or more inlets and displacing the meta-xylene and ortho-xylene in the vessel while selectively adsorbing ethylbenzene and para-xylene from the gaseous feed mixture under substantially isothermal conditions in the adsorbent bed;

(c) collecting from one or more of the outlets a first effluent product comprising meta-xylene and ortho-xylene which contains no more than a total of about 25 mole percent of ethylbenzene and para-xylene based on total $C_8$ aromatics while maintaining substantially isothermal conditions in the adsorbent bed and the flow of feed at the pressure for adsorption;

(d) replacing the feed mixture flowing into the bed though one or more inlets with a purge gas comprising para-xylene and ethylbenzene substantially free of meta-xylene and ortho-xylene while maintaining the pressure for adsorption and substantially isothermal conditions in the bed, and collecting from one or more of the outlets a gaseous mixture comprising feed;

(e) reducing the pressure to desorb ethylbenzene and para-xylene while maintaining substantially isothermal conditions in the bed; and (f) collecting a second effluent product comprising ethylbenzene and para-xylene which contains no more than a total of about 50 mole percent of meta-xylene and ortho-xylene based on total $C_8$ aromatics.

In a preferred embodiment of the above process:

(a) the flow of said para-xylene and ethylbenzene purge gas is countercurrent to the flow of the gaseous feed mixture;

(b) the para-xylene and ethylbenzene effluent flow during depressurization is countercurrent to the flow of the gaseous feed mixture; and (c) the flow of meta-xylene and ortho-xylene to pressurize the vessel is countercurrent to the feed gas flow.

A further embodiment of the invention comprises a process for separating a mixture of ethylbenzene and the isomers of xylene, which process comprises:

(a) providing at least two adsorbent beds containing a molecular sieve which exhibits capacity to selectively adsorb and desorb para-xylene and ethylbenzene under substantially isothermal conditions at operating pressure, disposed in sequentially connected or interconnected vessels, each having at least one inlet and at least one outlet such that gas entering an inlet passes through the particulate bed to an outlet, and pressurizing a first vessel with a mixture comprising meta-xylene and ortho-xylene to a preselected pressure for adsorption;

(b) flowing a gaseous feed mixture comprising xylene isomers and ethylbenzene into the adsorbent bed in the first vessel though one or more inlets and displacing the meta-xylene and ortho-xylene in the vessel while selectively adsorbing ethylbenzene and para-xylene from the gaseous feed mixture under substantially isothermal conditions in the adsorbent bed;

(c) collecting from one or more of the outlets a first effluent product comprising meta-xylene and ortho-xylene which contains no more than a total of about 25 mole percent of ethylbenzene and para-xylene based on total $C_8$ aromatics while maintaining substantially isothermal conditions in the adsorbent bed and the flow of feed at the pressure for adsorption;

(d) stopping the flow of feed and reducing the pressure in the first vessel sufficiently to permit removal of at least a portion of the feed from non-selective voids while maintaining substantially isothermal conditions in the bed by equalizing the pressure in the first vessel with the pressure in the second vessel which is at a lower pressure;

(e) further reducing the pressure in the first vessel to desorb ethylbenzene and para-xylene while maintaining substantially isothermal conditions in the bed; and (f) collecting a second effluent product comprising ethylbenzene and para-xylene which contains no more than a total of about 50 mole percent of meta-xylene and ortho-xylene based on total $C_8$ aromatics.

In the above process, following step (f), a purge gas comprising meta-xylene and ortho-xylene can be added to the first vessel to displace para-xylene and ethylbenzene in the non-selective voids, and an effluent comprising the para-xylene and ethylbenzene is collected.

Another embodiment of the present invention comprises a process for separating a mixture of ethylbenzene and the isomers of xylene, which process comprises:

(a) providing an adsorbent bed comprising a molecular sieve which exhibits capacity to selectively adsorb and desorb para-xylene and ethylbenzene under substantially isothermal conditions at operating pressure, disposed in a vessel having at least one inlet and at least one outlet such that gas entering an inlet passes through the particulate bed to an outlet and pressurizing the vessel with a mixture of substantially meta-xylene and ortho-xylene to a preselected pressure for adsorption;

(b) flowing a gaseous feed mixture comprising xylene isomers and ethylbenzene into the adsorbent bed though one or more inlets and displacing the meta-xylene and ortho-xylene in the vessel while selectively adsorbing ethylbenzene and para-xylene from the gaseous feed mixture under substantially isothermal conditions in the adsorbent bed;

(c) collecting from one or more of the outlets a first effluent product comprising meta-xylene and ortho-xylene which contains no more than a total of about 25 mole percent of ethylbenzene and para-xylene based on total $C_8$ aromatics while maintaining substantially isothermal conditions in the adsorbent bed and the flow of feed at the pressure for adsorption;

(d) stopping the flow of feed and reducing operating pressure to a pressure at which para-xylene and ethylbenzene desorb while maintaining substantially isothermal conditions in the bed; and (e) collecting a second effluent product comprising ethylbenzene and para-xylene which contains no more than a total of about 50 mole percent of meta-xylene and ortho-xylene based on total $C_8$ aromatics.

In the above embodiment, preferably, following step (e), a purge gas comprising meta-xylene and ortho-xylene is added to the first vessel to displace para-xylene and ethylbenzene in the non-selective voids, and an effluent comprising the para-xylene and ethylbenzene is collected.

In the embodiments of the pressure swing adsorption process of the present invention described above, it is preferred that the first effluent stream mixture of ortho-xylene and meta-xylene produced in the process of the invention will contain no more than about 25 mole percent of para-xylene based on total $C_8$ aromatics, preferably less than about 25 mole percent of para-xylene, more preferably no more than about 20 mole percent of para-xylene, more preferably less than about 20 mole percent of para-xylene, more preferably no more than about 15 mole percent of para-xylene, more preferably less than about 15 mole percent of para-xylene, more preferably no more than about 10 mole percent of para-xylene, more preferably less than about 10 mole percent of para-xylene, more preferably no more than about 5 mole percent of para-xylene, more preferably less than about 5 mole percent of para-xylene, more preferably no more than about 3 mole percent of para-xylene, more preferably less than about 3 mole percent of para-xylene, and still more preferably no more than about 1 mole percent of para-xylene.

In the embodiments of the pressure swing adsorption process of the present invention described above wherein the first effluent mX/oX stream contains both para-xylene and ethylbenzene, it is preferred that the first effluent stream mixture of ortho-xylene and meta-xylene produced in the process of the invention will contain no more than about 25 mole percent of para-xylene and ethylbenzene based on total $C_8$ aromatics, preferably less than about 25 mole percent of para-xylene and ethylbenzene, more preferably no more than about 20 mole percent of para-xylene and ethylbenzene, more preferably less than about 20 mole percent of para-xylene and ethylbenzene, more preferably no more than about 15 mole percent of para-xylene and ethylbenzene, more preferably less than about 15 mole percent of para-xylene and ethylbenzene, more preferably no more than about 10 mole percent of para-xylene and ethylbenzene, more preferably less than about 10 mole percent of para-xylene and ethylbenzene, more preferably no more than about 5 mole percent of para-xylene and ethylbenzene, more preferably less than about 5 mole percent of para-xylene and ethylbenzene, more preferably no more than about 3 mole percent of para-xylene and ethylbenzene, more preferably less than about 3 mole percent of para-xylene and ethylbenzene, and still more preferably no more than about 3 mole percent of para-xylene and ethylbenzene.

In the embodiments of the pressure swing adsorption process of the present invention described above, it is preferred that the para-xylene-containing stream collected in the process of the invention will contain no more than a total of about 50 mole percent of meta-xylene and ortho-xylene based on total $C_8$ aromatics, preferably less than a total of about 50 mole percent of meta-xylene and ortho-xylene, more preferably no more than a total of about 45 mole percent of meta-xylene and ortho-xylene, preferably less than a total of about 45 mole percent of meta-xylene and ortho-xylene, more preferably no more than a total of about 40 mole percent of meta-xylene and ortho-xylene, preferably less than a total of about 40 mole percent of meta-xylene and ortho-xylene, more preferably no more than a total of about 30 mole percent of meta-xylene and ortho-xylene, preferably less than a total of about 30 mole percent of meta-xylene and ortho-xylene, preferably no more than a total of about 25 mole percent of meta-xylene and ortho-xylene; preferably less than a total of about 25 mole percent of meta-xylene and ortho-xylene; more preferably no more than a total of about 20 mole percent of meta-xylene and ortho-xylene, preferably less than a total of about 20 mole percent of meta-xylene and ortho-xylene, more preferably no more than a total of about 15 mole percent of meta-xylene and ortho-xylene, preferably less than a total of about 15 mole percent of meta-xylene and ortho-xylene, more preferably no more than a total of about 10 mole percent of meta-xylene and ortho-xylene, preferably less than a total of about 10 mole percent of meta-xylene and ortho-xylene, more preferably no more than a total of about 5 mole percent of meta-xylene and ortho-xylene, and most preferably less than a total of about 5 mole percent of meta-xylene and ortho-xylene based on total $C_8$ aromatics.

In the most preferred embodiments of the pressure swing adsorption process of the present invention, the effluent product stream containing para-xylene, or para-xylene and ethylbenzene, will be substantially free of meta-xylene and ortho-xylene, and the effluent product stream containing meta-xylene and ortho-xylene will be substantially free of para-xylene, or substantially free of para-xylene and ethylbenzene.

A purge gas substantially free of $C_8$ aromatic compounds will contain no more than about 10 wt %, and preferably less than about 5 wt %, and most preferably less than about 2 wt % of $C_8$ aromatic compounds.

A fraction or stream substantially free of p-xylene and ethylbenzene will contain no more than a total of about 5 mole percent of p-xylene and ethylbenzene based on total $C_8$ aromatics.

A fraction or stream substantially free of para-xylene will contain no more than about 5 mole percent of para-xylene based on total $C_8$ aromatics. Preferably such a fraction will contain no more than about 1 mole percent of para-xylene based on total $C_8$ aromatics.

For those process steps conducted at constant pressure, those skilled in the art will recognize that during operation there may be slight variations in pressure due to pressure drops across the system or changes in flows; however the pressure will remain substantially constant.

A fraction or stream substantially free of m-xylene and o-xylene will contain no more than a total of about 25 mole percent of m-xylene and o-xylene based on total $C_8$ aromatics. Preferably such a stream will contain no more than about 20 mole percent, more preferably no more than about 15 mole percent; still more preferably no more than about 10 mole percent; and most preferably no more than about 5 mole percent of m-xylene and o-xylene based on total $C_8$ aromatics.

The present invention also relates to a method of pressure swing adsorption which includes a plurality of steps and which provides recovery from a mixture comprising $C_8$ aromatics of a product stream of p-xylene or p-xylene and ethylbenzene which is substantially free of m-xylene and o-xylene as well as a product stream of meta-xylene and ortho-xylene which is substantially free of p-xylene and ethylbenzene. The present invention provides a pressure swing adsorption process whereby there can be obtained from a feed comprising $C_8$ aromatics a high yield of a high purity product stream of p-xylene and ethylbenzene and also a high yield of a high purity product stream of m-xylene and o-xylene.

DESCRIPTION OF THE PREFERRED EMBODIMENT(S)

The present invention relates to a process for producing para-xylene integrating pressure swing adsorption for separating para-xylene and ethylbenzene from mixed $C_8$ aromatics with recovery of para-xylene by crystallization. The pressure swing adsorption component of the process uses selective adsorption, selective desorption and displacement at substantially isothermal temperatures to provide an effluent stream of para-xylene and ethylbenzene having no more than a total of about 50 mole percent of meta-xylene and ortho-xylene based on total $C_8$ aromatics and which is preferably substantially pure, and an effluent stream of ortho-xylene and meta-xylene having no more than a total of about 25 mole percent of para-xylene and ethylbenzene based on total $C_8$ aromatics and which is preferably substantially pure. High purity para-xylene is recovered from the para-xylene/ethylbenzene stream by crystallization.

Figure 7:
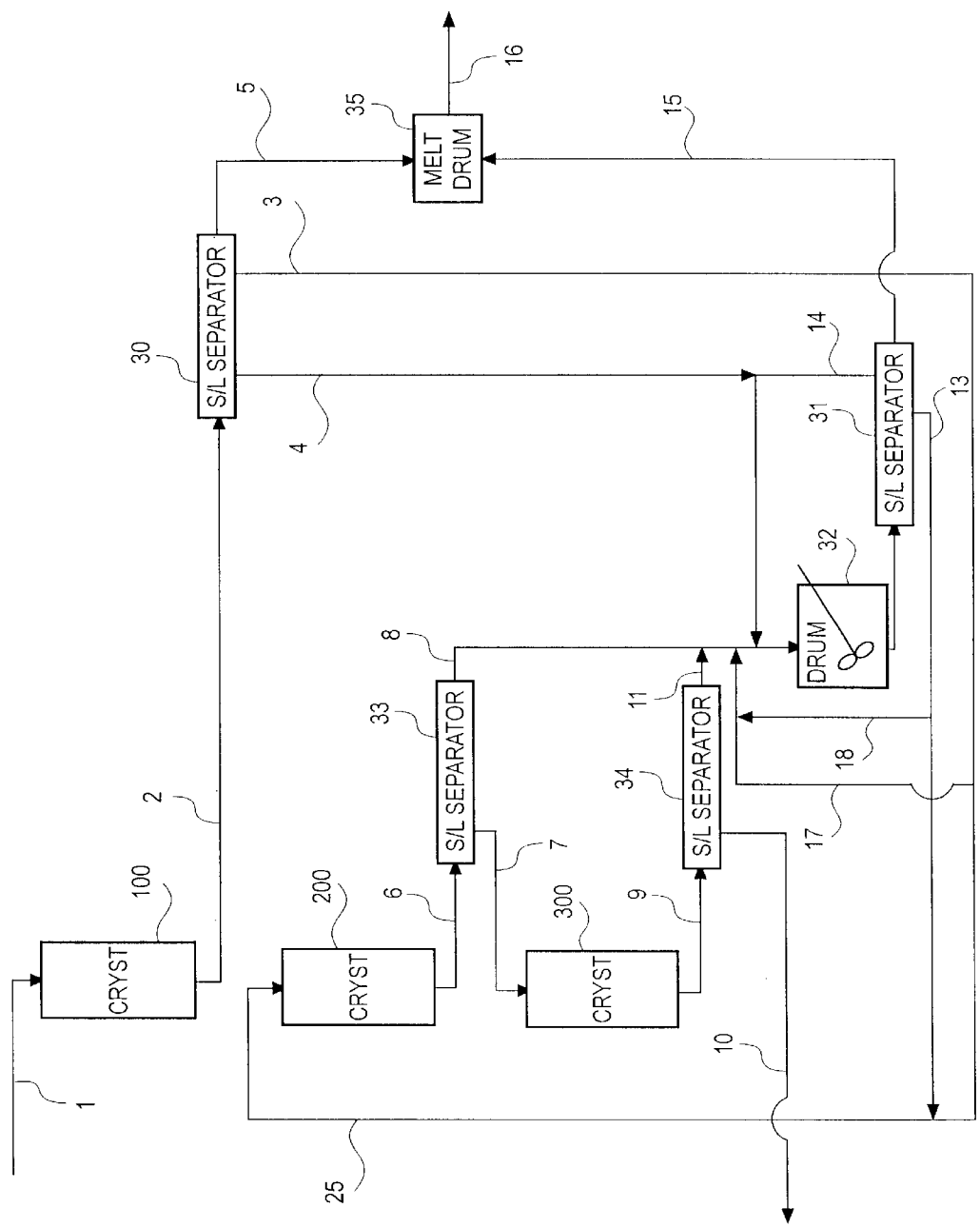
FIG. 7 shows a schematic of an embodiment of a crystallization process which may be used in combination with PSA in the present invention in which three crystallization steps and one reslurry step are used and in which at least a portion of the reject filtrate from the separation of the effluent from the reslurry drum is recycled to the second crystallization step. High purity para-xylene product is obtained from the first crystallization step without being subjected to recycling or recrystallization.
Figure 8:
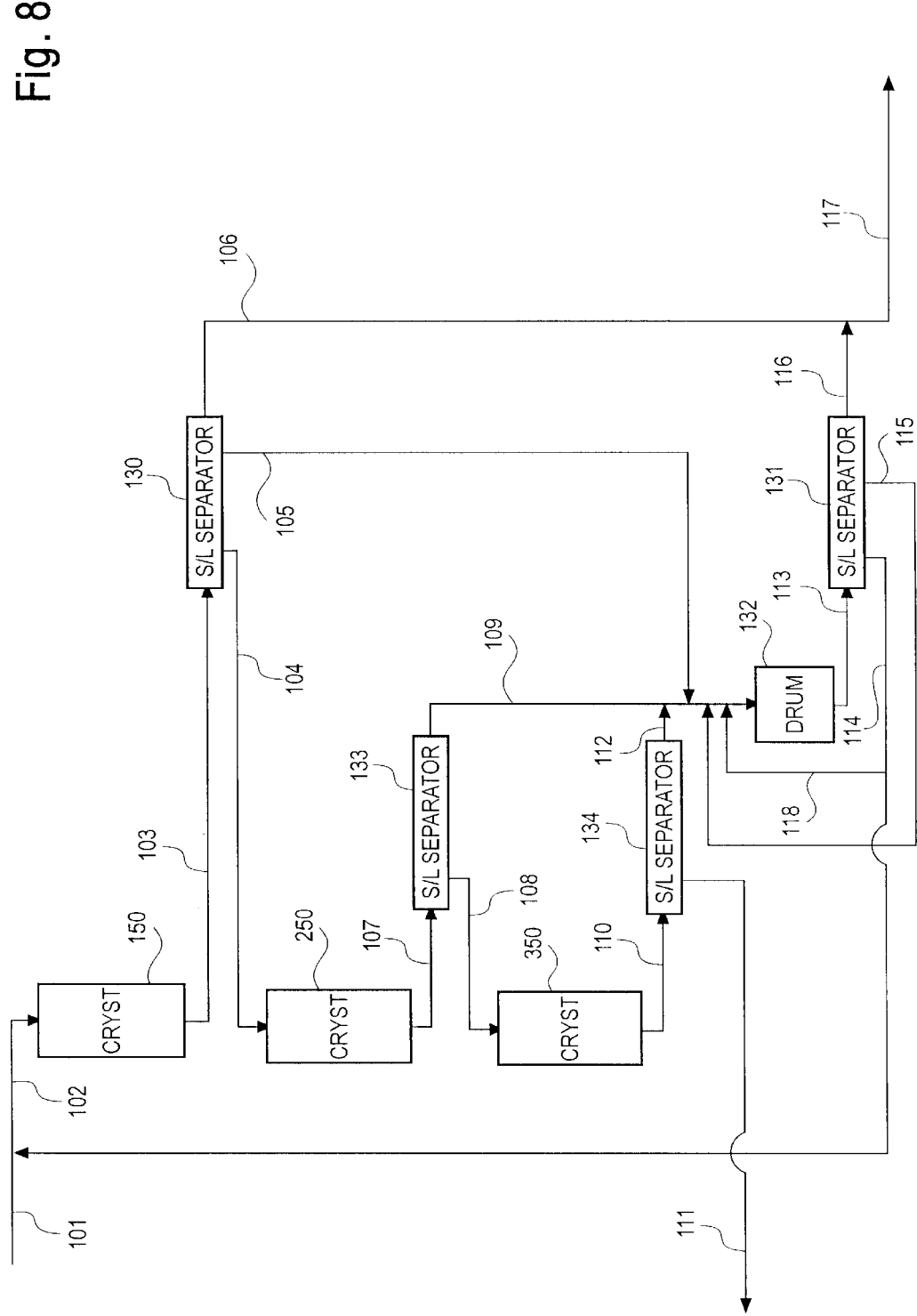
FIG. 8 shows a schematic of an embodiment of another crystallization process which may be used in combination with PSA in the present invention in which at least a portion of the reject filtrate from the separation of the effluent from the reslurry drum is combined with the feed going to the first crystallization step rather than being sent to the second crystallization step.
Figure 9:
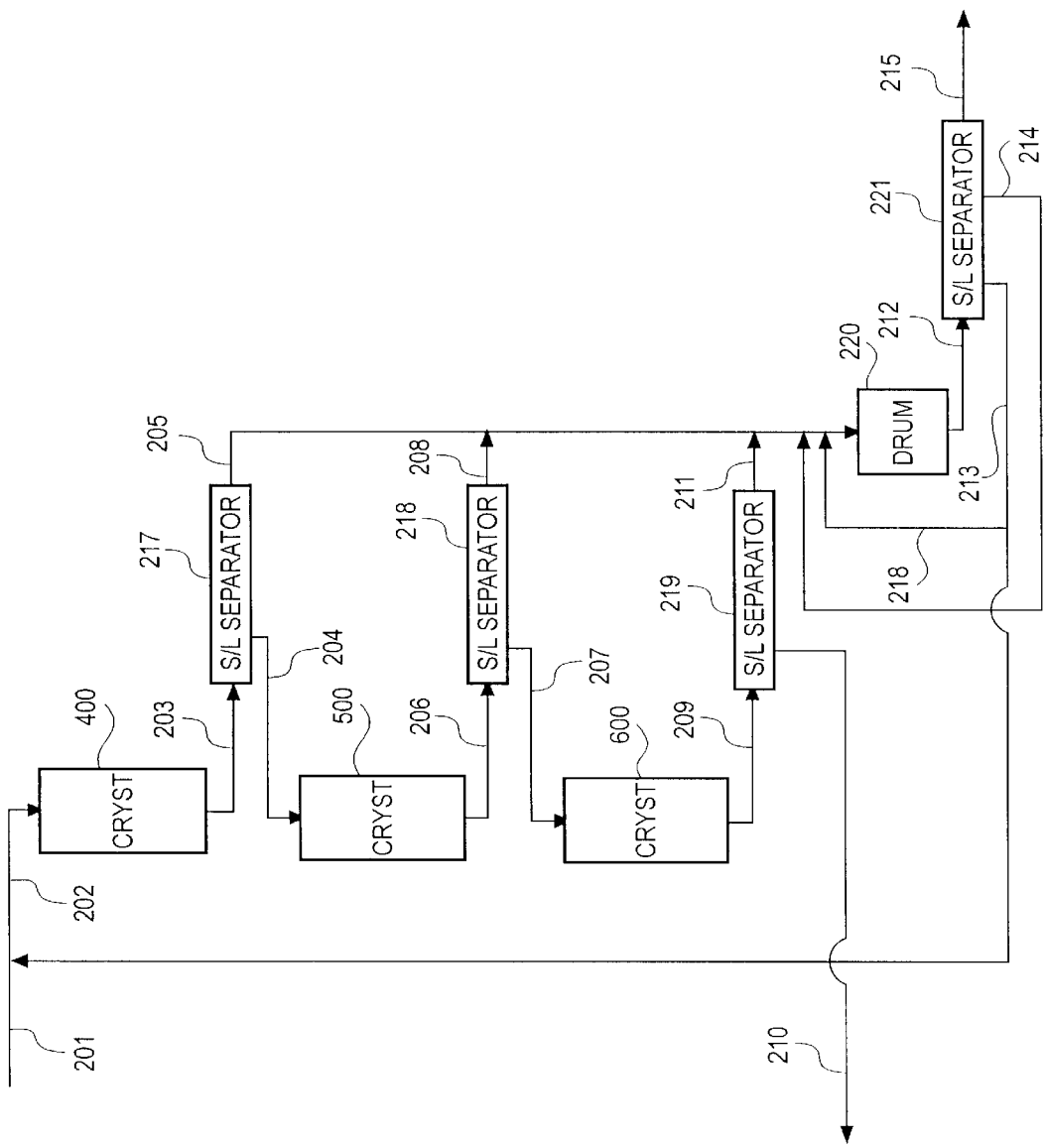
FIG. 9 shows another crystallization process which may be used in combination with PSA in the process of the invention, in which the crystalline para-xylene formed in the first crystallization step does not go to para-xylene product following crystallization and separation but is combined with the crystalline para-xylene cakes formed in the second and third crystallization/separation steps and then subjected to a reslurry step. The crystallizations illustrated in FIGS. 7 and 8 are more preferred than the crystallization illustrated in FIG. 9 because they are more efficient.
Figure 10:
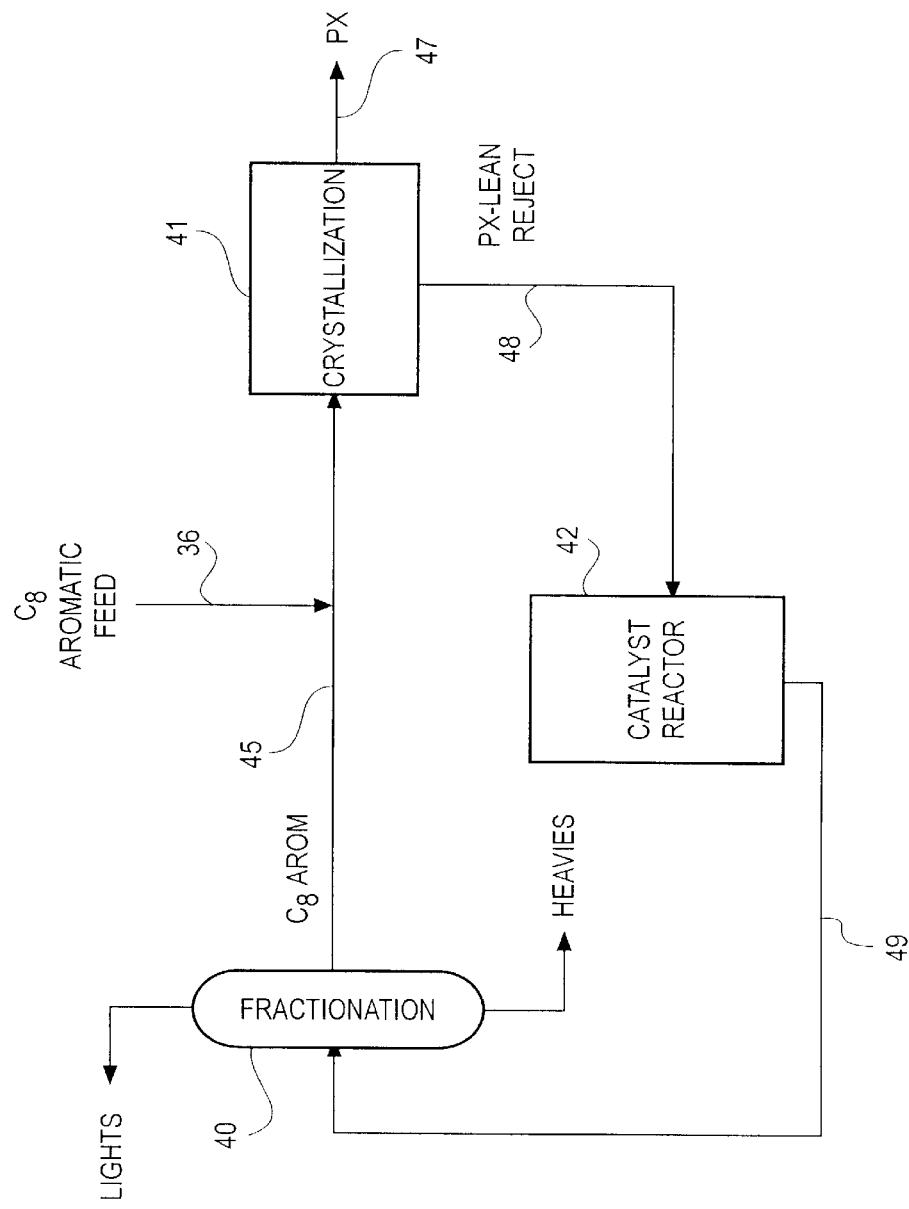
FIG. 10 is a schematic represent ting a state of the art process for producing para-xylene comprising one catalyst reactor and a crystallization unit, such as the processes described in U.S. Pat. Nos. 3,856,873 and 4,163,028.
Figure 11:
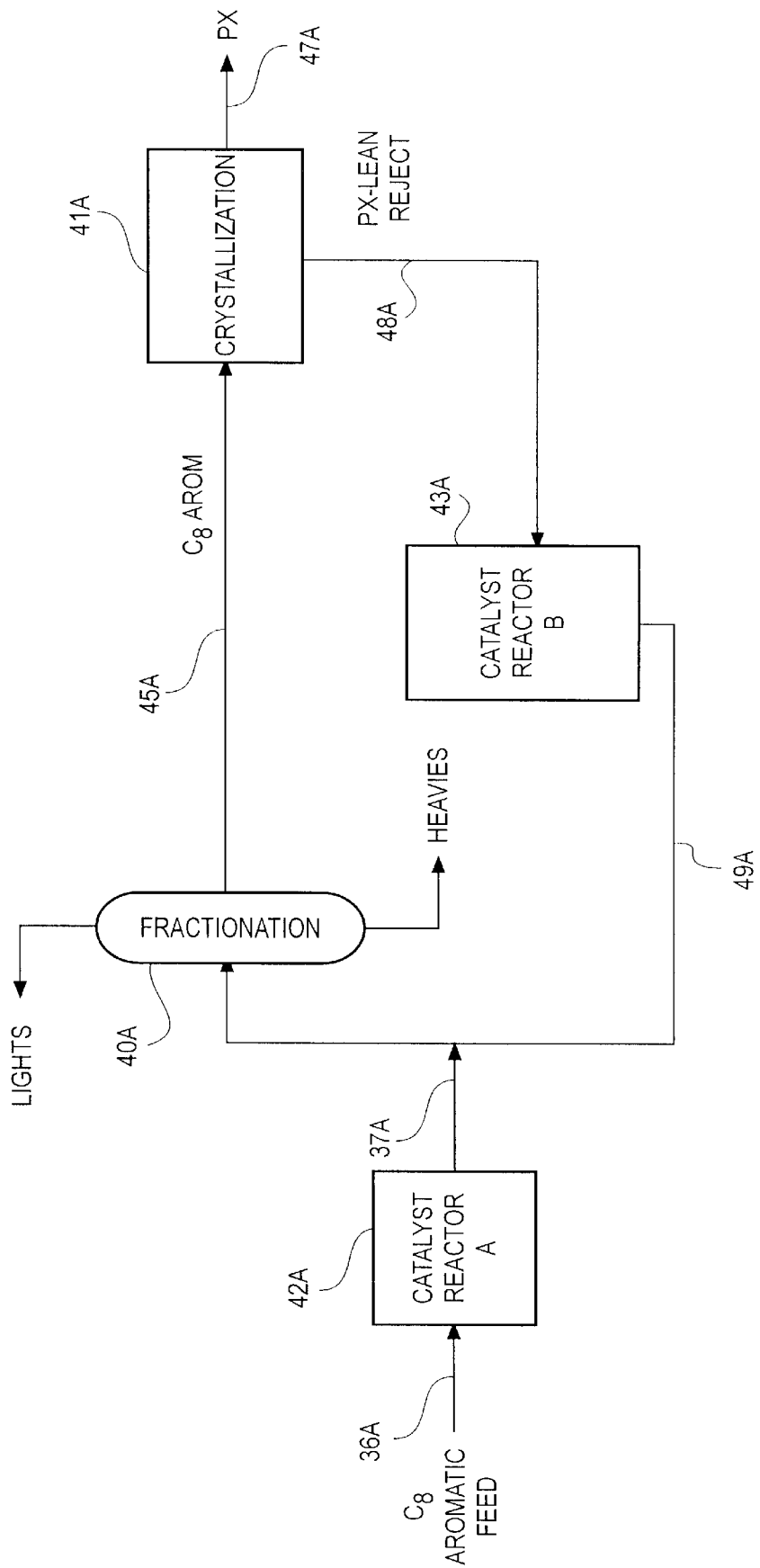
FIG. 11 is a schematic represent ting another state of the art process for producing para-xylene comprising two catalyst reactors and a crystallization unit. U.S. Pat. No. 5,705,726 describes such as process in which the $C_8$ aromatic feed is reacted with a first catalyst in a first reactor under EB conversion conditions, and then reacted with a second catalyst in a second reactor to isomerize the xylenes to equilibrium.

The crystallization component of the process of the invention includes conventional crystallization processes known to those of skill in the art as well as the crystallization processes illustrated in FIGS. 7, 8, and 9.

The components in the meta-xylene/ortho-xylene stream can be further separated to provide high purity, ortho-xylene and meta-xylene products by methods known in the art. The ethylbenzene can also be recovered in highly pure form by methods known in the art.

Figure 12:
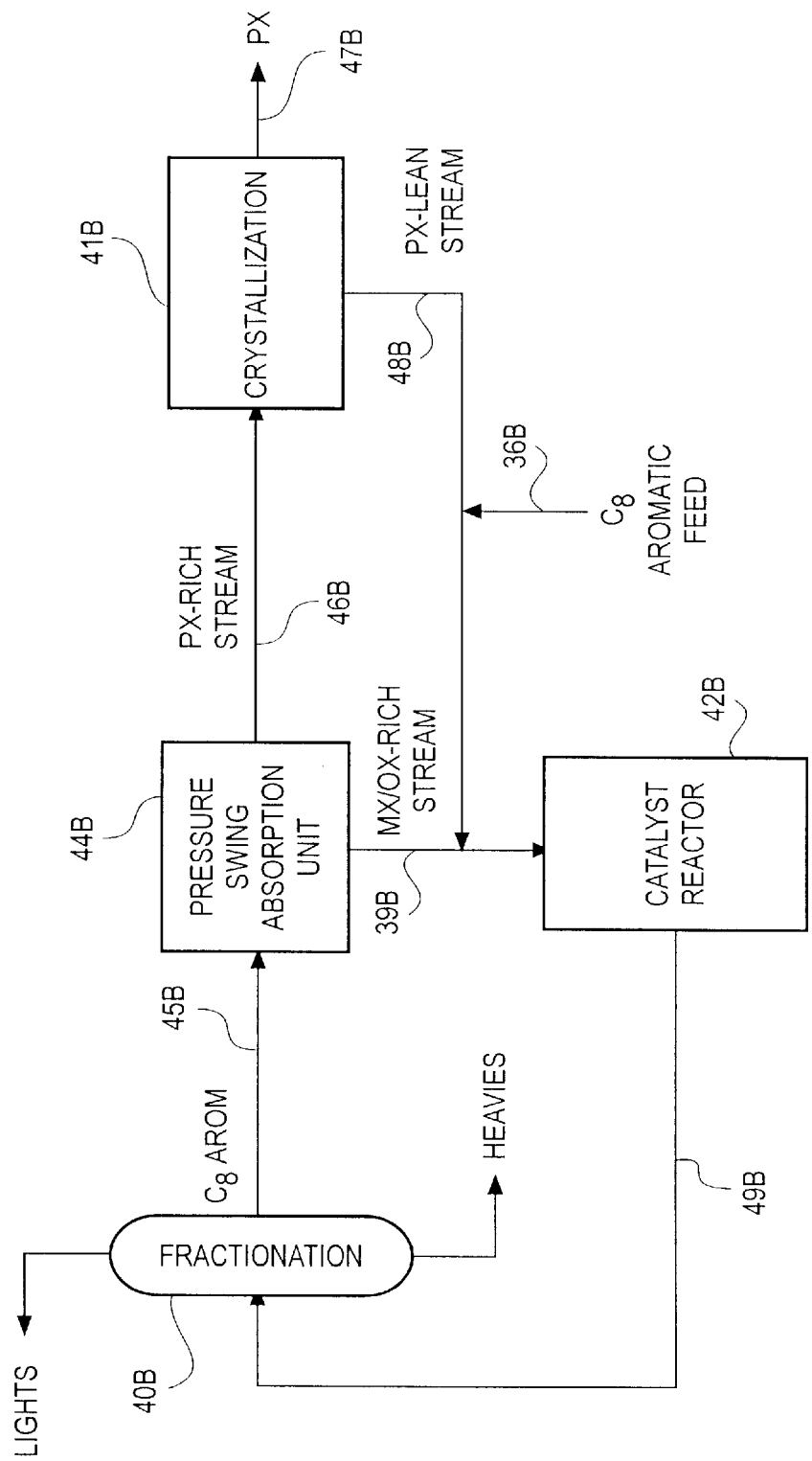
FIG. 12 is a schematic representing one embodiment of the invention comprising a single catalyst reactor, a pressure swing adsorption unit, a fractional distillation section and a crystallization unit to recover para-xylene, wherein the pressure swing adsorption unit is positioned after the fractionation section and before the crystallization unit.

In accordance with the process of the invention as described by an embodiment of the invention illustrated in FIG. 12, the pX-depleted stream in line 48b is recycled to a catalyst reactor 42b, where the xylenes are isomerized to equilibrium and where at least a portion of the ethylbenzene is converted to products which can be separated by fractional distillation from the $C_8$ aromatics. The catalyst or combination of catalysts in the reactor can be any as are suitable for xylene isomerization and ethylbenzene conversion, as known to those skilled in the art. Examples of such catalysts are described by EP 138,617, U.S. Pat. No. 5,001,296, U.S. Re. 31,782, U.S. Pat. No. 4,098,836 and U.S. Pat. No. 4,899,011, all of which are incorporated herein by reference in their entireties. Suitable isomerization conditions include a temperature of about 250° C. to about 500° C., preferably about 340° C. to about 430° C., a pressure of about atmospheric to about 400 psig, preferably in the range of about 100 psig to about 300 psig, a hydrogen to hydrocarbon mole ratio of about 0.5:1 to about 10:1, and a liquid weight hourly space velocity of about 0.5 to about 100 hr−1.

Figure 13:
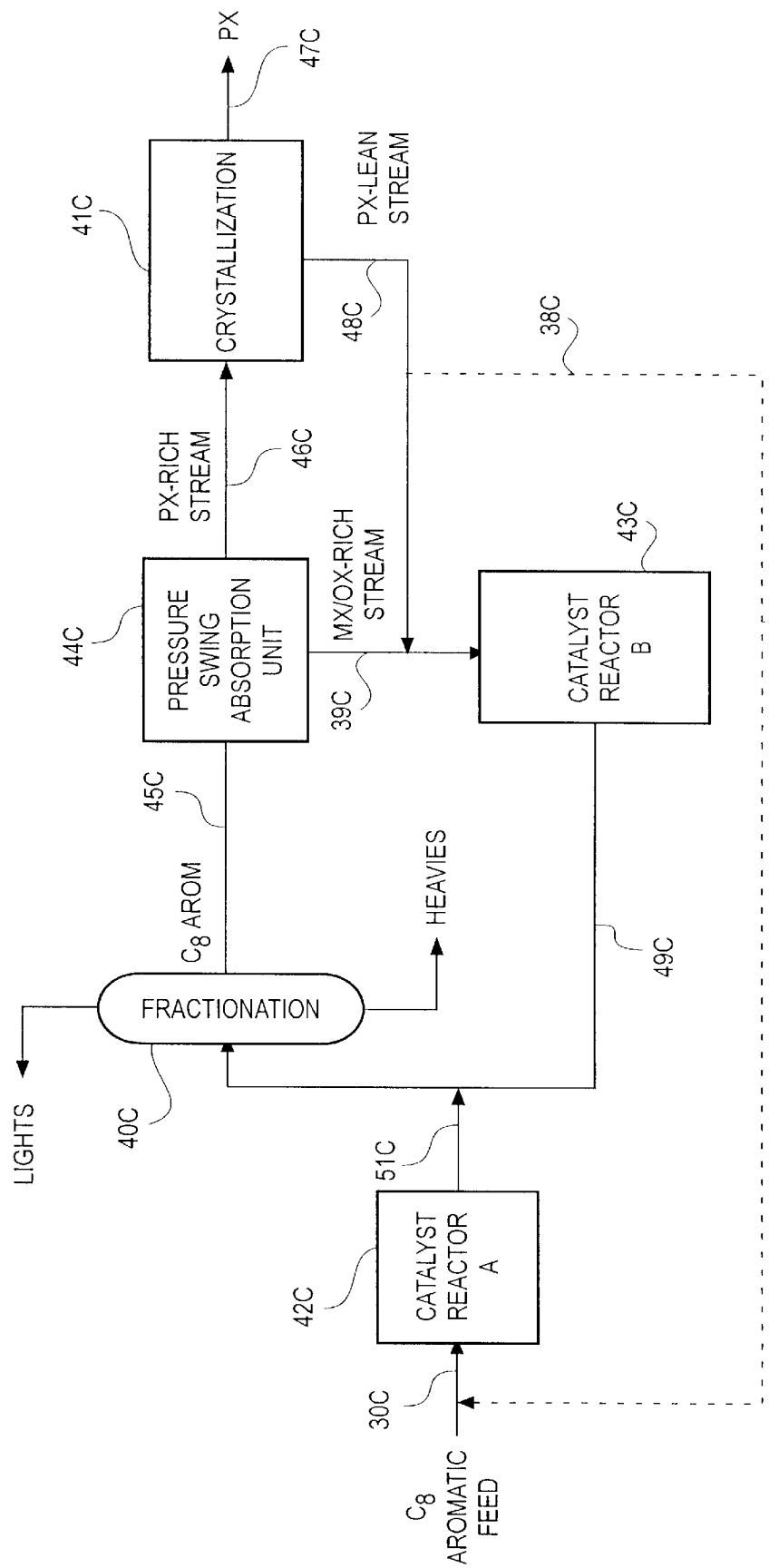
FIG. 13 is a schematic representing another embodiment of the invention comprising a feed pretreater reactor, a fractional distillation section, a pressure swing adsorption unit, a crystallization unit, and a xylene isomerization reactor.
Figure 14:
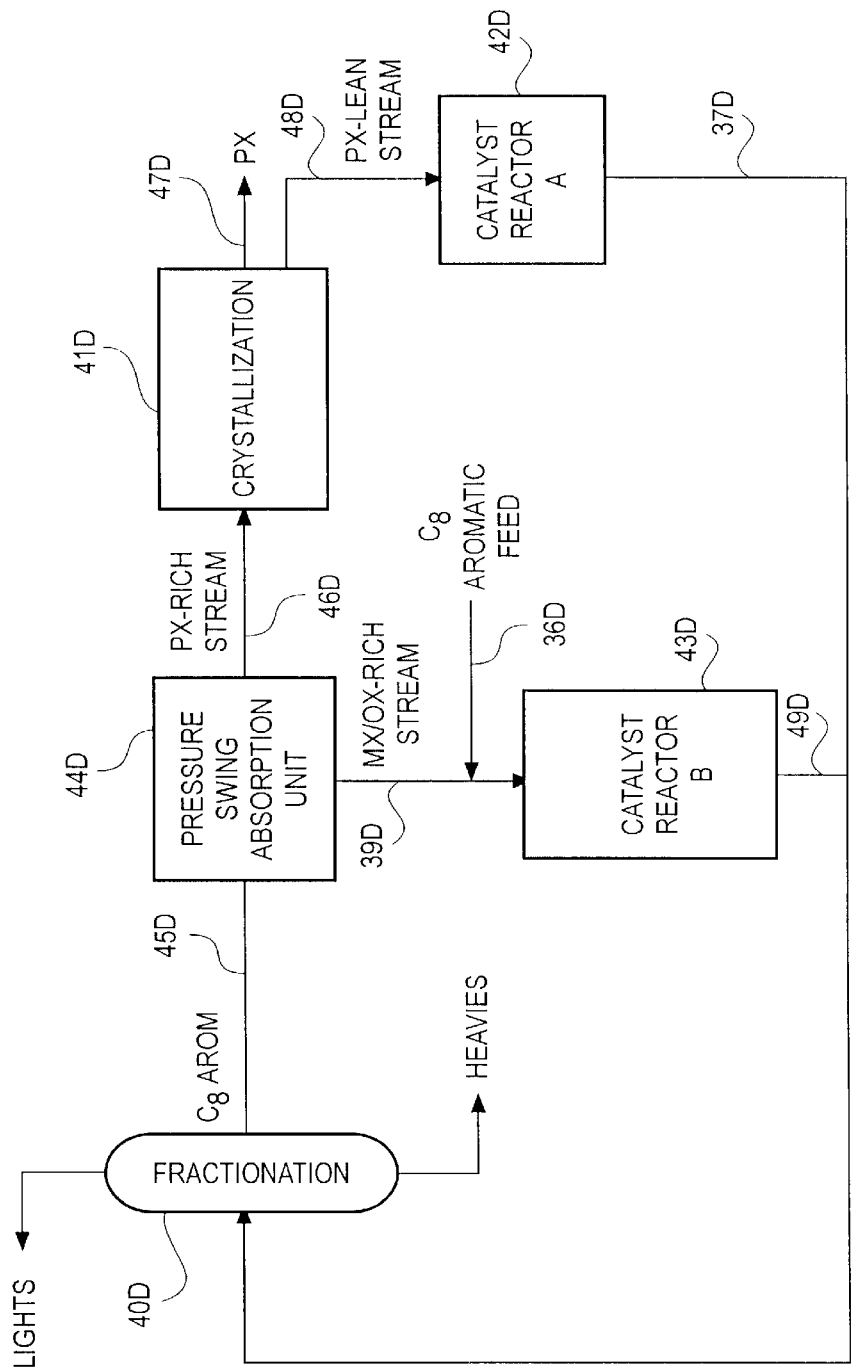
FIG. 14 is a schematic representing another embodiment of the invention comprising a fractional distillation section, a pressure swing adsorption unit, a crystallization unit, and two catalyst reactors, one of which reacts the ethylbenzene containing crystallization reject stream, and a second which isomerizes the xylenes in the pX-lean stream from the pressure swing adsorption unit.

Two other embodiments of the invention, as shown schematically in FIGS. 13 and 14, have two reactors. In FIG. 13, a separate reactor (A) 42c is used to pretreat the $C_8$ aromatic feed 36c to react substantial portions of the ethylbenzene prior to entering the xylene isomerization loop and being sent to the PSA unit. Whereas, in FIG. 14, reactor A 42d reacts a substantial portion of the ethylbenzene in the pX-lean reject stream 48d from the crystallizer 41d. In both schemes, reactor B 43d contains a catalyst system that isomerizes the xylenes to equilibrium. It may also react a portion of the ethylbenzene and the $C_9$ paraffins and naphthenes present.

The catalyst system in reactor A 42d can be any suitable for ethylbenzene dealkylation, hydrodeethylation or hydroisomerization. Examples of catalyst systems for dealkylation are disclosed in Re. 31,782 and U.S. Pat. No. 4,908,342 both of which are incorporated herein by reference in their entireties. Examples of catalyst systems for hydrodeethylation are disclosed in U.S. Pat. Nos. 4,899,011 and 5,367,099, both of which are incorporated herein by reference in their entireties. Examples of catalyst systems for hydroisomerization are disclosed in U.S. Pat. Nos. 5,028,573, 6,150,292 and 5,908,967, all of which are incorporated herein by reference in their entireties. Catalysts systems suitable for reactor B are the same as those described above for the single reactor system.

The present invention includes processes in which pressure swing adsorption is used to produce a para-xylene-enriched feed that is then purified by crystallization using the crystallization processes illustrated in FIG. 7, FIG. 8, and FIG. 9.

Those skilled in the art will recognize that with regard to the concentration of pX, mX, oX, and/or EB in a stream of pX, mX, oX, and/or EB, mole percent equals weight percent.

In the process of the present invention the para-selective adsorbent preferably comprises a para-selective, non-acidic molecular sieve, more preferably a para-selective, non-acidic, medium pore molecular sieve, and more preferably, silicalite. Most preferably, the molecular sieve comprises orthorhombic crystals of silicalite having an average minimum dimension of at least about 0.2 μm.

A para-selective adsorbent is an adsorbent that, when subjected to an equal molar mixture of xylenes at 122° F. (50° C.), adsorbs para-xylene preferentially over meta-xylene and ortho-xylene, such that the total para-xylene in the adsorbate is at least about 75% relative to the total $C_8$ aromatics, preferably greater than 75% relative to the total $C_8$ aromatics; more preferably, at least about 80% relative to the total $C_8$ aromatics; even more preferably, at least about 85% relative to the total $C_8$ aromatics; still more preferably, at least about 90% relative to the total $C_8$ aromatics; and yet more preferably, at least about 95% relative to the total $C_8$ aromatics; and most preferably, at least about 97% relative to the total $C_8$ aromatics.

The adsorbent used in the process of the present invention may comprise a para-selective, non-acidic molecular sieve and a binder. When a molecular sieve and binder are used as the adsorbent, the binder is preferably selected from the group consisting of clay, alumina, silica, titania, zirconia, silica-alumina, silica-magnesia, silica-zirconia, silica-thoria, silica-beryllia, silica-titania, silica-alumina-thoria, silica-alumina-zirconia, silica-alumina-magnesia, silica-magnesia-zirconia, and aluminum phosphate.

Preferably, the adsorbent will contain about 5 to about 100 weight percent molecular sieve.

In the PSA process component of the present invention, it is preferred that at least 0.01 grams of para-xylene is adsorbed per gram of adsorbent, more preferable that at least 0.02 grams of para-xylene is adsorbed per gram of adsorbent, and most preferable that at least 0.03 grams of para-xylene is adsorbed per gram of adsorbent.

The PSA process component of the present invention, is operated at a temperature and pressure sufficient to give rapid adsorption and desorption of para-xylene and/or ethylbenzene. The temperature and pressure conditions are chosen to be able to achieve rapid adsorption/desorption rates and may vary depending upon the particular adsorbent used. Suitable temperature may be selected in ranges of above about 350° F. (176° C.), preferably above about 400° F. (200° C.), and more preferably above about 450°F. (230°C.).

Suitable pressures may be selected in ranges of above about 30 psia (206 kPa), above about 50 psia (345 kPa), and above about 100 psia (690 kPa) with pressures preferably above about 50 psia (345 kPa).

Those skilled in the art will recognize that suitable operating temperatures and pressures for achieving sufficiently rapid adsorption and desorption in the PSA process may vary. For example the temperature and pressure may be in the ranges of about 350° F. (176° C.) to about 750° F. (400° C.) and about 30 psia (200 kPa), to about 400 psia (2760 kPa); more preferably about 400° F. (200° C.) to about 650° F. (350° C.) and about 50 psia (345 kPa) to about 300 psia (2070 kPa); more preferably about 450° F. (225° C.) to about 600° F. (300° C.) and about 50 psia (345 kPa) to about 250 psia (1750 kPa).

In the PSA process component of the present invention, the operating temperature is typically at least about 350° F. (176° C.), preferably at least about 400° F. (200° C.) more preferably at least about 450° F. (230° C.), more preferably at least about 500°F (260° C.), more preferably at least about 550° F. (285° C.). For some embodiments, the temperature may be at least about 600°F (315°C). The operating temperature may range from about 350° F. (176° C.) to about 750° F. (400° C.) preferably from about 450° F. to about 750° F. (about 230° C. to about 400° C.); more preferably from about 500° F. to about 750° F. (about 260° C. to about 400° C.); more preferably, from about 500° F. to about 700° F. (about 260° C. to about 370° C.), more preferably about 550° F. (285° C.) to about 700° F. (370° C.).

In the PSA process component of the present invention, the operating pressure is at least about 30 psia (206 kPa), preferably at least about 50 psia (345 kPa) and may range from about 50 psia (345 kPa) to about 400 psia (2760 kPa). The operating pressure will preferably range from about 30 psia to about 400 psia, more preferably from about 50 psia to about 400 psia, more preferably from about 100 psia to about 400 psia (from about 690 kPa to about 2760 kPa), more preferably from about 150 psia to about 350 psia (from about 1030 kPa to about 2410 kPa). For some embodiments, the pressure may range from about 200 psia to about 300 psia (from about 1380 kPa to about 2070 kPa).

The term "substantially isothermal" means that the only change in temperature of the adsorbent during the PSA cycle is due to the heats of adsorption and desorption.

References to "substantially constant pressure" or "substantially constant operating pressure", mean that during the process referred to there is no depressurization of the adsorption vessel so that it remains at constant pressure; however, those skilled in the art will recognize that there may be some slight variation in pressure due to changes in flows or that the partial pressure of the adsorbed phase may be reduced by an inert purge gas.

A "substantially pure product stream of para-xylene and ethylbenzene" means a stream containing para-xylene and ethylbenzene with less than a total of 25 mole percent, and preferably less than 10 mole percent, and most preferably less than 5 mole percent meta-xylene and ortho-xylene based on total $C_8$ aromatics.

A "substantially pure product stream of ortho-xylene and meta-xylene" means a stream containing ortho-xylene and meta-xylene with less than a total of 5 mole percent, and preferably less than 1 mole percent of para-xylene and ethylbenzene based on total $C_8$ aromatics.

Pure para-xylene is a chemical intermediate useful for the manufacture of terephthalic acid, the major constituent of polyethylene terephthalate. Para-xylene having a purity of at least about 99.5 weight percent, more preferably of at least about 99.7 weight percent, and still more preferably at least about 99.8 weight percent is used to manufacture terephthalic acid by the oxidation of para-xylene.

The present invention relates to a process comprising the use of pressure swing adsorption process for separation of para-xylene (pX) and ethylbenzene (EB) from mixed $C_8$ aromatics using a para-selective adsorbent followed by crystallization of the para-xylene to produce product grade para-xylene of high purity. A high purity para-xylene product will have a purity of at least about 99.5 wt %, more preferably at least about 99.7 wt %, still more preferably at least about 99.8 wt %, and most preferably at least about 99.9 wt %. The process of the invention further includes separation of meta-xylene and ortho-xylene as part of the above PSA process and isomerizing the meta-xylene and ortho-xylene to give an equilibrium mixture of meta-xylene, ortho-xylene, and para-xylene.

For the purpose of this invention, a para-selective adsorbent is defined as a material that, when subjected to an equal molar mixture of $C_8$ aromatics at 50° C., adsorbs pX and EB preferentially over mX and oX, such that the total pX and EB in the adsorbate is at least about 75% relative to the total $C_8$ aromatics.

Preferably, a para-selective adsorbent, when subjected to an equal molar mixture of $C_8$ aromatics at 50° C., will adsorb pX and EB preferentially over mX and oX, such that the total pX and EB in the adsorbate is greater than about 75% relative to the total $C_8$ aromatics.

The preferred adsorbent is a non-acidic, medium pore molecular sieve. A more preferred adsorbent is a non-acidic, molecular sieve of the MFI structure type (same structure as the acidic zeolite ZSM-5 but with the acid sites replaced with neutral moieties so that the molecular sieve is non-catalytic and does not isomerize xylenes). A particularly preferred adsorbent is silicalite. The process is operated in the vapor phase at elevated temperatures and pressures. The pX and EB are substantially adsorbed at high partial pressures while meta-xylene (mX) and ortho-xylene (oX) are not substantially adsorbed. A fixed bed of adsorbent is saturated with pX and EB, wherein the feed to the process is stopped, and then lowering the partial pressure desorbs the pX and EB. The process effluent is rich in pX and EB.

The pressure swing adsorption process is preferably a fixed-bed, batch-wise isothermal process for separation of pX and EB from mX and oX. The separation is based on the selective adsorption of pX and EB into a para-selective adsorbent, such as orthorhombic silicalite crystals having an average minimum dimension of around 0.2 μm or greater, at high pressure and desorption at low pressure. At high pressure, pX and EB are adsorbed, while mX and oX pass through the bed and are essentially not adsorbed producing a substantially pure stream of mX and oX which contains only minor amounts of other substances. The mX and OX may be collected at the outlet of the bed and recycled to an isomerization catalyst to produce more pX or a portion or all may be further separated to produce pure mX and/or pure oX. After saturation of the adsorbent the feed is discontinued and the pX and EB are desorbed by lowering the xylene partial pressure. By operating in the vapor phase at high temperatures, preferably greater than about 350° F. (176° C.) the rates of both adsorption and desorption are fast, minimizing cycle time and reducing the amount of adsorbent and capital expense required for the separation. Use of a non-acidic zeolite or molecular sieve, such as silicalite, eliminates undesirable catalytic reactions of the adsorbed EB and pX, and avoids adsorption of olefins contaminants which reduce the adsorption capacity of the adsorbent.

In the present invention a preferred adsorbent is silicalite molecular sieve, comprising orthorhombic crystals having an average minimum dimension of around 0.2 μm or greater, which has high para-xylene and ethylbenzene selectivity. The para-xylene adsorption capacity of the silicalite adsorbent is at least 1 wt %, and preferably at least 2 wt % and most preferably from about 3 to about 15 wt % at saturation. Adsorbent capacity is typically defined as grams adsorbate (i.e., material adsorbed) divided by grams adsorbent and can also be expressed as a weight percent by multiplying by 100. The process is conducted in the gas phase at a temperature of from about 350° F. to about 750° F. (about 176° C. to about 400° C.) and the unit pressure is about 30 psia to about 400 psia (about 206 kPa to about 2760 kPa).

The present invention uses a pressure swing adsorption process for separation of pX and EB from mixtures of $C_8$ aromatics using a non-acidic, para-selective adsorbent, such as silicalite molecular sieve, comprising orthorhombic crystals having an average minimum dimension of around 0.2 μm or greater. During adsorption, mX and oX are substantially not adsorbed, while pX and EB are substantially adsorbed. The PSA process will preferably operate at about 500° F. to about 750° F. (about 260 to about 400° C.) with pX partial pressures of about 30 to about 150 psia (about 200 to about 1000 kPa), preferably about 40 to about 120 psia (about 265 to about 800 kPa). Selective adsorption of pX and EB (from a feed containing pX, EB, mX and oX) occurs with a silicalite adsorbent, comprising orthorhombic crystals having an average minimum dimension of around 0.2 μm or greater. At elevated temperatures [greater than about 350° F.(176° C.)], adsorption of pX or pX/EB is effected at high partial pressures [greater than about 25 psia (about 170 kPa) partial pressure)]. Subsequently, rapid desorption without catalytic reaction is effected by lowering the partial pressure of the adsorbates. The partial pressure may be decreased by lowering the total pressure in the adsorption vessel or by purging the bed with an inert flow, for example, He, $N_2$, $H_2$, $CH_4$, $CO_2$ etc., while maintaining the unit pressure. The purge gas first displaces the $C_8$ aromatic feed from the non-selective void volume which lowers the partial pressure of para-xylene and ethylbenzene in the adsorption vessel and then sweeps out the adsorbate (substantially para-xylene and ethylbenzene) as it desorbs from the molecular sieve pores.

The present invention uses a pressure swing adsorption process for separation of para-xylene (pX) and ethylbenzene (EB) from meta-xylene (mX) and ortho-xylene (oX). The separation is based on selective adsorption of pX and EB into a non-acidic, silica molecular sieve, having structure type MFI (said material is commonly referred to as silicalite), comprising orthorhombic crystals having an average minimum dimension of around 0.2 μm or greater, at a higher partial pressure, followed by selective desorption (i.e., no isomerization upon desorption) at a lower partial pressure. The process is operated in a batchwise mode by first passing a stream containing a mixture of EB, pX, mX and oX over a fixed bed of silicalite. At high xylene partial pressure, pX and EB are substantially adsorbed, while mX and oX pass through the bed and are substantially not adsorbed. The mX and oX are collected at the outlet of the bed during the adsorption of pX and EB. After saturation of the silicalite, the feed is discontinued and the pX and EB are desorbed by lowering the xylene partial pressure. By operating in the vapor phase at high temperatures [greater than about 350° F.(176° C.)], the rates of both adsorption and desorption are fast minimizing cycle time and reducing the amount of silicalite required for separation. Use of a non-acidic molecular sieve, such as silicalite eliminates undesirable catalytic reactions of the adsorbed EB and pX which occur with H-ZSM-5. Furthermore, non-acidic silicalite is less subject to adsorption of olefin contaminants, which reduce the adsorption capacity of H-ZSM-5.

Non-acidic molecular sieves of the MEL structure type are microporous materials having similar pore size and adsorption capacity to MFI molecular sieves, and as such would be expected to behave similarly. Both MFI and MEL molecular sieves are classified as medium pore molecular sieves. Other molecular sieves that may find use in the present invention are structure types MTW (12 ring structure, e.g., ZSM-12), ATO (12 ring structure, e.g., ALPO-31), NES (10 ring structure, e.g., Nu-87), TON (10 ring structure, e.g., Theta-1, ZSM-22), MTT (10 ring structure, e.g., ZSM-23), FER (10 ring), EUO (10 ring), MFS (10 ring structure, e.g., ZSM-57), AEL (10 ring structure, e.g., ALPO-11), AFO (10 ring structure, e.g., ALPO-41), and SUZ-4 (10 ring structure).

Large pore molecular sieves, such as mordenite, zeolite Beta, and faujasites, and amorphous adsorbents, such as silica, alumina, and clays, are non-selective, and therefore undesirable for use in the present invention, while small pore zeolites, such as zeolite A, are too small to admit pX and EB into the pores.

The adsorbent can be contained in one or more containers or vessels in which separation of a substantially pure stream of mX/oX and a substantially pure stream of pX/EB is effected using programmed flow into and out of the container or vessel. The separation of components taking place in the adsorbent column is a pressure swing adsorption separation wherein the cycle time is defined as the interval of time starting when feed is admitted into the vessel and ending at the time the vessel has been repressurized (i.e., when it is ready for the next addition of feed). Therefore, the cycle time can be described as the time interval at which feed is introduced to the pressurized adsorbent vessel, e.g., every 1 minute, every 5 minutes, every 10 minutes, every 15 minutes, etc. The "cycle" is the complete PSA process (i.e., summation of all the stages). Stages are usually discrete steps in the overall process, such as Feed, Blowdown, Purge, Repressurization; Feed Pressure Equalization, Blowdown, Purge, Repressurization; or Feed, Rinse, Blowdown, Repressurization, etc. However, in some cases the designation of stages can be more arbitrary, such as in the case of a process at constant pressure using a purge gas such as $CH_4$, $CO_2$, He, $H_2$ or $N_2$.

Effluent from the column during each cycle is separated into fractions, or cuts, which may include, for example, (1) a front end cut comprising the unadsorbed components, substantially oX and mX, (2) an intermediate cut comprising a mixture of $C_8$ aromatics where the pX content is greater than the pX content of the feed [i.e., wt % pX (intermediate) >wt % pX (feed)], and (3) a cut comprising the adsorbed components, which is substantially pure pX and EB.

The pressure swing adsorption process is carried out in the vapor phase. Preferred conditions for the process include temperatures from about 450° F. (230° C.) to about 750° F. (400° C.), preferably from about 500° F. (250° C.) to about 750° F. (400° C.), more preferably, from about 600° F. (315° C.) to about 700° F. (370° C.), sufficient to maintain components in the vapor phase at system pressures from about 100 psia (690 kPa) to about 400 psia (2760 kPa), preferably from about 150 psia (1030 kPa) to about 350 psia (2410 kPa), more preferably, from about 200 psia (1380 kPa) to about 300 psia (2070 kPa). The process is conducted at a substantially isothermal temperature.

The pressure swing adsorption (PSA) of the present invention may be conducted in staged cycles. One embodiment of the invention comprises the use of a pressure swing adsorption cycle in which the pressure of the adsorbent vessel is substantially the same throughout the PSA cycle, and removal of the feed from the non-selective void volume and subsequent desorption of pX/EB is accomplished with a gas purge, such as methane hydrogen, nitrogen, or helium. Another embodiment of the invention comprises the use of a four-stage PSA cycle in which a rinse stream of substantially pX/EB is used to displace feed from the non-selective void volume prior to desorption of pX/EB via lowering the absolute pressure of the adsorbent vessel.

A third embodiment of the invention comprises the use of a four-stage PSA cycle in which pX/EB is desorbed by lowering the absolute pressure of the adsorbent vessel, and then is subsequently displaced from the non-selective void volume by a purge stream of substantially mX/oX.

A fourth embodiment of the invention comprises the use of a PSA cycle similar to the third embodiment, with the exception that depressurization occurs in at least two steps, such that gas from depressurization is used to pressurize a regenerated bed (i.e., the cycle contains at least one pressure equalization step).

A fifth embodiment of the invention comprises the use of a PSA cycle employing pressure equalization, a pX/EB rinse step prior to desorption of pX/EB by depressurization, and an mX/oX purge step.

In describing the preferred embodiments of the invention which are illustrated in the drawings, specific terminology will be resorted to for the sake of clarity. However, it is not intended that the invention be limited to the specific terms so selected and it is to be understood that each specific term includes all technical equivalents which operate in a similar manner to accomplish a similar purpose.

Pressure Swing Adsorption Cycle for pX/EB Separation

The pressure swing adsorption process used in the present invention is preferably a fixed-bed, batch-wise substantially isothermal process which can be used to separate para-xylene (pX) and ethylbenzene (EB) from meta-xylene (mX) and ortho-xylene (oX) prior to separation and purification of para-xylene from the pX/EB stream by crystallization. The PSA separation is based on molecular size and consists of the selective adsorption of the smaller $C_8$ aromatics (pX and EB) into a non-acidic, para-selective molecular sieve, such as silicalite, comprising orthorhombic crystals having an average minimum dimension of about 0.2 $\mu$m or greater, while mX and oX pass through the bed and are not adsorbed. The key to a viable commercial process (fast cycles, minimal adsorbent and capital) is operating at a temperature where the desorption rate is high, and consequently, at a pressure giving sufficient adsorption at that temperature. Thus, in the process of the invention, adsorption occurs at high pressure and high temperature; whereas, desorption occurs at low pressure and high temperature. The mX/oX stream may be recycled to the isomerization catalyst producing more pX or it may be further separated to obtain mX and/or oX. The pX/EB stream (rich in pX) is purified via crystallization to give para-xylene having a purity of 99% or greater. Preferably the para-xylene obtained following crystallization will have a purity of at least about 99.5 wt %, more preferably at least about 99.7 wt %, still more preferably at least about 99.8 wt %, and most preferably at least about 99.9 wt %.

Pressure Swing Adsorption Process Specifics

Temperature Range: The temperature range of the PSA process used in the invention is preferably from about 350° F. to about 750° F. (about 175° C. to about 400° C.), preferably from about 450° F. to about 750° F. (about 230° C. to about 400° C.); more preferably from about 500° F. to about 750° F. (about 260° C. to about 400° C.); more preferably, from about 500° F. to about 700° F. (about 260° C. to about 370° C.), more preferably about 550° F. (285° C.) to about 700° F. (about (285° C. to about 370° C.).

The pressure swing adsorption cycle is preferably conducted under substantially isothermal conditions in which the only change in temperature of the adsorbent during the PSA cycle is due to the heats of adsorption and desorption.

High Pressure Side: About 30 to about 420 psig.

Pressure Ratio (High Pressure/Low Pressure): 2–30.

Adsorbent Capacity: About 1 to about 15 wt % at saturation.

The adsorbent may maintain adsorption capacity through many cycles which reduces the need to replace or recondition the adsorbent. This is another cost saving advantage of the process of the present invention.

PSA Process Cycle Designs

In the descriptions that follow pX/EB comprises para-xylene and ethylbenzene and represents the adsorbed phase, which is principally pX and EB, but could also contain other adsorbable components such as benzene, toluene, 1,4-methylethylbenzene, 1,4-diethylbenzene, linear paraffins (typically Co) and mono-methylbranched paraffins (also typically $C_9$). Likewise, mX/oX comprises meta-xylene and ortho-xylene and represents the non-adsorbed phase which is principally mX and oX, but could also contain other non-adsorbable components such as trimethylbenzenes, other isomers of methylethylbenzene and diethylbenzene, cycloparaffins (typically $C_9$) and other sterically bulky components in the feed.

For each embodiment, one complete cycle is described. It is to be understood that practice of the invention involves principally proceeding by repeated said cycles. In the descriptions of the embodiments of the invention, the para-selective adsorbent may be referred to as a molecular sieve; however, it is to be understood that any suitable non-acidic, para-selective adsorbent may be used as the adsorbent.

The preferred embodiments of the PSA process used in the present invention to produce a stream containing at least 50 mole percent para-xylene based on total $C_8$ aromatics are described below.

EMBODIMENT 1

Figure 4:
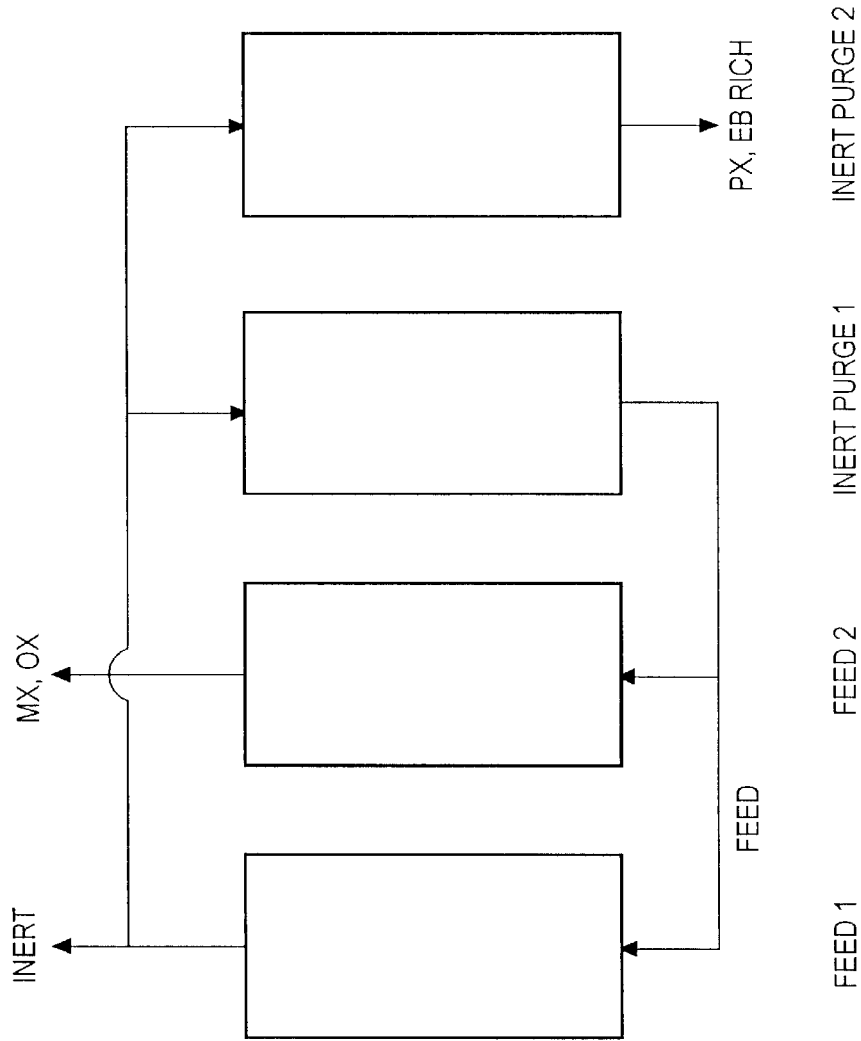
FIG. 4 is a schematic representing an adsorption cycle for pX/EB separation which operates at substantially constant system pressure and uses an inert gas purge, such as, for example, $CH_4$, $CO_2H_2$, $N_2$, or He, to accomplish desorption.

Desorption with Inert Gas Purge, e.g. $CH_4$, $CO_2$, $H_2$, $N_2$, He (FIG. 4)

This embodiment is illustrated in FIG. 4. A typical bed of molecular sieve adsorbent contains about 20–30% of its volume in molecular sieve pores which selectively adsorb pX and EB and 80–70% of void space and large non-selective pores. This embodiment comprises a gas-phase process wherein the temperature is substantially isothermal and the total pressure is substantially constant. The pressure and temperature are selected to allow for rapid adsorption and desorption leading to rapid loading and unloading of the adsorbent bed. Cycle times may be from about 1 to about 30 minutes and are preferably no more than about 25 minutes, more preferably no more than about 20 minutes, still more preferably about 5 to about 15 minutes and most preferably, about 3 to about 15 minutes. Thus a preferred cycle time might be 3, 4, 5, 6, 7, 8, 9, 10, 11, 12, 13, 14, or, 15 minutes. Shorter cycle times are preferred since they reduce the amount of adsorbent and capital required.

Stage 1

Adsorption 1—Displacement of Purge Gas From the Void Space and Initial Adsorption of pX and EB Prior to admitting $C_8$ aromatic feed flow into the adsorbent vessel, the bed is essentially free of $C_8$ aromatics and contains the purge gas. Feed containing a mixture of substantially $C_8$ aromatics (mX, oX, pX, EB), which can also contain some paraffins and naphthenes, $C_9$+ aromatics, benzene and toluene, is passed into the adsorption vessel where pX and EB are adsorbed into the pores of the molecular sieve leaving mX and oX in the void space. As the feed flow continues into the vessel, purge gas is displaced at the outlet of the reactor and recycled to the process.

This stage continues until the purge gas is essentially displaced from the void fraction. (Purge gas may remain in a portion of the molecular sieve pores.) Just prior to hydrocarbon breakthrough, purge gas recovery is discontinued.

Stage 2

Adsorption 2 (Product Collection of mX and oX and Saturation of the Molecular Sieve Pores with pX and EB)

With the removal of purge gas from the void volume, mX and oX exit from the outlet of the adsorption bed as the feed continues to enter the adsorption bed. This mX/oX effluent stream which is substantially free of pX and EB may be collected as one of the product streams for further purification of mX and oX or may be sent to a catalyst reactor for isomerization to an equilibrium xylene mixture.

Throughout this stage pX and EB continue to adsorb into the molecular sieve and mX and oX are displaced from the void fraction by incoming feed. At the end of the stage the void fraction contains feed and the molecular sieve pores contains pX and EB. Collection of the mX and oX is discontinued just prior to breakthrough of the feed.

Stage 3

Desorption of the Feed From the Void Fraction

During the two desorption steps, feed is discontinued and purge gas flows in to the adsorption vessel, typically countercurrent to the flow of $C_8$ aromatics during the feed step. Because the pX and EB are more strongly adsorbed inside the pores of the molecular sieve than the feed in the void fraction, the feed is more readily displaced by the purge gas. As purge gas enters the reactor the feed in the void fraction is removed at the reactor outlet along with a small amount of pX and EB displaced from the molecular sieve. The feed from this stage may be mixed with make-up feed or sent directly to another vessel which is in one of the adsorption stages. Stage 3 is complete when essentially all of the mX and oX have been purged from the vessel.

Stage 4

Collection of pX and EB

Once the feed is displaced from the void fraction, the effluent is highly concentrated in pX and EB. Since the purge gas lowers the partial pressure of pX and EB in the adsorbent vessel, pX and EB continue to desorb from the molecular sieve and exit the adsorbent vessel. This stream is collected for further purification of pX and EB. At the end of this stage the void fraction and molecular sieve pores are essentially filled with purge gas and the system is ready to admit feed flow and begin Stage 1 again.

Figure 3:
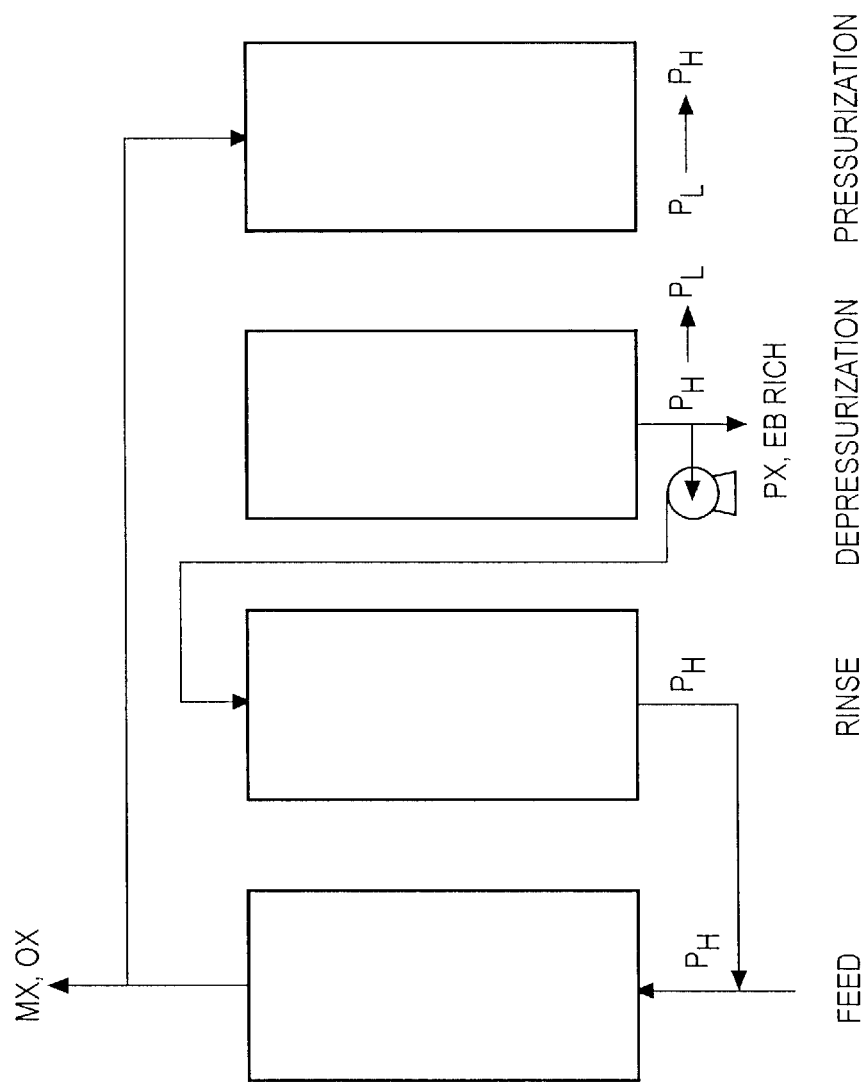
FIG. 3 is a schematic representing a four-stage pressure swing adsorption cycle for pX/EB separation in which a rinse stream of substantially pX/EB is used to displace feed from the non-selective void volume, prior to desorption via lowering of the absolute pressure.

EMBODIMENT 2 pX/EB Rinse Prior to Desorption by Depressurization (FIG. 3)

This process flow is similar to the process embodiment described above except that no $H_2$ (or $CH_4$, $CO_2$ He, $N_2$, etc.) is used during the desorption stages. Rather, removal of the feed from the void fraction is accomplished by rinsing with a stream of substantially pX/EB, and then pX/EB is desorbed from the adsorbent and recovered by depressurizing the adsorption vessel. Again this is a substantially isothermal, gas-phase process with cycle times of about 3 to about 15 min.

Stage 1

Adsorption of pX and EB

Prior to the introduction of $C_8$ aromatic feed, the molecular sieve pore volume is essentially free of pX/EB and the non-selective void volume (i.e., large meso-pores in the adsorbent, interstitial space between adsorbent particles, void space in the adsorbent vessel) is filled with substantially mX/oX. A feed containing substantially $C_8$ aromatics (mX, oX, pX, EB, which can also contain some paraffins and naphthenes, $C_9$+ aromatics, benzene and toluene) then enters the adsorbent vessel and pX/EB begins to adsorb into the molecular sieve pores, and mX/oX in the feed begins to displace the mX/oX that was already in the void volume. The adsorption of pX/EB into the molecular sieve produces a heat front which can be monitored. By the time the pX/EB adsorption front reaches the end of the bed, most of the mX/oX in the void volume has been displaced and replaced with feed (mX, oX, pX, EB). This is the end of the first stage and introduction of feed is stopped just prior to breakthrough.

Stage 2

Displacement of the Feed from the Non-Selective Void Volume

At the end of the first stage, the molecular sieve pores are filled with pX/EB and the non-selective void volume is filled with feed. In order to increase the recovery and purity of pX/EB during the depressurization step, the feed is displaced from the non-selective void space by the addition of a high pressure stream containing substantially pX/EB flowing countercurrent to the $C_8$ aromatic flow during the feed step. The feed displaced during this stage may be sent to another adsorption vessel in Stage 1 of the cycle. Once the feed has been displaced and the non-selective void volume filled with pX/EB, the addition of pX/EB is stopped just prior to pX/EB breakthrough and Stage 2 is complete.

Stage 3

Collection of PX and EB

Once the feed is displaced from the void fraction, the vessel pressure is lowered resulting in desorption of the pX, EB from the molecular sieve. Effluent flow out of the adsorbent bed is typically countercurrent to the $C_8$ aromatic flow, and low pressure pX, EB is collected at the outlet of the adsorption bed for further purification. At the end of this stage the non-selective void volume and molecular sieve pores are filled with a residual amount of pX/EB and the system is ready for repressurization. Prior to repressurization, a low pressure countercurrent flow of mX/oX may be used to displace the remaining pX/EB out of the adsorption vessel.

Stage 4

Repressurization of the Adsorption Vessel

The final step in the cycle is repressurization. Typically, a high pressure stream of mX/oX flowing countercurrent to the $C_8$ aromatic flow during the feed step is used to repressurize the adsorption vessel. Following repressurization, the non-selective void space contains mX/oX and the molecular sieve pores have a residual amount of pX/EB. The system is now ready to admit feed again (Stage 1).

EMBODIMENT 3

Figure 5:
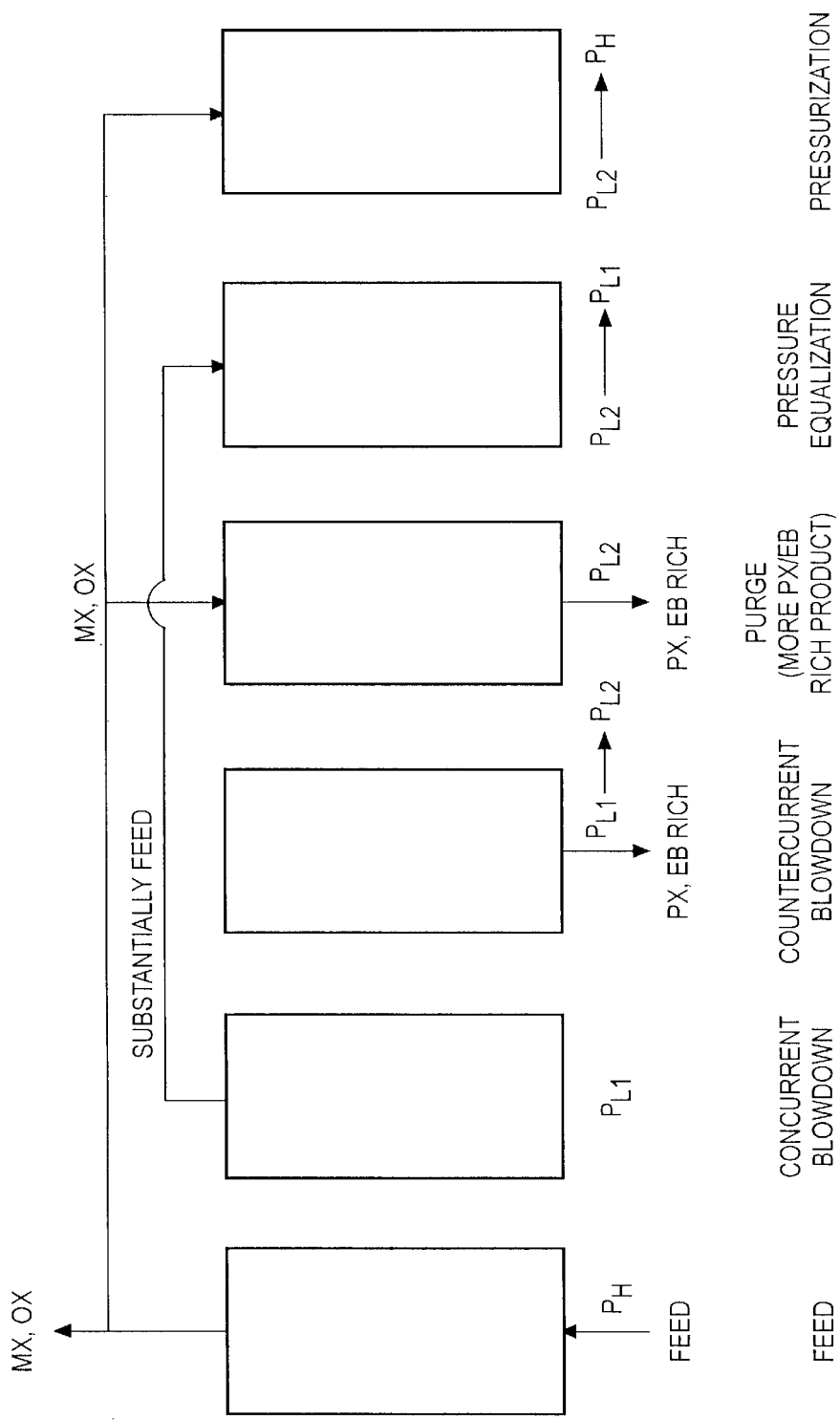
FIG. 5 illustrates a pressure swing adsorption cycle for pX/EB separation similar to that described by FIG. 2, with the exception that depressurization occurs in two steps, such that the gas from the first depressurization is used to pressurize a regenerated bed (i.e., pressure equalization).

Pressure Equalization Prior to pX/EB Product Collection (FIG. 5)

This embodiment of the invention comprises a five-stage PSA cycle in which pX/EB is desorbed by lowering the absolute pressure of the adsorbent vessel in at least two steps, and then subsequently displaced from the non-selective void volume by a purge stream of substantially mX/oX.

Stage 1

Adsorption of pX and EB

In the first stage, the molecular sieve pore volume is essentially free of pX/EB and the non-selective voids (i.e., large meso-pores in the adsorbent, interstitial space between adsorbent particles, and void space in the adsorbent vessel) are filled with substantially mX/oX. A feed containing substantially $C_8$ aromatics (mX, oX, pX, EB, which may also contain some paraffins and naphthenes, $C_9$+ aromatics, benzene and toluene) then enters the adsorbent vessel and pX/EB begins to adsorb into the molecular sieve pores, and mX/oX in the feed begins to displace the mX/oX that was already in the void volume. The adsorption of pX/EB into the molecular sieve produces a heat front which can be monitored. By the time the pX/EB adsorption front reaches the end of the bed, most of the mX/oX in the void volume has been displaced and replaced with feed (mX, oX, pX, EB). This displaced mX/oX effluent stream which is substantially free of pX and EB is collected as one of the product streams for further purification of mX and oX or may be sent to a catalyst reactor for isomerization to an equilibrium xylene mixture. Introduction of feed is stopped just prior to breakthrough, and this completes Stage 1.

Stage 2

Pressure Equalization

In order to increase the purity of the pX/EB product stream collected in the subsequent stage and to conserve mechanical energy, an initial pressure reduction in the vessel takes place. The vessel is depressurized to a lower pressure ($P_{L1}$) by cocurrent blowdown and equalizing of pressure with another adsorbent bed at a lower pressure ($P_{L2}$). During this step, the feed in the non-selective void volume degasses first, resulting in a higher concentration of pX/EB in the adsorbent vessel. The second absorbent vessel is pressurized with the degassing material such that its pressure increases (from $P_{L2}$ to $P_{L1}$), such that at the end of this stage the pressure in the two vessels is equalized at $P_{L1}$).

Stage 3

Recovery of the PX/EB Stream

Following pressure equalization, the adsorbent vessel is further depressurized (e.g., via countercurrent blowdown). The purity of the exiting stream increases in pX/EB during the blowdown process, such that a stream containing substantially pX/EB (based on total $C_8$ aromatics) can be obtained. At the end of Stage 3, the non-selective void volume contains substantially pX/EB and the pressure in the vessel is $P_{L2}$.

Stage 4

Removal of pX/EB in the Non-selective Void Space

Additional pX/EB can be collected from the adsorbent vessel by displacing the pX/EB in the non-selective void space. This is typically done using a stream of substantially mX/oX, although feed can also be used. At the end of Stage 4, most of the pX/EB has been removed from the non-selective void volume and replaced with mX/oX. The pressure remains at $P_{L2}$. An adsorbent vessel in this state is used for the second adsorbent vessel in the pressure equalization step (Stage 2), such that the pressure increases from $P_{L2}$ to $P_{L1}$.

Stage 5

Repressurization to $P_H$

The final step in the cycle is to repressure the vessel from $P_{L1}$ to $P_H$ using a stream of substantially mX/oX typically flowing countercurrently to the flow during the feed stage. Thus, at the end of the cycle, the molecular sieve pore volume is essentially free of pX/EB and the non-selective void volume contains mX/oX. The vessel is now ready to begin the cycle again (i.e., Stage 1: adsorption of pX/EB from the feed.)

EMBODIMENT 4

Figure 2:
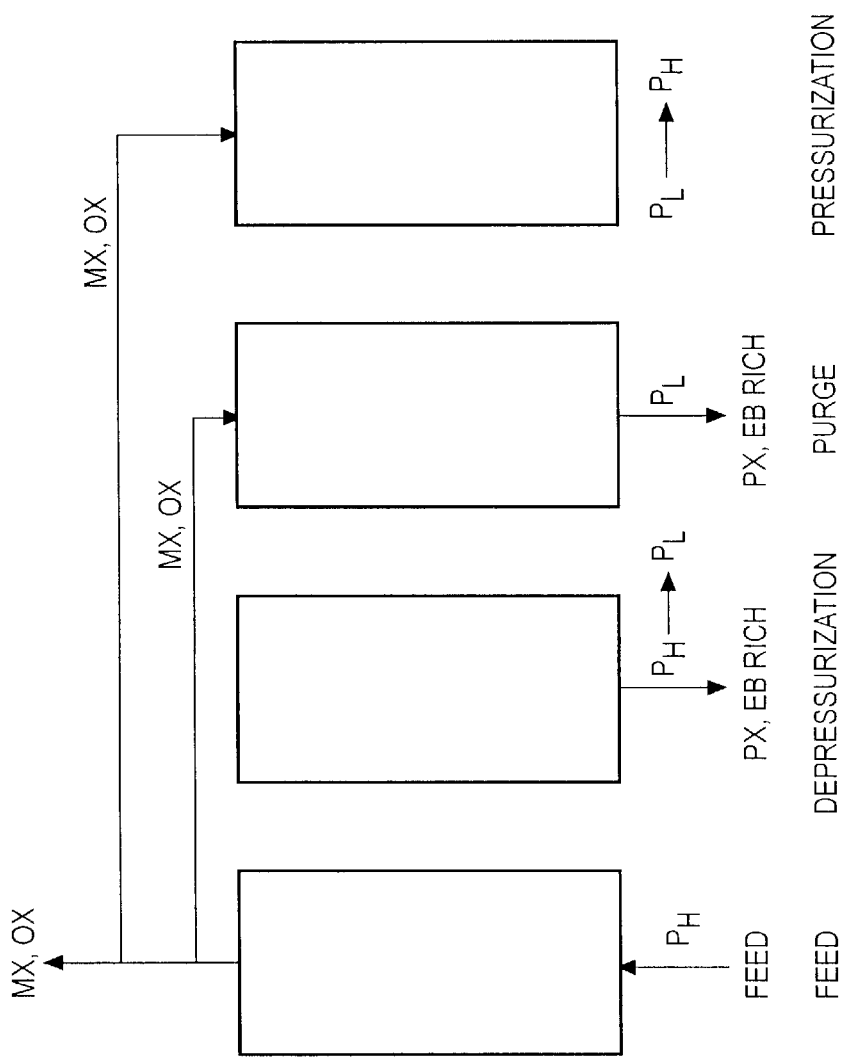
FIG. 2 is a schematic representing a four-stage pressure swing adsorption cycle for pX/EB separation in which pX/EB is desorbed by lowering the absolute pressure, and then subsequently displaced by a purge stream of substantially mX/oX.

Simple 4-Stage Cycle with Purge (FIG. 2)

This cycle (shown in FIG. 2) is basically the same as Embodiment 3, except depressurization occurs in one step with no pressure equalization.

EMBODIMENT 5

Pressure Equalization Prior to Rinse

This cycle is basically the same as Embodiment 3 except prior to the countercurrent blowdown step, a pX/EB rinse is used to displace the mX/oX-rich material in the void space.

Crystallization

The PSA process is integrated with crystallization to produce high purity para-xylene. Any of the known crystallization methods may be integrated with the PSA process of the invention to give a high purity para-xylene product having a purity of at least about 99.5 wt %.

Examples of crystallization processes which could be used as the crystallization component of the PSA-crystallization process of the present invention are disclosed in U.S. Pat. Nos. 2,985,694; 3,177,265; 3,467,724; 3,662,013; 3,916,018; 3,729,523; 5,284,992; 5,329,060; 5,448,055; 5,922,924; 6,111,161; and 6,147,272 all of which are incorporated herein by reference in their entireties.

Crystallization may be conducted in several crystallization stages by passing a para-xylene-containing mixture into a crystallizer operated at a temperature sufficient to induce crystallization of para-xylene, typically from about 0° F. to about −80° F.(about −18° C. to about −62° F., removing the mixture from the crystallizer, separating the para-xylene and passing the mother liquor to a second stage for further cooling and the recovery of additional para-xylene. The resulting mother liquor may then be sent to a distillation stage to recover and ethylbenzene in the mixture. Stages crystallization using a series of crystallizers usually provides optimum results. Typically, in a continuous process the bottoms from the distillation are continuously recycled to the crystallization stage for the recovery of additional para-xylene.

In a two-stage crystallization, the first stage may use several crystallizers in series. I the first crystallizer stage should be at a temperature which allows para-xylene crystals to form with out crystallizing other components in the mixture, typically this may be about −50° C. to about −70° C. (−58° F. to about −94° F.). Effluent from the crystallizer is separated into para-xylene crystals and mother liquor. Typically, at least a portion of the mother liquor is recycled to an isomerization unit and isomerized to produce an equilibrium mixture of xylenes. The crystallized para-xylene from the first stage can be melted and sent to a second crystallization stage wherein the operating conditions are similar to that of the first crystallization stage with the exception that the crystallization temperature is higher, typically about −10° C. (about 14° F.). The para-xylene crystals from the second stage typically have a higher purity that those from the first crystallization stage. The crystalline para-xylene from the second crystallization may be treated further to increase the para-xylene purity by washing it with high purity para-xylene product to remove adhering second stage mother liquor. Other solvents, such as toluene, n-pentane, and aqueous alcohols may be used as the wash liquid; however, they have the disadvantage of requiring an additional distillation step to remove the wash solvent from the para-xylene product.

The PSA process can produce effluent streams having a para-xylene concentration of at least about 40 wt %, more preferably at least about 45 wt %, more preferably at least about 50 wt %, more preferably at least about 55 wt %, more preferably at least about 60 wt %, more preferably at least about 65 wt %, more preferably at least about 70 wt %, more preferably at least about 75 wt %, more preferably at least about 80 wt %, more preferably at least about 85 wt %, more preferably at least about 90 wt %, more preferably at least about 95 wt %, and more preferably at least about 97 wt % which can be fed to a crystallization unit to produce high purity para-xylene.

Crystallization processes which take advantage of the ability of the PSA process to produce effluent streams of $C_8$ aromatics having enriched para-xylene concentrations are particularly suitable for integration with the PSA process.

As stated above, crystallization processes are known for isolating a concentrate of crystalline para-xylene from a para-xylene-containing stream such as that produced in the PSA component of the present invention. One such process comprises cooling the mixture until para-xylene crystallizes from the mixture. The crystallization of para-xylene from such mixtures typically requires temperatures as low as −100° F. to maximize the recovery of para-xylene. However, the exact temperature will depend on the composition of the mixture of xylenes. Processes for crystallizing para-xylene from such mixtures are described, for example, in U.S. Pat. Nos. 2,866,833 and 3,177,265, incorporated herein by reference in their entireties. In these processes one or more crystallizers, such as a scraped wall crystallizer, are used, each at progressively lower temperatures. For example, the first crystallizer may operate at a temperature of −50° F. to about −60° F., the second at about −65° F. to about −80° F., and the third at about −85° F. to about −95° F. The mixture exiting the final crystallizer is a mixture of mother liquor and solid enriched in crystalline para-xylene. The mother liquor is enriched in ortho- and meta-xylene. The mixture exiting the last crystallizer is separated in a suitable separation apparatus operated at a temperature sufficiently low to maintain the crystalline para-xylene in the crystalline state. Solid para-xylene, i.e., the cake, isolated from the separation apparatus is typically about 80 to about 95 weight percent para-xylene. The impurities are due to the mother liquor adhering to the para-xylene crystals and/or due to impurities contained within the crystal structure of the crystalline para-xylene. When the purity of crystalline para-xylene is referred to in describing this crystallization process, it accounts for impurities adhering to the outside of the crystals and/or impurities contained within the para-xylene crystals. Such impure crystalline para-xylene can be used to prepare pure crystalline para-xylene.

Since the mother liquor separated from the crystalline para-xylene is enriched in meta-xylene and ortho-xylene, it is advantageous to direct it to a xylene isomerization unit wherein a mixture of xylenes having a less than equilibrium amount of para-xylene is contacted with a suitable catalyst to isomerize the xylenes to a mixture containing an equilibrium mixture of the xylenes. Processes for isomerizing a mixture of xylenes containing less than an equilibrium amount of para-xylene to an equilibrium mixture are disclosed, for example, in U.S. Pat. No. 4,269,813.

A slurry process can be used to obtain very pure para-xylene from impure crystalline para-xylene. Impure crystalline para-xylene having a purity of less than about 99.7 weight percent, for example, para-xylene having a purity of about 80 to less than about 99.7 weight percent, can be purified to crystalline para-xylene having a purity of at least about 99.7 weight percent, preferably at least about 99.8 weight percent, and most preferably at least about 99.85 weight percent para-xylene, by contacting the impure crystalline para-xylene in the form of a slurry with a liquid containing para-xylene at a temperature of at least 32° F., preferably about 35° F. to about 45° F., more preferably at a temperature of about 37° F. to about 44° F., and most preferably at a temperature of about 39° F. to about 42° F., for a time sufficient to increase the purity of the crystalline para-xylene to at least about 99.7 weight percent, more preferably at least about 99.8 weight percent, and most preferably at least about 99.85 weight percent para-xylene. It is necessary to use these temperatures for the slurry in order to obtain the desired very high purity para-xylene. When operated as a continuous process, the residence time of the slurry of crystalline para-xylene and liquid para-xylene in the vessel used for containing the slurry is suitably about 0.2 to about 2 hours, more preferably about 0.25 to about 0.5 hour. The amount of liquid in the slurry should be an amount to produce a mixture that can be slurried and pumped. For example, the slurry can be about 30 to about 60 weight percent solids with the remainder being the liquid portion of the slurry. More preferably, the slurry is about 40 to about 50 weight percent solids. This liquid used for the slurry is a liquid containing para-xylene. The amount of para-xylene in the liquid is an amount suitable for providing for the slurry of crystalline para-xylene and liquid at the temperature used for the slurry. Preferably, the liquid para-xylene used to prepare the slurry is about 70 to about 85 weight percent para-xylene. The remainder of the liquid is typically a mixture of ortho- and meta-xylene, ethylbenzene and minor amounts of other hydrocarbons present in the process. After the desired purity of crystalline para-xylene is achieved, the purified crystalline para-xylene is separated from the liquid and preferably washed with liquid para-xylene to remove adhering mother liquor. The liquid para-xylene used for the wash is preferably high purity para-xylene having a purity of at least about 99.7 weight percent, more preferably at least about 99.8 weight percent. The weight ratio of liquid para-xylene wash to crystalline para-xylene is typically about 0.05:1 to 0.5:1, more preferably 0.15:1 to 0.25:1. Upon melting the purified crystalline para-xylene, a liquid product para-xylene having a purity of at least 99.7 weight percent, more preferably at least about 99.8 weight percent, and most preferably at least about 99.85 weight percent para-xylene is produced.

In one embodiment of this crystallization process, one slurry stage is used and one recrystallization stage is used (each followed by a separation step) to obtain the high purity para-xylene. In this embodiment, impure crystalline para-xylene having a purity of about 85 to about 95 weight percent (i.e., having impurities adhering to the outside of the para-xylene crystals and/or within the crystal structure) is slurried with para-xylene containing liquid in a suitable vessel at a temperature of about −20° F. to about 20° F., more preferably about −10° F. to about 10° F. The amount of crystalline para-xylene in the slurry is typically about 30 to about 60 weight percent, preferably about 35 to about 45 weight percent. The slurry is suitably stirred by a mechanical agitator and the slurry is retained in the slurry vessel for a time sufficient to produce a crystalline para-xylene having an increased purity relative to the impure crystalline para-xylene fed to the slurry vessel. For the preferred continuous operation of the process of this invention, the residence time for the slurry in the slurry vessel is suitably about 0.2 to about 2 hours, preferably about 0.5 to about 1 hour. The para-xylene containing liquid used for the slurry, for example, can be para-xylene obtained from melting the impure crystalline para-xylene, it can be one or more filtrates or wash streams used in one or both of the separation steps, or it can be any combination of these sources of para-xylene.

The para-xylene-containing liquid used to prepare the aforementioned slurry of crystalline para-xylene and liquid para-xylene can be supplied from any convenient source, and can be from within or outside of the process. For example, such liquid can be obtained by simply melting a portion of the crystalline para-xylene used for the slurry, or it can be one or more of the mother liquor streams produced by separating the crystalline para-xylene from liquid mother liquor. The para-xylene-containing liquid used for the slurry is an amount suitable for providing for the slurry of crystalline para-xylene and liquid at the temperature used for the slurry. For example, the para-xylene containing liquid used for the slurry can be about 70 to about 85 weight percent para-xylene. Typically, the remainder is a mixture of ortho- and meta-xylene, ethylbenzene and other hydrocarbons from the process.

The slurry from the slurry vessel is directed to a first separation apparatus, such as, for example, a centrifuge, a filter or a settling vessel. Preferably, the first separator apparatus is a centrifuge, more preferably a pusher centrifuge. A portion of the filtrate produced by the separation process can be directed to the slurry vessel. This filtrate stream can be heated or cooled, as necessary, to obtain the desired temperature in the slurry vessel. Filtrate can also be returned to a crystallizer used to separate para-xylene from a mixture of ortho-, meta- and para-xylene. Solid para-xylene produced by the first separation apparatus, having a purity typically of about 94 to about 98 weight percent, is directed to a first melt tank where the solid, intermediate purity para-xylene is melted to liquid para-xylene. The melt is sent to a crystallizer to recrystallize the para-xylene. The crystallizer can be a scraped wall crystallizer, or any other suitable crystallizer apparatus known to those skilled in the art. The para-xylene in the crystallizer is suitably cooled to a temperature of about 20° F. to about 45° F. to crystallize the para-xylene, more preferably to a temperature of about 35° F. to about 40° F. The mixture of crystallized para-xylene and mother liquor is sent to a second separation apparatus, preferably a pusher centrifuge, where the solid, purified para-xylene is separated from the crystallization mother liquor. Reject filtrate from this separation apparatus can be directed to the slurry vessel as a slurry liquid and/or it can be directed to the crystallizer. The crystalline para-xylene separated in the second separation apparatus can be washed with liquid para-xylene to increase its purity. Liquid para-xylene used for the wash can be high purity para-xylene produced by this process, liquid from the first melt tank, or a combination of these two sources. The ratio of wash liquid to crystalline para-xylene is suitably about 0.05:1 to about 0.5:1 by weight, more preferably about 0.15:1 to about 0.25:1 by weight. When a pusher centrifuge is used as a second separation apparatus, the washing of the solid para-xylene can be accomplished in the pusher centrifuge. Wash filtrate from the second separation apparatus can be directed to the crystallization apparatus and/or to the slurry vessel. Pure crystalline para-xylene, having a purity of at least 99.7%, more preferably 99.8% by weight is removed from the second separation apparatus, melted in a second melt tank and sent to storage.

In another embodiment of this crystallization process, two slurry stages are used to obtain the high purity para-xylene, each with a slurry vessel and a separation apparatus. In this embodiment, impure crystalline para-xylene having a purity of about 80 to about 95 weight percent, preferably of about 85 to about 90 weight percent is slurried with para-xylene containing liquid in a first slurry vessel suitably at a temperature of about −20° F. to about 20° F., more preferably about −10° F. to about 10° F. The amount of crystalline para-xylene in the slurry is typically about 20 to about 60 weight percent, preferably about 30 to about 50 weight percent. This slurry is preferably agitated, preferably by a mechanical agitator. The slurry is retained in the slurry vessel for a time sufficient to produce a crystalline para-xylene having an intermediate purity. For the preferred continuous operation of this embodiment of the invention, the residence time for this slurry in the slurry vessel is suitably about 0.2 to about 2 hours, more preferably about 0.5 to about 1 hour. The para-xylene-containing liquid used for the first slurry can be para-xylene obtained from melting the impure crystalline para-xylene, it can be one or more reject filtrate or wash filtrate streams produced in one or both of the separation steps in this embodiment, or it can be any combination of one or more of these sources of para-xylene.

Slurry from the first slurry vessel is directed to a first separation apparatus such as, for example, a centrifuge, a filter, a settling vessel or the like. Preferably, the first separation apparatus is a centrifuge, more preferably a pusher centrifuge. Some of the filtrate produced by the separation process can be directed to the slurry vessel to produce the slurry and the filtrate can be heated or cooled, as necessary, to obtain the desired slurry temperature. At least a portion of the filtrate can be sent to a crystallizer used to separate para-xylene from an equilibrium mixture of ortho-, meta- and para-xylene.

Solid para-xylene, i.e., the cake, produced by the first separation apparatus, typically having a purity of about 94 to about 98 weight percent, is directed to a second slurry vessel where it is slurried with para-xylene-containing liquid at a temperature of suitably at least about 30° F., preferably about 35° F. to about 45° F., more preferably at a temperature of about 38° F. to 42° F. The para-xylene-containing liquid used to slurry the crystalline para-xylene in the second slurry vessel can be from the same sources of para-xylene used for the first slurry vessel in this embodiment. The amount of crystalline para-xylene in the slurry is typically about 30 to about 60 weight percent, more preferably about 40 to about 50 weight percent, and most preferably about 45 to about 55 weight percent. As with the first slurry, it is preferable to stir or mix the slurry by, for example, a suitable mechanical agitator apparatus. The slurry is maintained in the second slurry vessel for a time sufficient to increase the purity of the crystalline para-xylene contained therein. For the preferred continuous processes of this invention, the residence time for the slurry in the second slurry vessel is suitably about 0.2 to about 2 hours, more preferably about 0.5 to about 1 hour.

The slurry from the second slurry vessel is directed to a second separation apparatus, such as a centrifuge, filter, settling tank or the like. Preferably, it is a centrifuge, more preferably a pusher centrifuge. Reject filtrate from the second separation apparatus can be directed to the first and/or second slurry vessel to be used as the para-xylene-containing slurry liquid. This reject filtrate stream can be heated or cooled prior to being added to the slurry vessels in order to maintain the slurry vessel at the proper temperature. The crystalline para-xylene produced by the second separation apparatus is preferably washed with high purity liquid para-xylene. The ratio of wash to crystalline para-xylene is suitably about 0.05:1 to about 0.5:1 by weight, more preferably about 0.15:1 to about 0.25:1 by weight. A preferable source of para-xylene for the washing of the purified crystalline para-xylene from the second separation apparatus is the purified liquid para-xylene product produced by the process. Wash filtrate from the second separation step can also be used as wash for the crystalline para-xylene separated in the second separation apparatus. The wash filtrate can also be directed to the first and second slurry vessels.

Solid, purified para-xylene exits the second separation apparatus. Para-xylene having a purity of at least 99.7% by weight, preferably at least about 99.8% by weight, can be achieved by this embodiment.

In another crystallization embodiment, a recrystallization step is used in combination with a slurry step, and purified para-xylene is produced in the slurry step. In this embodiment, impure para-xylene, typically having a purity of about 85 to about 90 weight percent para-xylene, is slurried with para-xylene-containing liquid in a suitable vessel at a temperature and for a time sufficient to purify the impure crystalline para-xylene. The temperature of the slurry is suitably at least about 30° F., preferably about 35° F. to about 45° F., more preferably at a temperature of about 38° F. to 42° F. The amount of crystalline para-xylene in the slurry is typically about 30 to about 60 weight percent, more preferably about 40 to about 50 weight percent, and most preferably about 45 to about 55 weight percent. As with the first slurry, it is preferable to stir or mix the slurry by, for example, a suitable mechanical agitator apparatus. For the preferred continuous processes of this invention, the residence time for the slurry in the slurry vessel is suitably about 0.2 to about 2 hours, more preferably about 0.5 to about 1 hour.

The slurry from the slurry vessel is directed to a first separation apparatus, such as a centrifuge, filter, settling tank or the like. Preferably, it is a centrifuge, more preferably a pusher centrifuge. In the first separation apparatus, purified crystalline para-xylene is separated from mother liquor. Crystalline para-xylene produced by the first separation apparatus is preferably washed with high purity liquid para-xylene. The ratio of wash to crystalline para-xylene is suitably about 0.05:1 to about 0.5:1 by weight, more preferably about 0.15:1 to about 0.25:1 by weight. A preferable source of para-xylene for the washing of the purified crystalline para-xylene from the second separation apparatus is the purified liquid para-xylene product produced by the process. Purified crystalline para-xylene exiting the first separation apparatus is typically melted and can be sent to storage.

In this embodiment, filtrate from the first separation apparatus is directed to and crystallized in a suitable crystallization apparatus, which can be a scraped wall crystallizer or any other suitable crystallizer known to those skilled in the art. Liquid filtrate sent to the crystallizer is cooled to a temperature of abut −70° F. to abut 25° F., preferably to a temperature of about −20° F. to about 20° F. to crystallize para-xylene contained therein and form a mixture comprising crystallized para-xylene and mother liquor which is then directed to a second separation apparatus, preferably a centrifuge, more preferably a pusher centrifuge, where the solid, crystalline para-xylene is separated from the mother liquor and sent to the slurry vessel. Optionally, all or part of such crystalline para-xylene can be melted prior to adding it to the slurry vessel. Filtrate from the second apparatus can be directed to the source of the impure para-xylene used in this embodiment such as, for example, low temperature crystallizers used to isolate a para-xylene concentrate from an equilibrium mixture of xylenes. At least a part of the filtrate from the second separation apparatus can also be directed to the crystallizer apparatus used for crystallizing the filtrate from the first separation apparatus. Also in this embodiment, at least a portion of filtrate from the first separation apparatus can be directed to the slurry vessel used to form the slurry. Additionally, at least a portion of the wash filtrate from the first separation apparatus can also be directed to the slurry vessel.

Crystallization processes which take advantage of the ability of the PSA process to produce effluent streams of $C_8$ aromatics having enriched para-xylene concentrations are particularly suitable for integration with pressure swing adsorption in the process of the present invention.

The following are embodiments of the present invention comprising a process for the production of high purity para-xylene integrating PSA with a novel crystallization process which crystallizes the para-xylene-enriched effluent stream from a PSA unit to give high purity para-xylene. The crystallization process used has an advantage over other crystallization processes. It reduces the refrigeration requirements compared to designs disclosed in U.S. Pat. Nos. 6,111,161 and 5,448,005. Thus it requires less energy expenditure and provides a cost savings. It accomplishes this by separating some or most of the final product early in the separation sequence thereby reducing the amount of material that requires lower temperature refrigeration. It does not recycle cake back to the first crystallizer from the lower temperature stage(s), but rather uses a reslurry drum to sufficiently warm the crystals so that additional para-xylene product can be recovered without the need for more refrigeration. As calculated according to standard engineering practices, the refrigeration compressor horsepower for the invention can be as much as 13% less than that for comparable designs based on the teachings of U.S. Pat. No. 6,111,161.

In one embodiment of the present invention a feedstream comprising $C_8$ aromatic hydrocarbons is fed to a pressure swing adsorption unit to produce a para-xylene-enriched feedstream having a para-xylene concentration of at least about 60 weight percent, which is fed to a crystallization unit and subjected to crystallization to produce high purity para-xylene by a crystallization process comprising:

a) crystallizing said feedstream in a first crystallizer at a temperature of from about 10° F. to about 55° F.;

b) recovering an effluent comprising para-xylene crystals in a mother liquor;

c) separating the para-xylene crystals from the mother liquor in a first separation unit, washing the para-xylene crystals with liquid para-xylene, completely melting the para-xylene crystals, and collecting the liquid para-xylene product;

d) transferring at least a portion of filtrate from the first separation unit to a second crystallizer which is operated at a temperature lower than that of the first crystallizer, crystallizing the filtrate, and recovering an effluent comprising para-xylene crystals in a mother liquor;

e) separating the para-xylene crystals from the mother liquor in a second separation unit and sending the para-xylene crystals to a slurry apparatus;

f) transferring at least a portion of filtrate from the second separation unit to a third crystallizer, which is operated at a temperature lower than that of the second crystallizer, crystallizing the filtrate, and recovering an effluent comprising para-xylene crystals in a mother liquor;

g) separating the para-xylene crystals from the mother liquor in a third separation unit and sending the para-xylene crystals to the slurry apparatus;

h) contacting the para-xylene crystals in the slurry apparatus with para-xylene-containing liquid to form a slurry mixture having a temperature higher than that of the lowest temperature crystallizer;

i) separating the slurry mixture in a fourth separation unit to produce a filtrate and a crystalline para-xylene product, washing the para-xylene crystals with liquid para-xylene, completely melting the para-xylene crystals, and collecting the liquid para-xylene product;

j) recycling at least a portion of filtrate from the fourth separation unit to the second crystallizer; and k) recycling at least another portion of filtrate selected from the group consisting of filtrate from the first separation unit, filtrate from the fourth separation unit, and filtrate from the first and fourth separation units to the slurry apparatus.

Preferably, the crystalline para-xylene product from step (c) is combined with the crystalline para-xylene product from step (i) prior to melting. This can be suitably accomplished by sending the two para-xylene products to the same melt drum.

The crystallization in step (a) of the above embodiment is preferably conducted at a temperature of from about 30° F. to about 55° F., and more preferably at a temperature of from about 35° F. to about 45° F.

The second crystallizer in step (d) of the above embodiment is preferably operated at a temperature of from about −10° F. to about 35° F., more preferably at a temperature of from about 15° F. to about 25° F.

The third crystallizer in step (f) of the above embodiment is preferably operated at a temperature of from about −35° F. to about 5° F., more preferably at a temperature of from about −10° F. to about −5° F.

The slurry mixture in step (h) of the above embodiment preferably has a temperature of from about 10° F. to about 55° F., more preferably about 30° F. to about 50° F., more preferably about 35° F. to about 45° F., more preferably about 38° F. to about 42° F., and most preferably about 40° F. to about 42°.

In one embodiment of the above PSA-crystallization process the crystallization in step (a) is conducted at a temperature of from about 10° F. to about 55° F., the second crystallizer in step (d) is operated at a temperature of from about −10° F. to about 35° F., the third crystallizer in step (f) is operated at a temperature of from about −35° F. to about 5° F.; and the slurry mixture in step (h) has a temperature of from about 10° F. to about 55° F.

In another embodiment of the above PSA-crystallization process of the invention, the crystallization in step (a) is conducted at a temperature of from about 30° F. to about 55° F., the second crystallizer in step (d) is operated at a temperature of from about 15° F. to about 25° F., the third crystallizer in step (f) is operated at a temperature of from about 10° F. to about −5° F.; and the slurry mixture in step (h) has a temperature of from about 30° F. to about 50° F.

Preferably the slurry mixture in step (h) of the above PSA-crystallization process will comprise about 30 to about 60 weight percent crystalline para-xylene, more preferably 30 to about 50 weight percent crystalline para-xylene, and more preferably 35 to about 50 weight percent crystalline para-xylene.

Under appropriate conditions the amount of para-xylene crystals in the slurry mixture formed in the slurry apparatus may be greater than the amount of para-xylene crystals sent to the slurry apparatus.

In another embodiment of the present invention a feedstream comprising $C_8$ aromatic hydrocarbons is fed to a pressure swing adsorption unit to produce a para-xylene-enriched feedstream having a para-xylene concentration of at least about 55 weight percent, which is fed to a crystallization unit and subjected to crystallization to produce high purity para-xylene by a crystallization process comprising:

a) crystallizing said feedstream in a first crystallizer at a temperature of from about 10° F. to about 55° F.;

b) recovering an effluent comprising para-xylene crystals in a mother liquor;

c) separating the para-xylene crystals from the mother liquor in a first separation unit, washing the para-xylene crystals with liquid para-xylene, completely melting the para-xylene crystals, and collecting the liquid para-xylene product;

d) transferring at least a portion of filtrate from the first separation unit to a second crystallizer which is operated at a temperature lower than that of the first crystallizer, crystallizing the filtrate, and recovering an effluent comprising para-xylene crystals in a mother liquor;

e) separating the para-xylene crystals from the mother liquor in a second separation unit and sending the para-xylene crystals to a slurry apparatus;

f) transferring at least a portion of filtrate from the second separation unit to a third crystallizer, which is operated at a temperature lower than that of the second crystallizer, crystallizing the filtrate, and recovering an effluent comprising para-xylene crystals in a mother liquor;

g) separating the para-xylene crystals from the mother liquor in a third separation unit and sending the para-xylene crystals to the slurry apparatus;

h) contacting the para-xylene crystals in the slurry apparatus with para-xylene-containing liquid to form a slurry mixture having a temperature higher than that of the lowest temperature crystallizer;

i) separating the slurry mixture in a fourth separation unit to produce a filtrate and a crystalline para-xylene product, washing the para-xylene crystals with liquid para-xylene, completely melting the para-xylene crystals, and collecting the liquid para-xylene product;

j) recycling at least a portion of filtrate from the fourth separation unit to the first crystallizer; and k) recycling at least another portion of filtrate selected from the group consisting of filtrate from the first separation unit, filtrate from the fourth separation unit, and filtrate from the first and fourth separation units to the slurry apparatus.

In the above embodiment, the crystalline para-xylene product produced in step (c) is conveniently combined with the crystalline para-xylene product produced in step (i) in a melt drum or other suitable melting means and melted to give a high purity liquid para-xylene product.

The crystallization in step (a) of the above embodiment is preferably conducted at a temperature of from about 30° F. to about 55° F., and more preferably at a temperature of from about 35° F. to about 45° F.

The second crystallizer in step (d) of the above embodiment is preferably operated at a temperature of from about −10° F. to about 35° F., more preferably at a temperature of from about 5° F. to about 15° F.

The third crystallizer in step (f) of the above embodiment is preferably operated at a temperature of from about −35° F. to about 5° F., more preferably at a temperature of from about −10° F. to about −5° F.

The slurry mixture in step (h) of the above embodiment preferably has a temperature of from about 10° F. to about 55° F., more preferably about 30° F. to about 50° F., more preferably about, more preferably about 35° F. to about 45° F., more preferably about 38° F. to about 42° F., and most preferably about 40° F. to about 42° F.

In one embodiment of the above PSA-crystallization process the crystallization in step (a) is conducted at a temperature of from about 10° F. to about 55° F., the second crystallizer in step (d) is operated at a temperature of from about 10° F. to about 35° F., the third crystallizer in step (f) is operated at a temperature of from about −35° F. to about 5° F.; and the slurry mixture in step (h) has a temperature of from about 10° F. to about 55° F.

In another embodiment of the above PSA-crystallization process of the invention, the crystallization in step (a) is conducted at a temperature of from about 20° F. to about 30° F., the second crystallizer in step (d) is operated at a temperature of from about 5° F. to about 15° F., the third crystallizer in step (f) is operated at a temperature of from about −10° F. to about −5° F.; and the slurry mixture in step (h) has a temperature of from about 30° F. to about 50° F.

Preferably the slurry mixture in step (h) of the above PSA-crystallization process will comprise about 30 to about 60 weight percent crystalline para-xylene, more preferably 30 to about 50 weight percent crystalline para-xylene, and more preferably 35 to about 50 weight percent crystalline para-xylene.

Under appropriate conditions the amount of para-xylene crystals in the slurry mixture formed in the slurry apparatus may be greater than the amount of para-xylene crystals sent to the slurry apparatus.

In the above PSA-crystallization embodiments of the invention, a portion of the high purity liquid para-xylene product is preferably used to wash the crystalline para-xylene obtained in steps (c) and (i). The ratio of wash to crystalline para-xylene is suitably about 0.05:1 to about 0.5:1 by weight, more preferably about 0.15:1 to about 0.25:1 by weight. A preferable source of para-xylene for the washing of the purified crystalline para-xylene is the purified liquid para-xylene product produced by the process of this invention.

The slurry mixture formed by mixing the para-xylene crystals obtained from the second and third crystallizations with para-xylene-containing liquid may also be referred to as a reslurry mixture since the para-xylene crystals will have come out of the second and third crystallizers in a slurry with mother liquor prior to separation and are being contacted with para-xylene-containing liquid in a slurry vessel or slurry apparatus to form another slurry. It is preferable to stir or mix the slurry mixture with, for example, a suitable mechanical agitator apparatus. The slurry mixture is maintained in the slurry apparatus (which may also be referred to as a slurry vessel or reslurry drum) for a time sufficient to increase the purity of the crystalline para-xylene contained therein to the desired purity. For the preferred continuous process of this invention, the residence time for the slurry in the slurry vessel is typically about 0.2 to about 2 hours, more preferably about 0.5 to about 1 hour.

Para-xylene produced in the process of the invention has a purity of about 99.5 wt % para-xylene or greater, preferably about 99.7 wt % para-xylene or greater; most preferably about 99.8 wt % para-xylene or greater.

The above-described novel crystallization process is an energy efficient crystallization process for recovering a high purity para-xylene product from a feedstream comprising para-xylene in a concentration greater than that found in equilibrium mixtures of $C_8$ aromatics. In the present invention, the para-xylene-enriched feedstream to be crystallized is produced via pressure swing adsorption and then sent to the crystallization unit. Preferably, the para-xylene-enriched feedstream will comprise at least about 60 weight percent para-xylene. The para-xylene-enriched feedstream may also comprise other $C_7$ to $C_9$ aromatic compounds, including ortho-xylene, meta-xylene, and ethylbenzene. The novel crystallization process which is integrated with PSA to produce high purity para-xylene is based on two concepts which together provide an advantage over other known processes. The first concept centers on the first stage of crystallization and separation. By the appropriate choice of process conditions and equipment, the first stage is capable of producing high purity product that does not require further processing. This improves efficiency and cost effectiveness compared to other crystallization processes which recycle and recrystallize the para-xylene before obtaining the final product. The second concept centers on the use of reslurry technology to warm all of the crystalline para-xylene cake that is too cold to conveniently yield high purity para-xylene product directly but most importantly, requires no refrigeration and, therefore, reduces energy requirements and cost. A reslurry drum is used to warm the para-xylene crystals that are obtained from low temperature crystallizers that are too cold to make para-xylene product directly or conveniently. If the para-xylene crystals are too cold, the para-xylene wash used to displace the impure mother liquor in the cake will freeze and not penetrate the cake.

The crystallization process can be used in combination with any process that yields a stream containing at least about 60 weight percent (wt %) para-xylene, preferably greater than about 60 wt % para-xylene, more preferably at least about 70 wt % para-xylene, more preferably at least about 75 wt % para-xylene, more preferably at least about 80 wt % para-xylene, more preferably at least about 85 wt % para-xylene, more preferably at least about 90 wt % para-xylene, and most preferably at least about 95 wt % para-xylene, to produce a high purity para-xylene product. In one embodiment of the invention, the feedstream can contain at least about 55 wt % para-xylene.

An embodiment of the novel crystallization process step is illustrated in FIG. 7. In the following discussions, when referring to the drawings, the stream number corresponds to the number of the line in which the stream is transported. A para-xylene-containing feed is passed through line 1 to at least one high temperature crystallizer 100 where it is cooled to a temperature sufficient to crystallize para-xylene without crystallizing meta-xylene and ortho-xylene. Preferably the feed in line 1 (stream 1) will comprise at least about 60 wt % para-xylene. Stream 1 may be obtained from any appropriate source which can produce a feed containing about 60 wt % para-xylene. For example, it could come from an adsorption process such as a HYSORB™ unit made by UOP; it could come from a pressure swing adsorption (PSA) unit; it could come from a reaction process such as a toluene disproportionation (TDP) unit, or it could come from another crystallization process such as a low temperature crystallization stage. Various feeds having the same or different para-xylene compositions can also be combined to provide the feed for the process of the present invention. It is desirable that the composition of stream 1 be at least about 60 weight percent para-xylene, preferably greater than about 60 wt % para-xylene, more preferably at least about 70 wt % para-xylene, more preferably at least about 75 wt % para-xylene, more preferably at least about 80 wt % para-xylene, more preferably at least about 85 wt % para-xylene, more preferably at least about 90 wt % para-xylene, more preferably greater than about 90 wt % para-xylene, still more preferably at least about 95 wt % para-xylene.

A $C_8$ aromatic stream comprising at least about 60 wt % para-xylene (stream 1) is fed via line 1 to a high temperature crystallizer 100 which is at a temperature of about 10° F. to about 55° F., preferably from about 30° F. to about 55° F. producing an effluent in line 2 (stream 2) comprising a slurry of para-xylene crystals and mother liquor which is conveyed via line 2 to a liquid-solid separation unit 30 which is operated at a temperature sufficiently low to maintain the crystalline para-xylene in the crystalline state. No refrigeration is needed to maintain this operating temperature. The conditions of stream 2 will vary depending on the composition of stream 1. For an embodiment in which stream 1 contains about 90 wt % para-xylene, the temperature of the effluent stream (stream 2) in line 2 may be about 40° F. In the present invention, the crystallizers are preferably all operated at about atmospheric pressure; however, by this is meant that sufficient pressure is maintained inside the crystallizer to prevent the entry of air in the event of a leak. Therefore, in operation, the crystallizer chamber will usually be maintained at slightly above atmospheric pressure. This is less costly than operating under pressure which requires thicker walls and stronger flanges to handle the increased pressure.

The crystallizer 100 to which the $C_8$ aromatic stream 1 is fed can comprise various numbers and types of crystallization devices in various sequences as is known to those skilled in the art. For example, a single crystallization device can be used or multiple units may be used. If multiple units are used, the crystallization vessels can be arranged in parallel, in series, or in other more complex configurations. There are various types of crystallization devices available such as draft tube crystallizers and scraped wall crystallizers. The type of crystallizer used is not critical. The refrigeration can be supplied indirectly wherein the refrigeration does not mix with the process material. Typical examples include jackets surrounding the crystallization vessel or shell and tube heat exchanges external to the crystallization vessel. Propylene is a preferred refrigerant. Alternatively, the refrigeration can be supplied directly wherein the refrigeration, by design, is mixed with the process material. Typical examples include the injection of cold carbon dioxide or cold nitrogen into a draft tube crystallizer. Typical residence times in the crystallizers are in the range of about 30 minutes to about 5 hours, preferably about 30 minutes to about 3 hours, more preferably about 0.5 to about 2 hours.

Although not shown in FIG. 7, an alternate embodiment of the process in which either or both of two types of recycle streams are incorporated into the crystallization designs could be used to improve operability. The first recycle stream would recycle a portion of the crystallizer effluent back to the crystallizer 100. This could be represented in FIG. 7 by sending a portion of the slurry effluent in line 2 back to crystallizer 100. The second recycle stream would recycle a portion of one or more of the filtrate streams from the liquid-solid separation unit 30 immediately downstream of the crystallizer 100. This could be represented in FIG. 7 by sending at least a portion of the filtrate effluent in line 3 and/or line 4 back to crystallizer 100.

As shown in FIG. 7, an effluent stream from crystallizer 100 comprising a slurry of para-xylene crystals and mother liquor is conveyed through line 2 to a separation unit 30 comprising one or more liquid/solid separation devices. In a preferred embodiment, the liquid/solid separator 30 comprises one or more centrifuges which are used to separate para-xylene crystals from the mother liquor. Centrifuges used as separators in the process of the invention can be scraped bowl centrifuges or pusher centrifuges or a combination thereof. Other liquid/solid separation devices such as wash columns, or rotary filters, could also be used for separating para-xylene crystals in the process. Wash columns which could be used are, for example, NIRO wash columns or TNO hydraulic wash columns such as those described in U.S. Pat. Nos. 4,734,102 and 4,735,781 incorporated herein by reference in their entireties.

When all of the liquid/solid separators are centrifuges, it is preferable to use an initial feed containing a higher concentration of para-xylene, for example, at least about 80 wt % para-xylene, preferably at least about 85 wt % para-xylene, more preferably at least about 90 wt % para-xylene. When the temperature of the crystalline para-xylene slurry to be separated is below about 37° F., it is preferable to use wash columns to do the separation or, if using centrifuges, to wash with a solvent such as toluene. However, using toluene or another solvent rather than high purity para-xylene as the wash liquid, will require an additional distillation step and additional equipment to separate the toluene from the para-xylene product which may increase the cost of the process.

When the liquid-solid separation device 30 is a centrifuge, it yields a product stream of washed para-xylene crystals. This para-xylene product stream is sent to a melt drum 35 via line 5 where the para-xylene crystals are completely melted to provide a high purity liquid para-xylene product. A portion of this high purity para-xylene is removed from melt drum 35 as product through product collection line 16 without further processing, i.e., without going through an additional cycle of crystallization and centrifugation. Taking a portion of the para-xylene from the first separation device directly to liquid para-xylene product without additional processing makes the process of the invention more efficient and more cost effective than crystallization processes which require further processing of the para-xylene crystals, such as recrystallization and recentrifugation. A washing operation may be performed in the separation device 30 to increase the purity of the para-xylene product stream 5 to 99.5 wt % para-xylene or higher, preferably 99.8 wt % para-xylene or higher. If a washing operation is performed, a portion of the para-xylene melt is returned to the separator 30 and sprayed on the para-xylene cake at the end of the separator 30. The ratio of wash liquid to crystalline para-xylene is suitably about 0.05 to about 0.5 by weight, preferably about 0.15 to about 0.25 by weight. When the liquid/solid separator is a centrifuge and purified para-xylene is used as a wash liquid, it is preferable that the temperature of the slurry of para-xylene crystals and mother liquor being separated be at a temperature of at least about 37° F. The liquid-solid separation device 30 also yields one or more filtrate streams conveyed via lines 3 (stream 3), and 4 (stream 4) in FIG. 7. Stream 3 is a reject filtrate stream, and stream 4 is a wash filtrate stream which contains more para-xylene than stream 3. For an embodiment in which stream 1 contains about 90 wt % para-xylene, stream 3 may contain about 81 wt % para-xylene and stream 4 may contain about 84 wt % para-xylene. These weight percentages may vary depending upon the type of centrifuge used and the wash ratio chosen. If the para-xylene product stream 5 contains solids, as is the case when centrifuges are used as the separation device, the solids can be melted to produce a liquid product. If a wash liquid is used, it can be either the liquid para-xylene product itself or other materials such as toluene or methanol. If the wash liquid is not the para-xylene product, then further separations are used to obtain the final purified para-xylene product and to recover the washing material(s). Two distillation columns are typically employed for this purpose. Preferably, the washing liquid will be a fraction of the para-xylene product.

For an embodiment wherein there is only one filtrate stream effluent from the separation device 30, line 4 in FIG. 7 has no effluent flow and can be eliminated. For a pusher centrifuge in product stage service, there are typically two filtrate streams as shown in FIG. 7. The composition of the filtrate in line 3 (stream 3), which is the reject filtrate, is lower in para-xylene than that of the filtrate in line 4 (stream 4), which is the wash filtrate. The filtrate in line 4 can be sent to a reslurry drum 32 via line 19 as a diluent as shown in FIG. 7. In order to control the temperature in reslurry drum 32, the filtrate stream conveyed via line 4 can be heated with the use of a heat exchanger (not shown) before being added to the reslurry drum.

A portion of the reject filtrate stream conveyed via line 3 can be sent to reslurry drum 32 via line 17 as diluent. The portion of stream 3 filtrate conveyed to reslurry drum 32 via line 17 can be heated, if desired, in order to control the temperature in the reslurry drum. The remaining portion of filtrate stream 3 may be combined with any filtrate from liquid-solid separator 31 in line 13 that is not recycled via line 18 to reslurry drum 32 to be used as diluent in reslurry drum 32. The combined streams from lines 3 and 13 are fed via line 25 to a second crystallizer 200 that operates at a lower temperature than the first crystallizer 100. Crystallizer 200 is operated at a temperature of from about −10° F. to about 35° F., preferably from about 15° F. to about 25° F. The effluent from the lower temperature crystallizer 200, which comprises crystalline para-xylene and mother liquor, is conveyed via line 6 to a separator 33 which comprises one or more liquid-solid separation devices. For the example shown, the effluent in line 6 is at about 25° F. The embodiment illustrated in FIG. 7 utilizes a single centrifuge as the separator 33 although more than one centrifuge or other separation means can be used. The crystalline para-xylene cake from centrifuge 33 is conveyed via line 8 to reslurry drum 32. The filtrate from centrifuge 33 is sent via line 7 to a third crystallizer 300 which is at a lower temperature than crystallizer 200. For an embodiment in which stream 1 contains about 90 wt % para-xylene, stream 7 will contain about 68 wt % para-xylene. Crystallizer 300 is operated at about −35° F. to about 5° F., preferably from about −10° F. to about −5° F. As explained above, other separation devices could be used in place of centrifuges 33 and 34. Although not shown in FIG. 7, one or more washing steps can be included, if desired. If washing is used, then multiple filtrate streams may be obtained, each with a different para-xylene composition. These filtrate streams can be either recycled back or fed forward to different parts of the design depending on their particular composition. The preferred embodiment does not use wash.

The effluent from crystallizer 300, which is a slurry comprising crystalline para-xylene and mother liquor, is fed via line 9 to a separator 34, which comprises one or more liquid-solid separation devices. In the embodiment illustrated in FIG. 7, the crystallizer effluent conveyed via line 9 is at about −5° F. In the embodiment illustrated, a single pusher centrifuge is used as the separator 34. The para-xylene cake from centrifuge 34 is sent via line 11 to the reslurry drum 32 while the filtrate is removed via line 10. The filtrate stream in line 10 can be used to cool the $C_8$ aromatic feed stream 1 before stream 1 enters the high temperature crystallizer 100. This will reduce the refrigeration requirement for this crystallizer. The filtrate stream in line 10 can then be sent to either a reactor, such as a reactor that converts ethylbenzene to other compounds that can be separated more easily from the other $C_8$ aromatics, or to another separation process. For an embodiment in which stream 9 is at −5° F., stream 10 will contain about 45 wt % para-xylene.

The reslurry drum 32 is operated at a sufficiently high temperature so that the effluent from the reslurry drum can be sent to one or more liquid-solid separation devices that are capable of producing more high purity product. Although not necessary, the temperature of the reslurry drum may be higher than any of the aforementioned crystallizers. In all cases, it will be warmer than the lowest temperature crystallizer. The temperature of the slurry is suitably at least about 10° F., preferably about 30° F. to about 55° F., more preferably about 35° F. to about 45° F., more preferably at a temperature of about 38° F. to about 42° F., and most preferably at a temperature of about 40° F. to about 42° F. Crystalline para-xylene is contacted with para-xylene-containing liquid in a slurry for a time sufficient to allow the crystals and the mother liquor to approach equilibrium. This time is preferably about 0.1 to about 2 hours, more preferably about 0.4 to about 1 hour. The amount of liquid in the slurry should be an amount sufficient to produce a mixture than can be slurried and pumped. The liquid used for the slurry is a liquid which contains para-xylene. Those streams having higher concentrations are more preferred for use as slurry liquid. For example, for the embodiment shown in FIG. 7, streams 4 and 14 would preferably be chosen first and then stream 3 and/or stream 13. After the slurry is sufficiently equilibrated, the purified crystalline para-xylene is separated from the liquid and preferably washed with liquid para-xylene to remove adhering mother liquor. The liquid para-xylene used for the wash is preferably high purity para-xylene having a purity of at least about 99.5 weight percent, preferably at least about 99.7 weight percent, more preferably at least about 99.8 weight percent. The weight ratio of liquid para-xylene wash to crystalline para-xylene is typically about 0.05:1 to about 0.5:1 by weight, more preferably about 0.15:1 to about 0.25:1; still more preferably about 0.18:1 to about 0.2:1. Upon melting the purified crystalline para-xylene, a liquid product para-xylene having a purity of at least 99.5 weight percent, more preferably at least about 99.7 weight percent, and most preferably at least about 99.8 weight percent is produced.

In cases where the reslurry drum 32 is warmer than crystallizer 100, it is possible that the concentration of para-xylene in the filtrate stream in line 13 can approach or exceed the concentration of the para-xylene feed in line 1. In such cases, the fraction of the filtrate stream in line 13 that is not recycled to the reslurry drum 32 can be sent to crystallizer 100 rather than to crystallizer 200, further improving the energy efficiency of the process. This is the process shown in FIG. 8. Reslurry drum 32 is operated at about 10° F. to about 55° F., preferably from about 30° F. to about 50° F.

A slurry of para-xylene crystals and para-xylene-containing liquid is prepared in reslurry drum 32. The para-xylene-containing liquid used to prepare the slurry of crystalline para-xylene and liquid para-xylene can be one or more of the mother liquor streams produced by separating the crystalline para-xylene from liquid mother liquor. The para-xylene-containing liquid used for the slurry is an amount suitable for providing for the slurry of crystalline para-xylene and liquid. For an embodiment in which stream 1 in FIG. 7 contains about 90 wt % para-xylene, the liquid to the reslurry drum preferably comprises all of stream 4, which is 84 wt % para-xylene, all of stream 14, which is 86 wt % para-xylene, and 32% of stream 13, which is 83 wt % para-xylene. Typically, the remainder is a mixture of ortho- and meta-xylene, ethylbenzene and other hydrocarbons from the process. The amount of crystalline para-xylene in the slurry is typically about 30 to about 60 weight percent, preferably about 30 to about 55 weight percent, and most preferably about 35 to about 50 weight percent. This slurry is preferably agitated, preferably by a mechanical agitator. The slurry is retained in the slurry vessel 32 for a time sufficient to permit all of the slurry to approach equilibrium. For the preferred continuous operation of this embodiment of the invention, the residence time for this slurry in the slurry vessel 32 is suitably about 0.2 to about 2 hours, more preferably about 0.4 to about 1 hour.

The liquid-solids separator 31 is fed from the reslurry drum 32. The types of separation devices that can be used have already been discussed in connection with stream 2 above. In one embodiment of the process illustrated in FIG. 7, two centrifuges are used. Washing (not shown) may also be provided. When washing is used, a portion of the purified para-xylene melt from melt drum 35 is used to wash the para-xylene cake at the end of the centrifuge. The crystalline para-xylene cake from separator 31 is sent to melt drum 35 via line 15 and the para-xylene crystals are completely melted to provide purified para-xylene product. A portion of the para-xylene melt may be recycled to centrifuge 31 as a wash liquid. For the embodiment shown in FIG. 7, the para-xylene stream in line 15 is a para-xylene product stream from centrifuge 31, and the filtrate streams in lines 13 and 14 are the filtrate streams from centrifuge 31. The total para-xylene product stream is conveyed from the melt drum 35 via line 16 and is the combination of the para-xylene product streams from lines 5 and 15. The filtrate stream in line 14 (the wash filtrate) has a higher composition of para-xylene than the filtrate stream in line 13 (the reject filtrate). The wash filtrate stream in line 14 can be combined with the wash filtrate stream in line 4 and sent via line 19 to the reslurry drum 32 as diluent. A portion of the reject filtrate stream in line 13 can also be sent to the reslurry drum 32 as diluent. The remaining portion of reject filtrate stream 13 is combined with reject filtrate stream 3 and sent to crystallizer 200 as discussed above. Any or all of the streams used as diluent in the reslurry drum can be warmed through the use of a heat exchanger (not shown). Moreover, some or all the various diluent streams can be combined before entering the reslurry drum or before passing through a heat exchanger. Other alternatives for controlling the reslurry drum temperature, such as warming the reslurry drum through the use of a steam jacket may also be used.

There are two important concepts in the invention. The first concept centers on the first stage of crystallization and separation. By the appropriate choice of process conditions and equipment, the first stage is capable of producing high purity product (stream 5) that does not require further processing.

In the example provided, over 50% of the final product (the stream in line 16 which is a combination of product streams 5 and 15), which has a purity of about 99.85 wt % para-xylene, is obtained from the first crystallization/separation stage. This material does not go through the downstream equipment; therefore, the energy requirements are reduced and probably the capital costs are also reduced compared with most other processes (particularly those discussed in U.S. Pat. No. 6,111,161).

The second important concept centers on the reslurry drum whose function is to warm all the cake that is too cold to conveniently yield high purity para-xylene product directly. Most importantly, the reslurry drum requires no refrigeration, which reduces energy costs compared with other process designs, although it may require heat. Therefore, the cake from the colder crystallization stages can be processed using the reslurry drum to yield high purity para-xylene product (the crystalline para-xylene stream in line 15) without the need for further refrigeration. (The use of this reslurry drum makes the present invention significantly different from the invention disclosed in U.S. Pat. No. 5,448,005.) Finally, the reslurry drum in the present invention is not simply a device to partially melt crystals to make a suspension. The reslurry drum in this invention is capable of yielding more crystalline para-xylene solids in the slurry drum effluent than provided in all the various input streams despite the addition of heat. Therefore, the present invention also includes those embodiments wherein the amount of para-xylene crystals in the slurry mixture formed in the slurry apparatus is greater than the amount of para-xylene crystals sent to the slurry apparatus.

The temperatures of the various crystallization stages and the number of the crystallization stages will vary depending on the refrigeration cycle(s) chosen, the refrigerant(s) chosen, and the composition of stream 1. The choice of separation equipment may also alter the schematic and the ultimate purity of the para-xylene product. For example, wash columns typically have only one reject filtrate stream and they may yield a higher purity product than centrifuges.

Another embodiment of the process of the present invention is illustrated in FIG. 8. A feed (stream 102) comprising at least about 55 wt % para-xylene is sent via line 102 to crystallizer 150. It is desirable that the composition of stream 102 be at least about 55 weight percent (wt %) para-xylene, preferably greater than about 55 wt % para-xylene, more preferably at least about 60 wt % para-xylene, more preferably at least about 70 wt % para-xylene, more preferably at least about 75 wt % para-xylene, more preferably at least about 80 wt % para-xylene, more preferably at least about 85 wt % para-xylene, more preferably at least about 90 wt % para-xylene, and most preferably at least about 95 wt % para-xylene. Crystallizer 150 is operated at a temperature of about 10° F. to about 55° F., preferably about 20° F. to about 30° F.

The crystallizer 150 effluent, which comprises para-xylene crystals and mother liquor, is sent to a separation unit 130 comprising one or more centrifuges which are used to separate para-xylene crystals from the mother liquor. Separation devices other than centrifuges, such as wash columns or rotary filters can also be used at this step and in other steps in the process where liquid-solids separation devices are used. The crystalline para-xylene cake is washed inside the centrifuges using high purity para-xylene material. The centrifuges 130 produce high purity para-xylene product (stream 106) and two filtrate streams (streams 104 and 105). Stream 105 is the wash filtrate and is more concentrated in para-xylene than the reject filtrate, stream 104. All of the wash filtrate is sent to the reslurry drum 132 to provide some of the liquid for the reslurry operation. All of the reject filtrate is sent via line 104 to crystallizer 250 which operates at a temperature lower than crystallizer 150. Crystallizer 250 is operated at a temperature of from about −10° F. to about 35° F., preferably from about 5° F. to about 15° F.

The effluent from crystallizer 250, which comprises a slurry of crystalline para-xylene in mother liquor, is sent via line 107 to separation unit 133, which comprises at least one centrifuge or other separation means. The crystalline para-xylene cake from the centrifuge 133 is conveyed via line 109 into the reslurry drum 132 while the reject filtrate (stream 108) is sent via line 108 to crystallizer 350, which operates at a temperature lower than crystallizer 250. Crystallizer 350 is operated at a temperature of from about −35° F. to about 5° F., preferably from about −10° F. to about −5° F.

The effluent from crystallizer 350 (stream 110) which comprises a slurry of crystalline para-xylene in mother liquor is sent via line 110 to separation unit 134 which comprises at least one centrifuge or other separation means. The crystalline para-xylene cake from the centrifuge is dropped into reslurry drum 132. The reject filtrate (stream 111) contains about 45% para-xylene and is heat exchanged with feed stream 101 before being sent elsewhere in the unit. For example, it may be sent to an ethylbenzene reactor or to another separation process. The slurry from reslurry drum 132, which comprises crystalline para-xylene and mother liquor, is sent via line 113 to a separation unit 131 comprising one or more centrifuges where the crystalline para-xylene is separated from the mother liquor. The crystalline para-xylene cake is washed inside these centrifuges using high purity para-xylene material. These centrifuges produce additional high purity para-xylene product, stream 116 which is combined with high purity para-xylene product stream 106, melted in a melt drum (not shown) if necessary, and collected via line 117. Separation unit 131 also produces two filtrate streams (streams 114 and 115). Stream 115 is the wash filtrate and is more concentrated in para-xylene than the reject filtrate, stream 114. All of the wash filtrate is sent via line 115 to the reslurry drum 132 to provide some of the liquid for the reslurry operation. A portion of the reject filtrate is sent via line 114 to the reslurry drum 132 to provide the rest of the liquid for the reslurry operation. The reslurry drum 132 is operated at a temperature of from about 10° F. to about 55° F., preferably from about 30° F. to about 50° F., more preferably from about 35° F. to about 45° F., more preferably from about 38° F. to about 42° F., and most preferably at a temperature from about 40° F. to about 42° F. The remaining reject filtrate (stream 114) from separation unit 131 is combined with stream 101 upstream of crystallizer 150 to form feed stream 102. For an embodiment in which stream 102 contains about 70 wt % para-xylene, stream 114 will contain about 83 wt % para-xylene. In this embodiment of the process of the invention, crystallizer 150 is operated at a temperature of from about 10° F. to about 55° F., preferably from about 20° F. to about 30° F. Crystallizer 250 is operated at a temperature of from about −10° F. to about 35° F., preferably from about 5° F. to about 15° F., and crystallizer 350 is operated at a temperature of from about −35° F. to about 5° F., preferably from about −10° F. to about −5° F.

The following examples will serve to illustrate certain embodiments of the invention disclosed herein. These examples should not, however, be construed as limiting the scope of the novel invention as there are many variations which may be made thereon without departing from the spirit of the disclosed invention, as those of skill in the art will recognize.

Experimental Equipment

A mass flow controller determines the Helium flow rate. A saturated flow of He, which contains EB and xylenes, is passed over the bed of adsorbent heated to the adsorption temperature. At the outlet of the bed, the gas stream is analyzed by gas chromatography to determine the composition. Any compounds not adsorbed are collected in a trap filled with silica gel with pores large enough to adsorb all compounds. After the adsorbent bed is saturated, the saturator is by-passed delivering only He to the adsorbent bed. The sample receiver is switched to a second silica gel adsorbent bed and the temperature is increased to 250° C. to affect desorption. After desorption, the receivers are removed and weighed. The receivers are then heated to desorb the adsorbed hydrocarbons, which are collected in a cold trap and subsequently analyzed by gas chromatography.

Adsorbents (1) HZSM-5

H-ZSM-5 containing 2% Al was a commercial sample (CBV-3020) obtained from PQ Corporation (Valley Forge Executive Mail, PO Box 840, Valley Forge, Pa. 19482).).

(2) HZSM-5

A second sample of HZSM-5 was prepared according to the following procedure: 20.66 g of NaOH was dissolved in 560.3 g distilled water, followed by 10.6 g of sodium aluminate ($Na_2O \cdot Al_2O_3 \cdot 3H_2O$) and 98.13 g tetrapropylammonium bromide (TPABr). The mixture was stirred until a clear solution formed. 485.9 g Nalco 2327 silica sol (40 wt % $SiO_2$) was then added and the mixture stirred for two hours. The pH of the resulting mixture was 12.5. The mixture was transferred to a Teflon-lined Parr reactor and heated at 300° F. (150° C.) for seven days with stirring (275 rpm). The reaction mixture was cooled and filtered, and the solid product washed with 10 L of distilled water. The zeolite powder was calcined to remove the template using the following program: Dry at 329° F. (165° C.) for 4 hr.; ramp to 950° F. (510° C.) over 4 hr.; hold at 950° F. (510° C.) for 12 hr.; ramp back to ambient temperature over 4 hr.

(3) Na-ZSM-5

Sample (2) was $Na^+$ exchanged by heating 50 g of the sieve in a solution of $NaNO_3$ (50 g in 500 ml distilled water) at 175° F. (80° C.) with stirring. The sieve was filtered and the exchange repeated with the addition of adjusting the pH to 9.5 with 50% NaOH solution. Again, the sieve was filtered and then washed by stirring for one hour in distilled water (500 ml) heated at 175° F. (80° C.). The sample was calcined using the same temperature program described above, except holding at 950° F. (510° C.) for four hours. Elemental analysis of this sample gave 1.84 wt % Na and 1.3 wt % Al. The washing step was repeated three more times to remove the excess $Na^+$. The final sample was dried for 5 hours at 220° F. (105° C.). Elemental analysis by ICP showed the washed zeolite to have 1.3 wt % Al and 1.2 wt % Na, which is a 5% molar excess of Na.

(4) Silicalite

Silicalite was prepared by adding 18.4 g NaOH to 227.6 g $H_2O$. After dissolution, 12.8 g tetrapropylammonium bromide was dissolved and 122.6 g Nalco 2327 silica sol was added and stirred for 2 hours. Concentrated $H_2SO_4$ was slowly added to achieve a pH of 13. The resulting solution was heated under autogenous pressure in a Teflon-lined autoclave for 1–7 days at 300° F.(150° C.). The crystals were filtered and washed to a neutral pH filtrate.

(5) Silicalite

A second sample of silicalite comprising crystals ~0.1 micron in size was prepared according to the following procedure: 1.72 g of NaOH was dissolved in 120 ml of a 1.0 M solution of tetrapropylammonium hydroxide (TPAOH). 30.0 g Cab-o-Sil M-5 silica was then added to the solution, forming a slurry. The slurry was stirred at 175° F. (80° C.) until a clear solution formed. Additional distilled water was added to make up any losses due to evaporation. The solution was transferred to a Teflon-lined Parr reactor and heated at 300° F. (150° C.) for 24 hours. The resulting mixture was centrifuged and the solids layer redispersed in distilled water. This process was repeated until the pH of the silicalite sol was <9. A portion of the silicalite sol was dried and calcined using the procedure described for sample (2), in order to obtain a solid sample for the adsorption experiments.

(6) Ti-MFI (TS-1)

182.4 g of tetraethylorthosilicate and 2.53 g of tetraethylorthotitanate were mixed with 400.23 g of tetrapropylammonium hydroxide (20% in water). In order to remove the ethanol, the mixture was heated at 175–195° F. (80–90° C.) for 5 hours with stirring. After cooling the mixture to ambient temperature, the volume of the mixture was diluted to 600 ml with distilled water. The mixture (pH=12) was heated at 350° F. (175° C.) for 14 days with stirring (~270 rpm). The white powder was washed with distilled water and calcined using the procedure described for sample (2).

(7) ZSM-22

4.7 g of NaOH was dissolved in 119 g of distilled water. 640 g of MeOH and 220 g of Nalco 2327 silica sol (nominally 40 wt % $SiO_2$) were then added. The mixture was transferred to a 2 L autoclave and heated at 320° F. (160° C.) for 28 hours with stirring (~150 rpm). The product was collected by filtration and washed with 16 L of distilled water and calcined using the procedure described for sample (2).

EXAMPLE 1

Determination of $C_8$ Aromatic Adsorption Capacity of Silicalite

Figure 6:
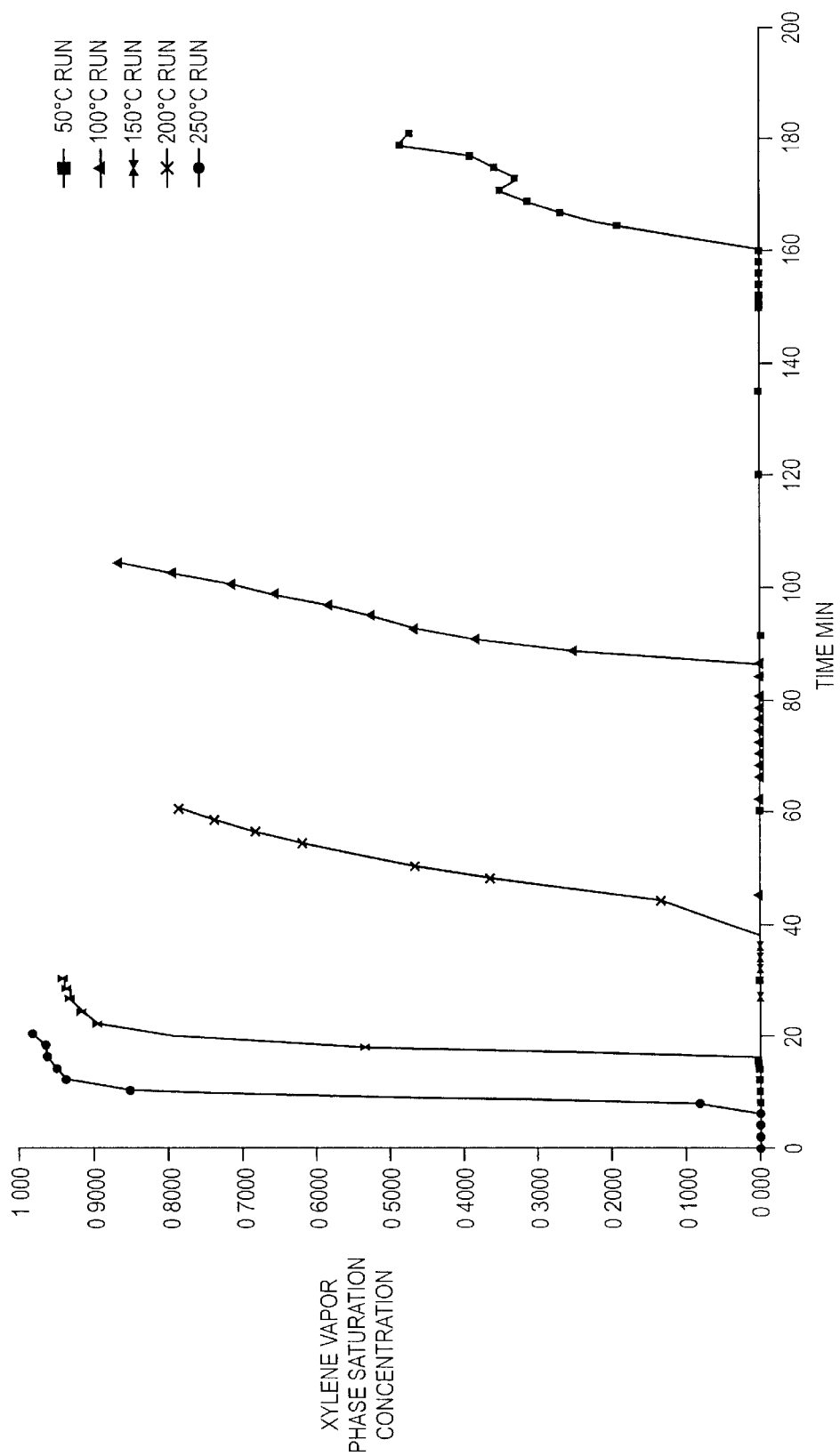
FIG. 6 shows a graph of Xylene Vapor Phase Concentrations vs. Adsorbance Time.

When a saturated stream of pX (or EB) is passed over H-ZSM-5 or silicalite at low temperature there is nearly complete adsorption. At the inlet to the reactor the concentration is equivalent to the vapor pressure, while at the outlet of the bed little pX can be detected. At saturation, the bed can no longer adsorb pX, and the concentration at the bed outlet quickly increases to the inlet concentration, as shown in FIG. 6. The amount adsorbed is proportional to the product of the flow rate, concentration and time, equation 1.

$$g \text{ adsorbed} = [\text{He flow (cc/min)} \times \text{Conc (torr/760 torr/atm)} \times 1 \text{ atm} \times t \text{ (min)} \times 106 \text{ g/mol}]/22400 \text{ cc/mol} \quad (1)$$

With increasing temperature the amount of pX adsorbed on silicalite decreases as shown in Table 1. At 50° C. and a pX partial pressure of 6 torr (0.8 kPa), the saturation adsorption capacity was measured to be 9.2 wt % (92 mg/g) pX on silicalite (Adsorbent 4), while at 250° C. the adsorption capacity decreases to 0.3 wt % (3 mg/g).

TABLE 1

Adsorption of para-Xylene by Silicalite at Atmospheric Pressure (6 torr pX; 0.8 kPa)

| Adsorption Temperature, ° C. | Adsorption Capacity (mg pX/g silicalite) |
| --- | --- |
| 50 | 92 |
| 100 | 49 |
| 150 | 24 |
| 200 | 10 |
| 250 | 3 |

Single component adsorption capacities were also measured for mX, oX and EB. A comparison of the single component saturation adsorption capacity of pX, EB, mX and oX measured at 50° C. is shown in Table 2. The data demonstrates that silicalite (Adsorbent 4) has a much higher adsorption capacity for pX and EB than it does for mX and oX.

TABLE 2

Adsorption Capacity at 50° C. and atmospheric pressure (6 torr; 0.8 kPa)

| C$_8$ Aromatic Isomer | Adsorption Capacity (mg/g silicalite) |
|---|---|
| pX | 92 |
| EB | 63 |
| oX | <2 |
| mX | <2 |

EXAMPLE 2

Separation of Para-Xylene from Ortho-Xylene with Silicalite (Adsorbent 4)

A 1:1 mixture (3 torr:3 torr) of para-xylene and ortho-xylene was passed over the silicalite (4) adsorbent at 50° C. Monitoring the outlet stream by gas chromatography (GC) indicated that pX was adsorbed by the silicalite. Essentially ortho-xylene was not adsorbed by the silicalite, but rather passed through and was collected in a downstream trap containing amorphous silica adsorbent. Before the silicalite bed was completely saturated with para-xylene (i.e., pX breakthrough was not yet observed), the flow of xylenes was discontinued and He purged through the bed. The effluent stream was then directed to a second amorphous silica-containing trap, and the temperature of the silicalite bed was increased to 300° C. to desorb the xylenes. The adsorbed materials were recovered from the two amorphous silica traps and analyzed for xylenes by GC. The analyses are given in Table 3. The results show that para-xylene is selectively adsorbed on silicalite while ortho-xylene is essentially not adsorbed. The amount of para-xylene adsorbed was 89 mg/g which is slightly below the adsorption capacity.

TABLE 3

Silicalite: Separation of pX/oX (3 torr/3 torr) at 50° C. and Atmospheric Pressure

| Not Adsorbed | Adsorbed | Adsorbed, mg/g |
|---|---|---|
| 99% oX (0.3% pX) | 97.6% pX (2.1% oX) | 89.0* (8.9 wt %) |

*Adsorption not run to saturation.

EXAMPLE 3

Separation of C$_8$ Aromatic Mixtures with Silicalite (Adsorbent 4)

A 1:1:1:1 mixture of pX:EB:mX:oX (8 torr total C$_8$) produced by bubbling He through an equimolar mixture of pX, EB, mX, and oX at atmospheric pressure)was passed over the silicalite (4) adsorbent at 50° C. Essentially mX and oX were not adsorbed on the silicalite, but passed through and were collected into the first silica trap. When the silicalite bed became saturated with pX and EB, the flow of xylenes was discontinued and He purged through the bed. The effluent was then switched to the second silica trap and the temperature of the silicalite bed increased to 300° C. to desorb the adsorbed hydrocarbons. The adsorbed materials were recovered from the two silica beds and analyzed for C$_8$ aromatics. The analysis is given in Table 4. The results show that in a mixture of EB and xylenes, pX and EB are selectively adsorbed on silicalite, while mX and oX are essentially not adsorbed.

TABLE 4

Silicalite: Separation of C$_8$ Aromatics at 50° C. and atmospheric pressure (8 torr)

| Not Adsorbed Composition | Adsorbed Composition | Wt % Adsorbed |
|---|---|---|
| 2.6% pX | 45.7% pX | |
| 5.5% EB | 51.4% EB | 6.5% (pX and EB) |
| 52.4% mX | 1.4% mX | |
| 39.2% oX | 1.1% oX | |

EXAMPLE 4

Comparison with HZSM-5: Adsorption of EB and Xylenes on H-ZSM-5 (Adsorbent 1) (CBV-3020)

Following the procedure described in Example 1, the saturation adsorption capacity of H-ZSM-5 (Adsorbent 1) was determined. Table 5 compares the saturation adsorption capacity of pX, EB, mX and oX at 50° C. The table demonstrates that for H-ZSM-5, pX and EB have a much higher adsorption capacity than mX and oX, although there is significant adsorption of the latter two.

TABLE 5

H-ZSM-5 (1): Adsorption Capacity at 50° C. and atmospheric pressure (8 torr)

| C$_8$ Aromatic Isomer | Adsorption Capacity (Wt %) | (mg/g) |
|---|---|---|
| pX | 9.0 | 90 |
| EB | 7.5 | 75 |
| oX | 4.0 | 40 |
| mX | 4.0 | 40 |

EXAMPLE 5

Separation of Mixtures with H-ZSM-5 (Adsorbent 1) Prior Art

A 1:1:1:1 mixture (8 torr total) of pX:EB:mX:oX was passed over the H-ZSM-5 (Adsorbent 1) adsorbent at 50° C. After saturation, the flow of xylenes was discontinued and He purged through the bed. The effluent was switched to the second bed of silica and the temperature in the H-ZSM-5 bed was increased to 300° C. to desorb the xylenes adsorbed. The products were recovered and analyzed for xylenes. The analysis of the C$_8$ aromatics adsorbed on H-ZSM-5 are given in Table 6 along with results for silicalite (Adsorbent 4), under the same conditions. The results show that for the material desorbed from H-ZSM-5, the pX and EB concentrations are much lower, mX and oX are higher, and small amounts of benzene (Bz), toluene (Tol) and C$_9$ aromatics are present, indicating that some adsorbed xylenes reacted on the acid sites during high temperature desorption.

TABLE 6

Separation of $C_8$ Aromatics at 50° C. and atmospheric pressure (6 torr)

| Composition of Material Desorbed from Silicalite (4) Example 3 | Composition of Material Desorbed from H-ZSM-5 (1) Example 5 |
|---|---|
| — | 5.5% Bz |
| — | 5.9% Tol |
| 45.7% pX | 20.1% pX |
| 51.4% EB | 33.6% EB |
| 1.4% mX | 22.9% mX |
| 1.1% oX | 10.7% oX |
| — | 0.9% $C_9$ |

EXAMPLE 6

Comparison: Reaction of adsorbed $C_8$ aromatics on H-ZSM-5 (Adsorbent 1)

Desorption products from H-ZSM-5 (Example 5) suggest that aromatics react with acid sites in H-ZSM-5 at high desorption temperatures. To confirm, para-xylene was adsorbed at 50° C., atmospheric pressure and 6 torr partial pressure on silicalite (Adsorbent 4), and H-ZSM-5 (Adsorbent 1),. The adsorbed pX was recovered by heating to 300° C. Analysis of the reaction products is given in Table 7 and indicates that there is substantial isomerization (pX to mX and oX) and transmethylation [pX to toluene and $C_9$, such as trimethylbenzene (TMB)] over H-ZSM-5, whereas, no reaction occurred over silicalite.

TABLE 7

Reactivity of Adsorbed pX

| Composition of Material Desorbed from Silicalite (4) | | Composition of Material Desorbed from H-ZSM-5 (1) | |
|---|---|---|---|
| pX | 100% | Bz | 0.1% |
| | | Tol | 2.1% |
| | | pX | 78.1% |
| | | mX | 14.3% |
| | | oX | 4.0% |
| | | TMB | 1.2% |

EXAMPLE 7

Adsorption/desorption of olefins on Silicalite and H-ZSM-5

The effect of trace olefins, which are always present in the reactants in commercial feedstreams, on the adsorption capacity was evaluated by saturation of H-ZSM-5 (Adsorbent 1), and silicalite (Adsorbent 4), at room temperature with propylene, Table 8. The quantity of adsorbed hydrocarbon was determined at temperatures up to 200° C. H-ZSM-5 readily adsorbs about 7 wt % propylene at room temperature. As the temperature increases, some propylene desorbs. Even at 200° C., however, 10% of the initial amount adsorbed remains. In order to keep olefins from lowering the adsorption capacity of H-ZSM-5 it will be necessary to operate at temperatures of above about 450° F. (about 230° C.). At these temperatures, however, significant reactions occur leading to poor selectivity. At lower temperature, desorption times are very long and olefins will reduce the adsorption capacity. In contrast silicalite does not adsorb olefins even at room temperature, thus the adsorption capacity will be unchanged with repeated adsorption/desorption cycles. The adsorption capacity of silicalite is unchanged after more than 25 adsorption/desorption cycles.

TABLE 8

Adsorption of Propylene

| Temp. | H-ZSM-5 (1) | Silicalite (4) |
|---|---|---|
| 20° C. | 6.9 wt % | 0 wt % |
| 100° C. | 5.2 wt % | — |
| 150° C. | 2.7 wt % | — |
| 200° C. | 0.6 wt % | — |

EXAMPLE 8

Effect of Xylene Partial Pressure on Adsorption Capacity at Elevated Pressure

In order to rapidly desorb para-xylene and ethylbenzene, the desorption temperature should be above about 450° F. (about 230° C.). At low partial pressure, however, the adsorption capacity is low, as seen in Table 1. The adsorption capacity at elevated temperature can be increased by increasing the adsorbate (pX and EB) partial pressure. In order to increase the pX partial pressure, the xylene saturator was replaced by an ISCO syringe pump. Additionally, a 6-way valve, heat tracing and other minor modifications were required to give instant vaporization of the xylene.

Table 9 gives the adsorption capacity of pX on silicalite (Adsorbent 4) at different temperatures and partial pressures. The data show that at constant partial pressure, the amount of pX adsorbed decreases with increasing temperature. Whereas, at high temperature, the amount of pX adsorbed can be increased by increasing the partial pressure of pX.

TABLE 9

Adsorption of pX by Silicalite at Various Temperatures and Pressures

| Ppx, torr | Temperature, ° C. | mg pX adsorbed per gram silicalite |
|---|---|---|
| 6 | 50 | 92 |
| 6 | 100 | 49 |
| 6 | 150 | 24 |
| 6 | 200 | 10 |
| 6 | 250 | 4 |
| 500 | 250 | 20 |
| 888 | 250 | 29 |
| 1996 | 250 | 60 |

EXAMPLE 9

Separation of $C_8$ Aromatic Mixtures with Silicalite at Elevated Pressure

A 1:1:1:1 mixture of pX:EB:mX:oX at a total pressure of 89 psig and 38.6 psia partial pressure of $C_8$ aromatics (1995 torr) was passed over the silicalite (4) adsorbent at 250° C., The effluent composition was monitored by gas chromatography (GC). As in Example 1, when the silicalite adsorbent bed is saturated with a given isomer, the concentration of that isomer in the vapor phase at the bed outlet quickly increased to the inlet vapor phase concentration. The time required to detect that isomer at the bed outlet is proportional to the amount adsorbed on the bed.

The amount of mX and oX adsorbed was relatively small, while significantly larger amounts of pX and EB were adsorbed, Table 10. The results show that pX and EB can be selectively adsorbed at elevated temperatures and pressures in an amount comparable to pX alone (Example 8) at the same partial pressure.

TABLE 10

Adsorption Capacity of $C_8$ Aromatics at 250° C. and 1996 torr Partial Pressure (pX partial pressure about 500 torr)

| | |
|---|---|
| mX | 3 mg/g |
| oX | 3 mg/g |
| pX | 21 mg/g |
| EB | 22 mg/g |

EXAMPLE 10

Comparison of Silicalite and NaZSM-5

Non-Acidic NaZSM-5—Since HZSM-5 isomerizes and transmethylates the adsorbed xylenes, a non-acidic, sodium exchanged sample was prepared and tested. It was found that CBV-3020 could not be completely exchanged; therefore, another sample of HZSM-5 (Adsorbent 2), was prepared containing 1.3 wt % Al. This material was completely exchanged with Na, such that no acid sites remained to give Na-ZSM-5(Adsorbent 3),. The adsorption capacity for pX was 115 mg/g at 50° C. and atmospheric pressure. Increasing the temperature to 250° C. decreased the adsorption capacity to 26.3 mg/g. Furthermore, at 250° C., only pX was observed in the effluent, confirming complete exchange of the acid sites with $Na^+$.

This sample was also tested with a saturated gas mixture (1 atm) of C8 aromatics in He at 50° C., as was done with silicalite and HZSM-5. The adsorbate was desorbed and analyzed by GC. A comparison of these results with those obtained for silicalite (Adsorbent 4) is given in Table 11. The mX and oX present in the desorbate for NaZSM-5 is not due to isomerization (as verified with the feed containing only pX). Thus, the NaZSM-5 sample has a lower pX adsorption selectivity than the silicalite sample tested, but a greater total capacity at these conditions.

To determine whether the decrease in pX selectivity is due to decreasing crystal size, a silicalite sample (Adsorbent 5), having a crystal size of approximately 0.1 μm was also prepared and tested. The composition of the adsorbate is compared with that of the adsorbates obtained for large crystal silicalite (Adsorbent 4), small crystal HZSM-5 (Adsorbent 1), and small crystal NaZSM-5 (Adsorbent 3) in Table 12. The size of the small crystal silicalite sample was determined by Transmission Electron Microscopy (TEM) to be approximately 0.1 μm. The crystal size of the two ZSM-5 samples was determined by Scanning Electron Microscopy (SEM) to be approximately 0.1–0.4 μm. The size of the large crystal silicalite sample was also determined by SEM to have an average minimum dimension of greater than 0.5 μm.

TABLE 11

Comparison of Silicalite and NaZSM-5
(Feed is a He stream saturated with $C_8$ aromatics
(oX, mX, pX, and EB); adsorbed at 50° C. and 1 atm)

| Silicalite (4) 65 mg adsorbate/g Silicalite | NaZSM-5 (3) 88 mg adsorbate/g NaZSM-5 |
|---|---|
| Adsorbate Compositions | |
| 1.4% mX | 9.5% mX |
| 1.1% oX | 7.7% oX |

TABLE 11-continued

Comparison of Silicalite and NaZSM-5
(Feed is a He stream saturated with $C_8$ aromatics
(oX, mX, pX, and EB); adsorbed at 50° C. and 1 atm)

| Silicalite (4) 65 mg adsorbate/g Silicalite | NaZSM-5 (3) 88 mg adsorbate/g NaZSM-5 |
|---|---|
| 45.7% pX | 45.0% pX |
| 51.4% EB | 37.8% EB |

TABLE 12

Comparison of Adsorbates for Large Crystal Silicalite with Small
Crystal Silicalite, HZSM-5, and NaZSM-5 at 50° C. and 1 atm.
(Feed is a He stream saturated with $C_8$ aromatics
(oX, mX, pX, and EB);

| Silicalite (4) (>0.5 μm average minimum dimension) 65 mg adsorbate/ g Silicalite | Silicalite (5) (about 0.1 μm) 83 mg adsorbate/ g Silicalite | HZSM-5 (1) (about 0.1– 0.4 μm) 85 mg adsorbate/ g HZSM-5 | NaZSM-5 (3) (about 0.1– 0.4 μm) 88 mg adsorbate/ g NaZSM-5 |
|---|---|---|---|
| Adsorbate Compositions | | | |
| 1.4% mX | 14.8% mX | 17.0% mX | 9.5% mX |
| 1.1% oX | 13.7% oX | 14.3% oX | 7.7% oX |
| 45.7% pX | 33.3% pX | 31.4% pX | 45.0% pX |
| 51.4% EB | 38.2% EB | 37.3% EB | 37.8% EB |

The selectivities for the small silicalite, HZSM-5 and NaZSM-5 are very similar, with the selectivity of the NaZSM-5 sample for pX being somewhat better. All of these selectivities are significantly lower than that obtained for the large crystal silicalite. These results are consistent with a crystal size effect on selectivity.

EXAMPLE 11

Selective Adsorption with TS-1 (Ti-MFI) and ZSM-22

Using the same method as given in Example 3, the adsorption capacity at 50° C. and 8 torr total $C_8$ aromatics was measured for TS-1 (Adsorbent 6) and ZSM-22 (Adsorbent 7). Both samples showed selective adsorption of pX and EB over mX and oX. Results are given in Table 13.

TABLE 13

Adsorption on TS-1 and ZSM-22
Feed is a He stream saturated with $C_8$ aromatics (oX, mX,
pX, and EB); adsorbed at 50° C. and 8 torr $C_8$ aromatics

| TS-1 (6) 58 mg adsorbate/g sieve | ZSM-22 (7) 46 mg adsorbate/g sieve |
|---|---|
| Adsorbate Compositions | |
| 3.1% mX | 4.8% mX |
| 3.3% oX | 5.4% oX |
| 42.8% pX | 39.9% pX |
| 50.8% EB | 50.0% EB |

Calculations of performance in the following examples illustrating the energy efficient performance of the crystallization process schemes illustrated in FIG. 7 and FIG. 8 and the crystallization process scheme illustrated in FIG. 9 are made according to standard engineering practices. Although the examples using the crystallization process illustrated in FIG. 9 are labeled as "comparison examples" for the purposes of showing the superiority of the crystallization schemes of FIG. 7 and FIG. 8 over that of FIG. 9, it is to be understood that the crystallization process scheme of FIG. 9 is also suitable for integration with PSA and that the present invention includes processes in which pressure swing adsorption is used to produce a para-xylene-enriched feed that is then purified by crystallization using the process illustrated in FIG. 9. For a particular comparison, the feed and the product were identical between each comparable example. Each example had three refrigeration levels available. The effluent from the coldest crystallizer was set at −5° F. in each case, ensuring that the overall para-xylene recovery for each comparable example was nearly identical. The temperature for the other two crystallization stages was chosen to shift as much duty to the warmest crystallizer while still maintaining a reasonable balance between the stages. Overriding this criterion was the need to keep the first stage of crystallizers warm enough to allow for the production of high purity product from the first set of separation devices for the designs based on FIG. 7 and FIG. 8. One would expect that keeping the first stage crystallizers at a warmer temperature would shift more refrigeration duty to the lower temperature crystallizers (which it did). One would also expect that this would increase the refrigeration compressor power requirements relative to the comparative example; however, this, unexpectedly, was not the case. The process designs of FIG. 7 and FIG. 8 required less compressor power, and this was surprising and non-obvious. This shows that the process of the present invention has the advantage of being more energy efficient, and, therefore, will also be expected to be less costly.

Example 12, Example 13, and Comparison Example 14 compare the performance of three different processes all producing 115,840 lb/hr of para-xylene product having a purity of 99.80 wt % para-xylene. Examples 12 and 13 illustrate preferred embodiments of the crystallization component of the present invention in which a portion of the total high purity para-xylene product is made from the effluent from the first crystallization without subjecting it to a reslurry step or a partial melting step, and Comparison Example 14 illustrates a less energy efficient embodiment of the invention in which the crystalline para-xylene cake from the first crystallization/separation does not go to product, but instead is combined with the crystalline para-xylene cakes from subsequent lower temperature crystallization/separation steps and subjected to a reslurry step.

For each process, a feed containing 90 wt % para-xylene is used, and the high purity para-xylene product contains 99.8 wt % para-xylene. The overall para-xylene recovery for each example is 91%. Centrifuges are used for all liquid/solid separations. When Example 12, Example 13, and Comparison Example 14 are compared, the process of Example 12 is the most energy efficient and the process of Example 13 is the next most energy efficient. The process design of Example 13, illustrated by FIG. 8, requires about 3% more refrigeration compressor power for the same production rate of 115,840 lb/hr of para-xylene product having a purity of 99.80 wt % para-xylene than the process of Example 12, whereas the process of Comparison Example 14 requires about 5% more refrigeration compressor power than the process of Example 12.

EXAMPLE 12

For this example, the operation of an embodiment of the process illustrated in the flow scheme of FIG. 7 is shown to be the most energy efficient of the three process (i.e., Example 12, Example 13, and Comparison Example 14) designs based on the power consumption of the propylene refrigeration compressor. A feed containing 90% para-xylene is cooled in crystallizer 100 to a temperature of 40.5° F. The crystallizer effluent is sent to a separation unit 30 comprising two centrifuges. The crystalline para-xylene cake is washed inside the centrifuges using high purity para-xylene material. The centrifuges produce 63,120 lb/hr of high purity product, stream 5, and two filtrate streams (streams 3 and 4). Stream 4 is the wash filtrate, and it has a greater para-xylene concentration than the reject filtrate, stream 3. All of the wash filtrate (stream 4) is sent to the reslurry drum 32 to provide some of the liquid necessary for the reslurry operation. All of the reject filtrate (stream 3) is sent to crystallizer 200. Crystallizer 200 is operated at 25° F. The effluent from crystallizer 200 is sent to a separation unit 33 comprising a centrifuge. The crystalline para-xylene cake from the centrifuge is dropped into the reslurry drum, 32, while the reject filtrate is sent via line 7 to crystallizer 300, which operates at −5° F. The effluent from this crystallizer is also sent to a separation unit 34 comprising a centrifuge. The crystalline para-xylene cake from centrifuge 34 is dropped into reslurry drum 32. The reject filtrate stream in line 10 contains about 45% para-xylene and is heat exchanged with the feed, stream 1, before being sent elsewhere in the unit. The slurry from reslurry drum 32 is sent to separation unit 31 comprising two centrifuges. The crystalline para-xylene cake is washed inside these centrifuges using high purity para-xylene material. These centrifuges produce an additional 52,720 lb/hr of high purity para-xylene product (stream 15), which is combined with the high purity para-xylene product in line 5 (stream 5), melted, and collected via line 16. Stream 14 is the wash filtrate and is more concentrated in para-xylene than the reject filtrate, stream 13. All of the wash filtrate is sent via line 14 to the reslurry drum, 32, to provide some of the liquid for the reslurry operation. About 32% of the reject filtrate is sent to the reslurry drum, 32, to provide the rest of the liquid for the reslurry operation. The reslurry drum operates at 42° F. The remaining reject filtrate from separation unit 31 is combined with stream 3 upstream of crystallizer 200 and sent to crystallizer 200. Three levels of propylene refrigeration are used in this example at pressures of about 66, 48 and 26 psia. The refrigeration compressor requires about 2707 horsepower (hp).

EXAMPLE 13

The process design illustrated by FIG. 8 requires about 3% more refrigeration compressor power for the same production rate of 115,840 lb/hr of para-xylene product having a purity of 99.80 wt % para-xylene. A feed containing 90% para-xylene (stream 102) is sent to crystallizer 150 which operates at a temperature of 40° F. The crystallizer effluent is sent to a separation unit 130 comprising three centrifuges. The crystalline para-xylene cake is washed inside the centrifuges using high purity para-xylene material. The centrifuges 130 produce 69,100 lb/hr of high purity product (stream 106), and two filtrate streams (streams 104 and 105). Stream 105 is the wash filtrate and is more concentrated in para-xylene than the reject filtrate, stream 104. All of the wash filtrate is sent to the reslurry drum 132 to provide some of the liquid necessary for the reslurry operation. All of the reject filtrate is sent to crystallizer 250. Crystallizer 250 is operated at 25° F. The effluent is sent to separation unit 133 comprising one centrifuge. The crystalline para-xylene cake from the centrifuge 133 is dropped into the reslurry drum 132 while the reject filtrate (stream 108) is sent to crystallizer 350, which operates at −5° F. The effluent from this crystallizer (stream 110) is sent to separation unit 134 comprising one centrifuge. The crystalline para-xylene cake from the centrifuge is dropped into reslurry drum 132. The reject filtrate (stream 111) contains about 45% para-xylene and is heat exchanged with feed stream 101 before being sent elsewhere in the unit. The slurry from reslurry drum 132, which comprises crystalline para-xylene and mother liquor, is sent via line 113 to a separation unit 131 comprising two centrifuges and separated. The crystalline para-xylene cake is washed inside these centrifuges using high purity para-xylene material. These centrifuges produce an additional 46,740 lb/hr of high purity product, stream 116 which is combined with product stream 106, melted, and collected via line 117. Separation unit 131 also produces two filtrate streams (streams 114 and 115). Stream 115 is the wash filtrate and is more concentrated in para-xylene than the reject filtrate, stream 114. All of the wash filtrate is sent to the reslurry drum 132 to provide some of the liquid necessary for the reslurry operation. About 6% of the reject filtrate is sent to the reslurry drum 132 to provide the rest of the liquid necessary for the reslurry operation. The reslurry drum operates at 42° F. The remaining reject filtrate (stream 114) from centrifuges 131 is combined with stream 101 upstream of crystallizer 150 to form feed stream 102. Three levels of propylene refrigeration are used in this example at pressures of about 63, 48 and 26 psia. The refrigeration compressor requires about 2791 hp, which is 3.1% higher than for the design depicted in FIG. 7.

COMPARISON EXAMPLE 14

A comparison process design in which the crystalline para-xylene cakes from the separation devices that process the effluents of all three crystallization steps are combined and subjected to a reslurry operation (illustrated in FIG. 9) requires about 5% more refrigeration compressor power than the process of Example 12 for the same production rate of 115,840 lb/hr of para-xylene product having a purity of 99.80 wt % para-xylene. A feed containing 90% para-xylene is sent to crystallizer 400 which operates at a temperature of 39.5° F. The crystallizer effluent is sent via line 203 to a separation unit 217 comprising two centrifuges. The crystalline para-xylene cake from these centrifuges is dropped via line 205 into the reslurry drum 220. The reject filtrate, stream 204, is sent to crystallizer 500 which operates at 25.5° F. The effluent from crystallizer 500 is sent via line 206 to separation unit 218 comprising one centrifuge. The crystalline para-xylene cake from separation unit 218 is dropped via line 208 into reslurry drum 220. The reject filtrate, stream 207, is sent to crystallizer 600 which operates at −5° F. The effluent from this crystallizer (stream 209) is sent to separation unit 219 comprising one centrifuge. The crystalline para-xylene cake from separation unit 219 is dropped via line 211 into reslurry drum 220. The reject filtrate (stream 210) contains about 45% para-xylene and is heat exchanged with the feed, stream 201, before being sent elsewhere in the unit. The slurry from the reslurry drum 220 is sent via line 212 to a separation unit 221 comprising four centrifuges. The crystalline para-xylene cake is washed inside these centrifuges using high purity para-xylene material. These centrifuges produce the entire 115,840 lb/hr of high purity product, stream 215. Stream 214 is the wash filtrate and is more concentrated in para-xylene than the reject filtrate, stream 213. All of the wash filtrate is sent to the reslurry drum 220 to provide some of the liquid necessary for the reslurry operation. About 82% of the reject filtrate is sent to the reslurry drum 220 via line 218 to provide the rest of the liquid necessary for the reslurry operation. The reslurry drum operates at 42° F. The remaining reject filtrate from the centrifuges is combined with feed stream 201 upstream of crystallizer 400 to form feed stream 202. Three levels of propylene refrigeration are used in this example at pressures of about 63, 48 and 26 psia. The refrigeration compressor requires about 2837 hp, which is 4.8% higher than for the design depicted in FIG. 7.

Example 15, Example 16, and Comparison Example 17 compare the performance of three different processes all producing 115,840 lb/hr of para-xylene product having a purity of 99.90 wt % para-xylene. For each process, a feed containing 90 wt % para-xylene is used. The overall para-xylene recovery for each example is 91%. The processes described in Example 15, Example 16, and Comparison Example 17 are the same as the processes described in Example 12, Example 13, and Comparison Example 14, respectively, with the exception that TNO hydraulic wash columns are used for some of the liquid/solids separations to produce the high purity para-xylene product rather than using centrifuges throughout as liquid/solid separators. Examples 15 and 16 illustrate preferred embodiments of the crystallization component of the present invention while Comparison Example 17 illustrates a less energy efficient embodiment of the invention. It can be seen that when Example 15, Example 16, and Comparison Example 17 are compared, the process of Example 15 is the most energy efficient, and the process of Example 16 is more energy efficient than the process of Comparison Example 17. The process of Example 16 requires only about 2% more refrigeration compressor power than the process of Example 15 for the same production rate of 115,840 lb/hr of para-xylene product having a purity of 99.90 wt %, whereas the process of Comparison Example 17 requires about 7% more refrigeration compressor power than the process of Example 15.

EXAMPLE 15

In this example, the operation of an embodiment of the process of the invention illustrated in the flow scheme of FIG. 7 is shown. This embodiment of the process illustrated in the flow scheme of FIG. 7 is shown to be the most energy efficient of the three process designs (i.e., Examples 15, 16, and Comparison Example 17) based on the power consumption of the propylene refrigeration compressor. A feed containing 90% para-xylene is cooled in crystallizer 100 to a temperature of 40.5° F. The crystallizer effluent is sent to separation unit 30 comprising two TNO hydraulic wash columns (see U.S. Pat. Nos. 4,734,102 and 4,735,781, incorporated herein by reference in their entireties, for descriptions of these wash columns). The wash columns produce 66,410 lb/hr of high purity product, stream 5, and a single filtrate stream, stream 3. All of stream 3 is sent to crystallizer 200. Since wash columns are used, there is no stream 4 in this embodiment. Crystallizer 200 is operated at 25° F. The effluent from crystallizer 200 is sent to a separation unit 33 comprising one centrifuge. The cake from the centrifuge 33 is dropped into reslurry drum, 32, while the reject filtrate (stream 7) is sent to crystallizer 300, which operates at −5° F. The effluent from this crystallizer is also sent to a separation unit 34 comprising one centrifuge. The cake from centrifuge 34 is dropped into reslurry drum 32. The reject filtrate (stream 10) contains about 45% para-xylene and is heat exchanged with the feed stream 1, before being sent elsewhere in the unit. The slurry from reslurry drum 32 is sent to separation unit 31 comprising one TNO hydraulic wash column. This wash column produces an additional 49,430 lb/hr of high purity product (stream 15)

About 84% of the filtrate from the wash column is sent to the reslurry drum, 32, to provide the liquid for the reslurry operation. The reslurry drum operates at 42° F. The remaining filtrate from the wash column is combined with stream 3 upstream of crystallizer 200. In this example, stream 14 does not exist. Three levels of propylene refrigeration are used in this example at pressures of about 66, 48 and 26 psia. The refrigeration compressor requires about 2670 hp.

EXAMPLE 16

Figure 1:
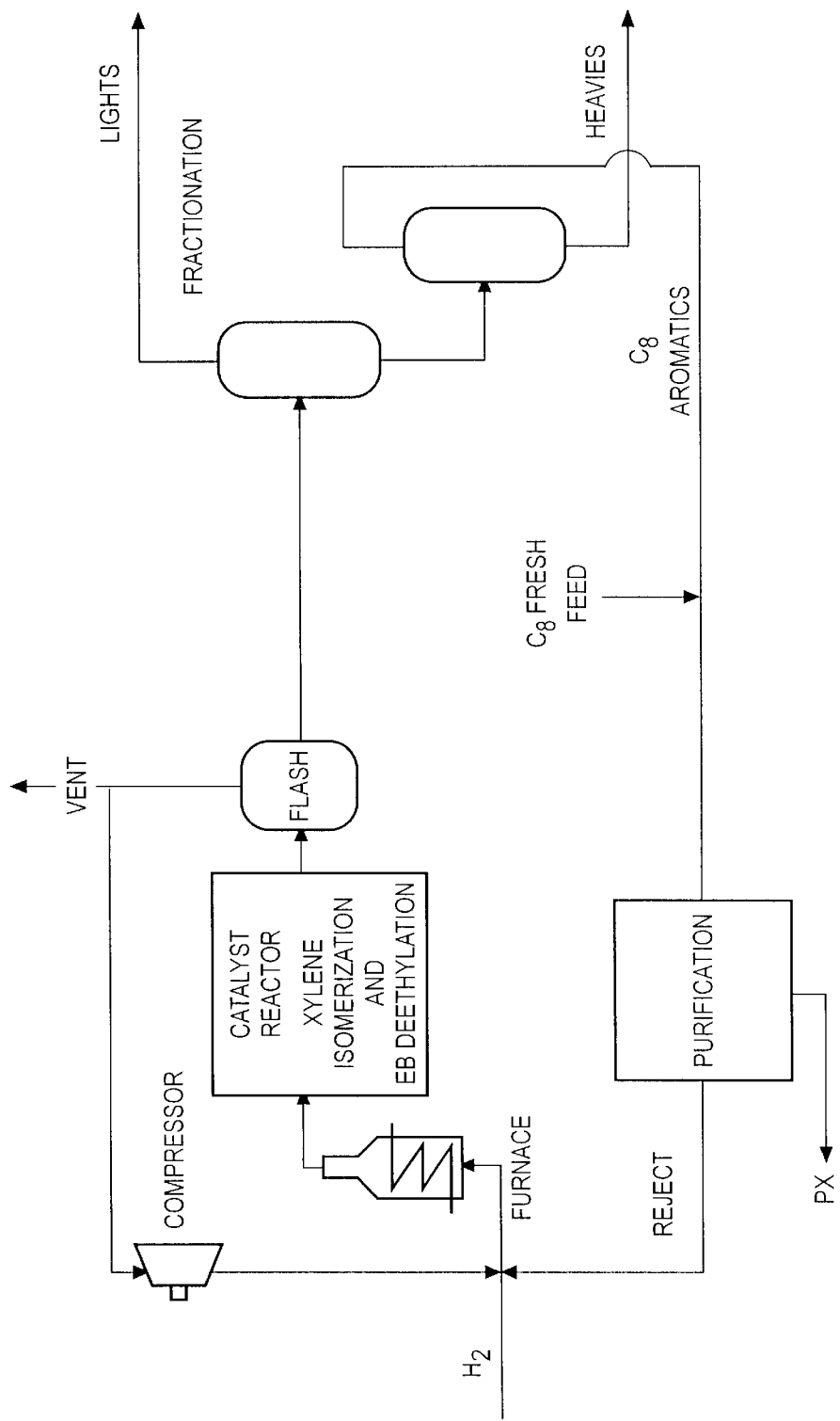
FIG. 1 is a schematic representation of the known combination of an isomerization catalyst reactor and a crystallization unit.

In this example, the operation of an embodiment of the process illustrated in the flow scheme of FIG. 8 is shown. This embodiment of the process requires about 2% more refrigeration compressor power for the same production rate of 115,840 lb/hr of para-xylene product having a purity of 99.90 wt % para-xylene. A feed containing 90% para-xylene is sent via line 102 to crystallizer 150 which operates at a temperature of 40° F. The crystallizer effluent is sent to separation unit 130 comprising three TNO hydraulic wash columns. The wash columns produce 70,040 lb/hr of high purity product, stream 106, and a single filtrate stream, stream 104, which is sent to crystallizer 250. There is no stream 105 for this particular example. Crystallizer 250 is operated at 24° F. The effluent from crystallizer 250 is sent to separation unit 133 comprising one centrifuge, and para-xylene crystals are separated from the mother liquor. The crystalline para-xylene cake from the centrifuge 133 is dropped into the reslurry drum 132 while the reject filtrate (stream 108) is sent to crystallizer 350, which operates at −5° F. The effluent from crystallizer 350 is sent to separation unit 134 comprising one centrifuge, and para-xylene crystals are separated from the mother liquor. The crystalline para-xylene cake from the centrifuge is dropped into reslurry drum 132. The reject filtrate (stream 111) contains about 45% para-xylene and is heat exchanged with the feed, stream 101, before being sent elsewhere in the unit. The slurry from reslurry drum 132 is sent to separation unit 131 comprising two TNO hydraulic wash columns. These wash columns produce an additional 45,800 lb/hr of high purity para-xylene product (stream 116) which is combined with high purity para-xylene product stream 106 and collected via line 117. About 84% of the filtrate (stream 114) from separation unit 131 is sent to the reslurry drum 132 via line 118 to provide liquid for the reslurry operation. The reslurry drum operates at 42° F. The remaining filtrate from the wash column combines via line 114 with feed stream 101 upstream of crystallizer 150. In this example, stream 115 does not exist. Three levels of propylene refrigeration are used in this example at pressures of about 63, 47 and 26 psia. The refrigeration compressor requires about 2718 hp, which is 1.8% higher than for the design depicted in FIG. 1.

COMPARISON EXAMPLE 17

A comparison process design in which the crystalline para-xylene cakes from the separation devices that process the effluents of all three crystallization steps are combined and subjected to a reslurry operation (illustrated in FIG. 9) requires about 7% more refrigeration compressor power than the design for the process of the present invention shown in Example 15 above for the same production rate of 115,840 lb/hr of para-xylene product having a purity of 99.90 wt % para-xylene. A feed containing 90% para-xylene (stream 202) is sent to crystallizer 400, which operates at a temperature of 39° F. The crystallizer effluent is sent to separation unit 217 comprising two centrifuges, and para-xylene crystals are separated from the mother liquor. The crystalline para-xylene cake from these centrifuges is dropped into the reslurry drum 220 via line 205. The reject filtrate, stream 204, is sent to crystallizer 500 which operates at 25° F. The effluent is sent via line 206 to separation unit 218 comprising one centrifuge. The crystalline para-xylene cake from separation unit 218 is dropped via line 208 into reslurry drum 220. The reject filtrate (stream 207) is sent to crystallizer 600 which operates at −5° F. The effluent from this crystallizer is sent via line 209 to separation unit 219 comprising one centrifuge. The crystalline para-xylene cake from separation unit 219 is dropped via line 211 into reslurry drum 220. The reject filtrate (stream 210) contains about 45% para-xylene and is heat exchanged with feed stream 201, before being sent elsewhere in the unit. The slurry from the reslurry drum 220 is sent via line 212 to separation unit 221 comprising three TNO hydraulic wash columns. These wash columns produce the entire 115,840 lb/hr of high purity para-xylene product, which is collected via line 215. About 90% of the filtrate from the wash columns (stream 213) is sent via line 218 to reslurry drum 220 to provide the liquid necessary for the reslurry operation. The reslurry drum operates at 42° F. The remaining filtrate from the wash columns is combined with stream 201 upstream of crystallizer 400 to form feed stream 202. In this example, stream 214 does not exist. Three levels of propylene refrigeration are used in this example at pressures of about 62, 48 and 26 psia. The refrigeration compressor requires about 2849 hp, which is 6.7% higher than for the process design of Example 16.

Example 18, Example 19, and Comparison Example 20 compare the performances of three different processes all producing 115,840 lb/hr of para-xylene product having a purity of 99.90 wt % para-xylene. The processes described in Example 18, Example 19, and Comparison Example 20 are the same as the processes described in Example 12, Example 13, and Comparison Example 14 respectively with the exception that the concentration of para-xylene in the initial feed is lower. For each process, a feed containing 70 wt % para-xylene is used. The overall para-xylene recovery for each example is 69%. Examples 18 and 19 illustrate preferred embodiments of the crystallization component of the present invention while Comparison Example 20 illustrates a less energy efficient embodiment of the invention. It can be seen that when Example 18, Example 19, and Comparison Example 20 are compared, the process of Example 19 is the most energy efficient and the process of Example 18 is the next most energy efficient. For the process embodiment of Example 18, the refrigeration compressor requires about 4884 hp, which is 8.9% greater than that needed for the process of Example 19. For the process of Comparison Example 20, the refrigeration compressor requires about 5178 hp, which is 15.5% higher than for the process of Example 6 and 6.0% higher than for the process of Example 18.

EXAMPLE 18

In this example of an embodiment of the invention, the process embodiment illustrated by the flow scheme of FIG. 7 is shown to require about 9% more refrigeration compressor power than the process embodiment design depicted in FIG. 8. A feed containing 70% para-xylene is cooled in crystallizer 100 to a temperature of 22° F. The crystallizer effluent, which comprises para-xylene crystals and mother liquor, is sent to separation unit 30 comprising four TNO hydraulic wash columns. The wash columns produce 51,940 lb/hr of high purity product (stream 5) and a single filtrate stream (stream 3). In this embodiment, all of stream 3 is sent via line 3 to crystallizer 200. Since wash columns are used, there is no stream 4 for this particular example. Crystallizer 200 is operated at 14° F. The effluent is sent via line 6 to separation unit 33 comprising three centrifuges where the crystalline para-xylene is separated from the mother liquor. The crystalline para-xylene cake from the centrifuges is dropped into the reslurry drum, 32, while the reject filtrate is sent via line 7 to crystallizer 300, which operates at −5° F. The effluent from crystallizer 300 which comprises crystalline para-xylene and mother liquor is sent to separation unit 34 comprising two centrifuges for separation. The crystalline para-xylene cake from the centrifuges is dropped into reslurry drum 32. The reject filtrate (stream 10) contains about 42% para-xylene and is heat exchanged with the feed (stream 1) before being sent elsewhere in the unit. The slurry from reslurry drum 32 is sent to separation unit 31 comprising two TNO hydraulic wash columns. These wash columns produce an additional 63,900 lb/hr of high purity para-xylene product, stream 15, which is combined with high purity para-xylene product stream 5 and collected in line 16. About 29% of the filtrate from the wash column 31 is sent to the reslurry drum 32 to provide liquid for the reslurry operation. The reslurry drum operates at 42° F. The remaining filtrate from the wash column 31 is combined with stream 3 upstream of crystallizer 200. In this example, stream 14 does not exist. Three levels of propylene refrigeration are used in this example at pressures of about 47, 39 and 26 psia. The refrigeration compressor requires about 4884 hp, which is 8.9% greater than that needed for the design depicted in Example 19 (FIG. 8).

EXAMPLE 19

In this example of an embodiment of the invention, the process embodiment illustrated by the flow scheme of FIG. 8 is shown to be the least energy intensive of the three designs (Example 18, Example 19, and Comparison Example 20) based on the power consumption of the propylene refrigeration compressor for this example. A feed containing 70% para-xylene is sent to crystallizer 150 which operates at a temperature of 24° F. The crystallizer effluent, which comprises crystalline para-xylene and mother liquor, is sent to separation unit 130 comprising three TNO hydraulic wash columns. The wash columns produce 68,350 lb/hr of high purity product (stream 106) and a single filtrate stream (stream 104) which is sent via line 104 to crystallizer 250. There is no stream 105 for this particular example. Crystallizer 250 is operated at 1° F. The effluent from crystallizer 250 is sent to separation unit 133 comprising three centrifuges. The crystalline para-xylene cake from the centrifuges is dropped into the reslurry drum 132, while the reject filtrate is sent via line 108 to crystallizer 350, which operates at −5° F. The effluent from this crystallizer is sent to separation unit 134 comprising two centrifuges. The crystalline para-xylene cake from the centrifuges is dropped into reslurry drum 132. The reject filtrate, stream 111, contains about 42% para-xylene and is heat exchanged with the feed, stream 101, before being sent elsewhere in the unit. The slurry from reslurry drum 132 is sent to separation unit 131 comprising a TNO hydraulic wash column. This wash column produces an additional 47,490 lb/hr of high purity para-xylene product, stream 116, which is combined with high purity para-xylene product stream 106 and collected via line 117. About 34% of the filtrate from the wash column (stream 114) is sent to the reslurry drum 132 to provide liquid for the reslurry operation. The reslurry drum operates at 42° F. The remaining filtrate from the wash column 131 is combined with stream 101 upstream of crystallizer 150 to form stream 102. In this example, stream 115 does not exist. Three levels of propylene refrigeration are used in this example at pressures of about 47, 36 and 26 psia. The refrigeration compressor requires about 4483 hp.

COMPARISON EXAMPLE 20

A comparison process design, in which the crystalline para-xylene cakes from the separation devices that process the effluents of all three crystallization steps are combined and subjected to a reslurry operation (illustrated in FIG. 9), requires about 16% more refrigeration compressor power than the process of Example 19 for the same production rate of 115,840 lb/hr of para-xylene product having a purity of 99.90 wt % para-xylene. A feed containing 70% para-xylene (stream 202) is sent to crystallizer 400 which operates at a temperature of 25° F. The crystallizer effluent, which comprises crystalline para-xylene and mother liquor, is sent to separation unit 217 comprising three centrifuges. The crystalline para-xylene cake from these centrifuges is dropped via line 205 into the reslurry drum 220. The reject filtrate (stream 204) is sent to crystallizer 500 which operates at 13° F. The effluent of para-xylene crystals and mother liquor from crystallizer 500 is sent to separation unit 218 comprising three centrifuges. The crystalline para-xylene cake from the centrifuges is dropped via line 208 into reslurry drum 220. The reject filtrate (stream 207) is sent to crystallizer 600 which operates at −5° F. The effluent from crystallizer 600 is sent to separation unit 219 comprising two centrifuges. The crystalline para-xylene cake from the centrifuges is dropped via line 211 into reslurry drum 220. The reject filtrate (stream 210) contains about 42% para-xylene and is heat exchanged with the feed, stream 201, before being sent elsewhere in the unit. The slurry from the reslurry drum 220 is sent to separation unit 221 comprising three TNO hydraulic wash columns. These wash columns produce the entire 115,840 lb/hr of high purity para-xylene product which is collected via line 215. About 45% of the filtrate from the wash columns (stream 213) is sent via line 218 to the reslurry drum 220 to provide liquid for the reslurry operation. The reslurry drum operates at 42° F. The remaining filtrate from the wash columns is combined with stream 201 upstream of crystallizer 400. In this example, stream 214 does not exist. Three levels of propylene refrigeration are used in this example at pressures of about 48, 38 and 26 psia. The refrigeration compressor requires about 5178 hp, which is 15.5% higher than for the design depicted in Example 20 (FIG. 8) and 6.0% higher than for the design depicted in Example 18 (FIG. 7).

EXAMPLE 21

This example illustrates that the pX-depleted stream gives lower xylene loss in the isomerization reactor, which increases the overall yield of pX for the unit."

A comparison was done for a xylene isomerization catalyst run with a mixed xylene feed containing 10 wt % pX and a mixed xylene feed containing 1 wt % pX. The catalyst was an aluminosilicate/borosilicate catalyst system with a molybdenum hydrogenation metal. Such catalysts are described in EP 0 923 512 incorporated herein by reference in its entirety. Results in Table 14 below show that xylene loss decrease when the amount of pX in the feed is reduced.

TABLE 14

|  | Feed A | Feed B |
|---|---|---|
| wt % pX in feed | 1% | 10% |
| % Xylene Loss at 50% EB conversion | 0.7 | 1.1 |
| % Xylene Loss at 80% EB conversion | 1.8 | 2.3 |

That which is claimed is:

1. A process for separating and recovering para-xylene from a gaseous mixture comprising $C_8$ aromatic hydrocarbons, the process comprising:
   (a) introducing a gaseous mixture comprising meta-xylene, ortho-xylene, para-xylene, and ethylbenzene into a pressure swing adsorption unit and subjecting the mixture to pressure swing adsorption under substantially isothermal conditions using an adsorbent comprising a para-selective adsorbent capable of selectively adsorbing para-xylene at a temperature and pressure at which at least 0.01 grams of para-xylene and ethylbenzene are adsorbed per gram of adsorbent to produce a meta-xylene and ortho-xylene-rich effluent stream comprising a mixture of ortho-xylene and meta-xylene, which contains no more than a total of about 25 mole percent of para-xylene and ethylbenzene based on total $C_8$ aromatics, and a para-xylene-rich effluent stream comprising para-xylene and ethylbenzene, which contains no more than a total of about 50 mole percent of meta-xylene and ortho-xylene based on total $C_8$ aromatics;
   (b) sending at least a portion of the para-xylene-rich stream to a crystallization unit and crystallizing said para-xylene-rich stream to produce a para-xylene product stream and a para-xylene-lean mother liquor stream;
   (c) sending at least a portion of the meta-xylene and ortho-xylene-rich stream to an isomerization unit and isomerizing said stream to produce an isomerizate comprising an equilibrium mixture of xylenes;
   (d) recycling at least a portion of the isomerizate from step (c) to step (a);
   (e) sending at least a portion of the para-xylene-lean mother liquor stream from step (b) to an isomerization unit and isomerizing said stream to produce an isomerizate comprising an equilibrium mixture of xylenes; and
   (f) recycling at least a portion of the isomerizate from step (e) to step (a).

2. The process of claim 1 wherein the gaseous mixture comprising meta-xylene, ortho-xylene, para-xylene, and ethylbenzene is contacted with an ethylbenzene conversion catalyst to remove at least a portion of the ethylbenzene prior to being subjected to pressure swing adsorption in step (a).

3. The process of claim 1 wherein at least a portion of the para-xylene-lean mother liquor stream from step (b) is contacted with an ethylbenzene conversion catalyst to remove at least a portion of any ethylbenzene in the para-xylene-lean mother liquor stream and to produce an ethylbenzene-lean effluent which is then recycled to step (a).

4. A process for separating and recovering para-xylene from a gaseous mixture comprising $C_8$ aromatic hydrocarbons, the process comprising:
   (a) introducing a gaseous mixture comprising meta-xylene, ortho-xylene, para-xylene, and ethylbenzene into a pressure swing adsorption unit and subjecting the mixture to pressure swing adsorption under substantially isothermal conditions using an adsorbent comprising a para-selective adsorbent capable of selectively adsorbing para-xylene at a temperature and pressure at which at least 0.01 grams of para-xylene and ethylbenzene are adsorbed per gram of adsorbent to produce a meta-xylene and ortho-xylene-rich effluent stream comprising a mixture of ortho-xylene and meta-xylene, which contains no more than a total of about 25 mole percent of para-xylene and ethylbenzene based on total $C_8$ aromatics, and a para-xylene-rich effluent stream comprising para-xylene and ethylbenzene, which contains no more than a total of about 50 mole percent of meta-xylene and ortho-xylene based on total $C_8$ aromatics;
   (b) sending at least a portion of the para-xylene-rich stream to a crystallization unit and crystallizing said para-xylene-rich stream to produce a para-xylene product stream and a para-xylene-lean mother liquor stream;
   (c) sending at least a portion of the meta-xylene and ortho-xylene-rich stream to an isomerization unit and isomerizing said stream to produce an isomerizate comprising an equilibrium mixture of xylenes;
   (d) recycling at least a portion of the isomerizate from step (c) to step (a);
   (e) sending at least a portion of the para-xylene-lean mother liquor stream from step (b) to an ethylbenzene conversion unit and contacting it with an ethylbenzene conversion catalyst to remove at least a portion of any ethylbenzene in the para-xylene-lean mother liquor stream and to produce an ethylbenzene-lean effluent; and
   (f) combining at least a portion of the ethylbenzene-lean effluent produced in step (e) with the isomerizate from step (c) and recycling the combined effluents to step (a).

5. The process of claim 1 wherein the adsorbent used in the pressure swing adsorption of step (a) comprises a para-selective, non-acidic molecular sieve.

6. The process of claim 1 wherein the adsorbent used in the pressure swing adsorption of step (a) comprises a para-selective, non-acidic, medium pore molecular sieve.

7. The process of claim 6 wherein the molecular sieve used in the pressure swing adsorption of step (a) comprises orthorhombic crystals of silicalite having an average minimum dimension of at least about 0.2 $\mu$m.

8. The process of claim 1 wherein the pressure swing adsorption in step (a) is operated at a temperature of at least about 350° F. and a pressure of at least about 30 psia.

9. The process of claim 1 wherein the pressure swing adsorption in step (a) is operated at a temperature of from about 350° F. to about 750° F. and a pressure of from about 30 psia to about 400 psia.

10. The process of claim 1 wherein the pressure swing adsorption in step (a) is operated at a temperature of from about 400° F. to about 650° F. and a pressure of from about 50 psia to about 300 psia.

11. The process of claim 1 wherein the crystallization in step (b) is conducted in at least one crystallization stage at a temperature of from about −50° F. to about −130° F.

12. The process of claim 11 wherein the crystallization is conducted in at least two crystallization stages wherein each successive crystallization stage is operated at a temperature lower than the preceding crystallization stage.

13. The process of claim 1 wherein the para-xylene product stream produced in step (b) comprises impure crystalline para-xylene which is purified by contacting the impure crystalline para-xylene with para-xylene-containing liquid at a temperature sufficient to produce a first slurry mixture, separating the first slurry mixture in a first separation apparatus to produce a first mother liquor and an intermediate purity crystalline para-xylene product, melting the intermediate purity crystalline para-xylene product to produce intermediate purity liquid para-xylene, crystallizing the intermediate purity liquid para-xylene in a crystallization apparatus to produce a second mixture comprising crystalline para-xylene and liquid para-xylene, and separating the second mixture in a second separation apparatus to produce a second mother liquor and purified crystalline para-xylene product.

14. The process of claim 13 wherein the first slurry mixture is at a temperature of about −20° F. to about 20° F.; the crystallizing of the intermediate purity liquid para-xylene is at a temperature of about 20° F. to about 45° F.;

the purified crystalline para-xylene in the second separation apparatus is washed with liquid para-xylene;

at least a portion of the mother liquor from the second separation apparatus is directed to the first slurry mixture; and at least a portion of liquid para-xylene wash filtrate from the second separation apparatus is directed to the crystallization apparatus.

15. The process of claim 1 wherein the para-xylene product stream produced in step (b) comprises impure crystalline para-xylene which is purified to a purity of at least about 99.5 weight percent by contacting the impure crystalline para-xylene with para-xylene-containing liquid at a temperature sufficient to produce a first slurry mixture, separating the first slurry mixture in a first separation apparatus to produce a first mother liquor and an intermediate purity crystalline para-xylene product, contacting the intermediate purity crystalline para-xylene product with para-xylene containing liquid at a temperature sufficient to produce a second slurry mixture, and separating the second slurry mixture in a second separation apparatus to produce a second mother liquor and purified crystalline para-xylene product.

16. The process of claim 15 wherein the first slurry mixture is at a temperature of about −20° F. to about 20° F.;

the contacting of the intermediate purity crystalline para-xylene product with para-xylene-containing liquid to produce the second slurry mixture is at a temperature of about 35° F. to about 45° F.; and the purified crystalline para-xylene in the second separation apparatus is washed with liquid para-xylene.

17. The process of claim 16 wherein at least a portion of liquid para-xylene filtrate from the second separation apparatus is directed to the first slurry mixture and at least a portion of the liquid para-xylene filtrate from the second separation apparatus is directed to the second slurry mixture.

18. The process of claim 1 wherein the para-xylene product stream produced in step (b) comprises impure crystalline para-xylene which is purified by contacting the impure crystalline para-xylene with para-xylene-containing liquid at a temperature sufficient to produce a first slurry mixture, separating the first slurry mixture in a first separation apparatus to produce a first mother liquor and a purified crystalline para-xylene product, crystallizing the first mother liquor in a crystallization apparatus to produce a crystallization mixture comprising crystalline para-xylene and liquid para-xylene separating the crystallization mixture in a second separation apparatus to produce an intermediate purity crystalline para-xylene and a second mother liquor, and directing the intermediate purity crystalline para-xylene to the first slurry mixture.

19. The process of claim 18 wherein the temperature of the slurry is about 35° F. to about 45° F. and the crystallization is conducted at a temperature of about −70° F. to about 25° F.

20. The process of claim 1, wherein the para-xylene-rich effluent stream produced by pressure swing adsorption in step (a) contains at least about 60 weight percent of para-xylene.

21. The process of claim 20 wherein, the para-xylene-rich effluent stream comprising at least about 60 weight percent para-xylene produced in step (a) is subjected to crystallization in step (b) to obtain a para-xylene product stream by a crystallization process comprising:

aa) crystallizing said para-xylene-rich stream in a first crystallizer at a temperature of about 10° F. to about 55° F.;

bb) recovering an effluent from the first crystallizer comprising para-xylene crystals in a first mother liquor;

cc) separating the para-xylene crystals from the first mother liquor in a first separation unit, washing the para-xylene crystals with liquid para-xylene, completely melting the para-xylene crystals, and collecting the liquid para-xylene product;

dd) transferring at least a portion of filtrate from the first separation unit to a second crystallizer, which is operated at a temperature lower than that of the first crystallizer, crystallizing the filtrate, and recovering an effluent from the second crystallizer comprising para-xylene crystals in a second mother liquor;

ee) separating the para-xylene crystals from the second mother liquor in a second separation unit and sending the para-xylene crystals to a slurry apparatus;

ff) transferring and crystallizing at least a portion of filtrate from the second separation unit in a third crystallizer, which is operated at a temperature lower than that of the second crystallizer, and recovering an effluent from the third crystallizer comprising para-xylene crystals in a third mother liquor;

gg) separating the para-xylene crystals from the third mother liquor in a third separation unit and sending the para-xylene crystals to the slurry apparatus;

hh) contacting the para-xylene crystals in the slurry apparatus with para-xylene-containing liquid to form a slurry mixture having a temperature higher than that of the lowest temperature of any of the crystallizers;

ii) separating the slurry mixture in a fourth separation unit to produce a filtrate and a crystalline para-xylene product, washing the para-xylene crystals with liquid para-xylene, completely melting the para-xylene crystals, and collecting the liquid para-xylene product;

jj) recycling at least a portion of filtrate from the fourth separation unit to the second crystallizer; and kk) recycling at least another portion of filtrate selected from the group consisting of filtrate from the first separation unit, filtrate from the fourth separation unit, and filtrate from the first and fourth separation units to the slurry apparatus.

22. The process of claim 21 wherein the first crystallizer is operated at a temperature of about 30° F. to about 55° F., the second crystallizer is operated at a temperature of about −10° F. to about 35° F., the third crystallizer is operated at a temperature of about −35° F. to about 5° F., and the temperature of the slurry mixture in step (hh) is about 10° F. to about 55° F°.

23. The process of claim 21 wherein the first crystallizer is operated at a temperature of about 35° F. to about 45° F., the second crystallizer is operated at a temperature of about 15° F. to about 25° F., the third crystallizer is operated at a temperature of about −10° F. to about −5° F., and the temperature of the slurry mixture in step (hh) is about 30° F. to about 50° F.° F.

24. The process of claim 21 wherein the first crystallizer is operated at a temperature of about 35° F. to about 45° F., the second crystallizer is operated at a temperature of about 15° F. to about 25° F., the third crystallizer is operated at a temperature of about −10° F. to about −5° F., the temperature of the slurry mixture in step (hh) is about 38° F. to about 42° F. ° F.; and the slurry mixture in step (hh) comprises about 30 to abut 60 weight percent crystalline para-xylene.

25. The process of claim 1, wherein the para-xylene-rich effluent stream produced by pressure swing adsorption in step (a) contains at least about 55 weight percent of para-xylene.

26. The process of claim 25 wherein, the para-xylene-rich effluent stream comprising at least about 55 weight percent para-xylene produced in step (a) is subjected to crystallization in step (b) to obtain a para-xylene product stream by a crystallization process comprising:

aa) crystallizing said feedstream in a first crystallizer at a temperature of about 10° F. to about 55° F.;

bb) recovering an effluent from the first crystallizer comprising para-xylene crystals in a first mother liquor;

cc) separating the para-xylene crystals from the first mother liquor in a first separation unit, washing the para-xylene crystals with liquid para-xylene, completely melting the para-xylene crystals, and collecting the liquid para-xylene product;

dd) transferring at least a portion of filtrate from the first separation unit to a second crystallizer which is operated at a temperature lower than that of the first crystallizer, crystallizing the filtrate, and recovering an effluent from the second crystallizer comprising para-xylene crystals in a second mother liquor;

ee) separating the para-xylene crystals from the second mother liquor in a second separation unit and sending the para-xylene crystals to a slurry apparatus;

ff) transferring and crystallizing at least a portion of filtrate from the second separation unit in a third crystallizer, which is operated at a temperature lower than that of the second crystallizer, and recovering an effluent from the third crystallizer comprising para-xylene crystals in a third mother liquor;

gg) separating the para-xylene crystals from the third mother liquor in a third separation unit and sending the para-xylene crystals to the slurry apparatus;

hh) contacting the para-xylene crystals in the slurry apparatus with para-xylene-containing liquid to form a slurry mixture having a temperature higher than that of the lowest temperature of any of the crystallizers;

ii) separating the slurry mixture in a fourth separation unit to produce a filtrate and a crystalline para-xylene product, washing the para-xylene crystals with liquid para-xylene, completely melting the para-xylene crystals, and collecting the liquid para-xylene product;

jj) recycling at least a portion of filtrate from the fourth separation unit to the first crystallizer; and kk) recycling at least another portion of filtrate selected from the group consisting of filtrate from the first separation unit, filtrate from the fourth separation unit, and filtrate from the first and fourth separation units to the slurry apparatus.

27. The process of claim 26 wherein the first crystallizer is operated at a temperature of about 10° F. to about 55° F., the second crystallizer is operated at a temperature of about −10° F. to about 35° F., the third crystallizer is operated at a temperature of about −35° F. to about 5° F., and the temperature of the slurry mixture in step (hh) is about 10° F. to about 55° F.

28. The process of claim 26 wherein the first crystallizer is operated at a temperature of about 20° F. to about 30° F., the second crystallizer is operated at a temperature of about 5° F. to about 15° F., the third crystallizer is operated at a temperature of about −10° F. to about −5° F., and the temperature of the slurry mixture in step (hh) is about 30° F. to about 50° F.° F.

29. The process of claim 26 wherein the first crystallizer is operated at a temperature of about 20° F. to about 30° F., the second crystallizer is operated at a temperature of about 5° F. to about 15° F., the third crystallizer is operated at a temperature of about −10° F. to about −5° F., the temperature of the slurry mixture in step (hh) is about 35° F. to about 45° F.°; and the slurry mixture in step (hh) comprises about 30 to about 60 weight percent crystalline para-xylene.

30. The process of claim 1 wherein the pressure swing adsorption in step (a) comprises a pressure swing adsorption process for separating para-xylene and ethylbenzene from a feed comprising a gaseous mixture comprising $C_8$ aromatics containing para-xylene, ethylbenzene, meta-xylene and ortho-xylene under substantially isothermal conditions comprising:

(1a) adsorbing the mixture onto an adsorbent comprising a para-selective adsorbent capable of selectively adsorbing para-xylene and ethylbenzene at a temperature and pressure at which at least 0.01 grams of para-xylene and ethylbenzene may be adsorbed per gram of adsorbent;

(1b) producing a first effluent stream comprising a mixture of ortho-xylene and meta-xylene, which contains no more than a total of about 25 mole percent para-xylene and ethylbenzene based on total $C_8$ aromatics;

(1c) selectively removing any feed present in non-selective voids of the adsorbent, the adsorbent vessel, and between adsorbent particles;

(1d) selectively desorbing para-xylene and ethylbenzene by decreasing partial pressure of para-xylene and ethylbenzene; and (1e) collecting a stream comprising para-xylene and ethylbenzene which contains no more than a total of about 50 mole percent of meta-xylene and ortho-xylene based on total $C_8$ aromatics.

31. The process of claim 30 wherein the adsorbent comprises a para-selective, non-acidic, medium pore molecular sieve, the temperature is from about 350° F. to about 750° F., and the pressure is from about 30 psia to about 400 psia.

32. The process of claim 30 wherein the mixture of ortho-xylene and meta-xylene produced in step (1b) contains no more than a total of about 15 mole percent of para-xylene and ethylbenzene based on total $C_8$ aromatics, and the stream containing para-xylene and ethylbenzene collected in step (1e) contains no more than a total of about 25 mole percent of meta-xylene and ortho-xylene based on total $C_8$ aromatics.

33. The process of claim 1 wherein the pressure swing adsorption in step (a) comprises a pressure swing adsorption process for separating para-xylene and ethylbenzene from a feed comprising a gaseous mixture comprising $C_8$ aromatics containing para-xylene, ethylbenzene, meta-xylene and ortho-xylene under substantially isothermal conditions comprising:

(1a) providing an adsorbent bed comprising a para-selective adsorbent which exhibits capacity to selectively adsorb and desorb para-xylene and ethylbenzene under substantially isothermal conditions at operating pressure, disposed in a vessel having at least one inlet and at least one outlet such that gas entering an inlet passes through the adsorbent bed to an outlet, and containing a purge gas substantially free of $C_8$ aromatic compounds;

(1b) flowing a gaseous feed mixture comprising xylenes and ethylbenzene into the adsorbent bed through one or more of the vessel inlets, and collecting effluent from one or more of the outlets and segregating at least a fraction of the purge gas substantially free of $C_8$ aromatic compounds while selectively adsorbing para-xylene and ethylbenzene from the gaseous feed mixture under substantially isothermal conditions in the bed;

(1c) collecting from one or more of the outlets a first effluent product comprising m-xylene and o-xylene which contains no more than a total of about 25 mole percent of para-xylene and ethylbenzene based on total $C_8$ aromatics;

(1d) replacing the feed mixture flowing into the adsorbent bed though one or more inlets with the purge gas while maintaining substantially isothermal conditions in the adsorbent bed, and collecting from one or more of the outlets an effluent gaseous mixture until effluent at the outlet contains no more than a total of about 50 mole percent of m-xylene and o-xylene based on total $C_8$ aromatics;

(1e) collecting from one or more of the outlets a second effluent product comprising ethylbenzene and para-xylene which contains no more than a total of about 50 mole percent of m-xylene and o-xylene based on total $C_8$ aromatics; and (1f) repeating steps (1b) through (1e).

34. The process of claim 33 wherein the adsorbent comprises a para-selective, non-acidic, medium pore molecular sieve, the temperature is from about 350° F. to about 750° F., the pressure is from about 30 psia to about 400 psia, and the purge gas is selected from the group consisting of $C_1$–$C_4$ alkanes, He, $CO_2$, hydrogen, nitrogen, argon and mixtures thereof.

35. The process of claim 33 wherein the mixture of ortho-xylene and meta-xylene produced in step (1b) contains no more than a total of about 15 mole percent of para-xylene and ethylbenzene based on total $C_8$ aromatics, and the stream containing para-xylene and ethylbenzene collected in step (1e) contains no more than a total of about 25 mole percent of meta-xylene and ortho-xylene based on total $C_8$ aromatics.

36. The process of claim 33 wherein the steps (1b) through (1e) are carried out under substantially isothermal conditions at temperatures in a range upward from about 350° F., wherein steps (1b) through (1e) are carried out under constant pressure at a pressure of at least about 30 psia, and wherein steps (1b) through (1e) are repeated with a cycle time of from about 2 minutes to about 200 minutes.

37. The process of claim 33 wherein at least a portion of the effluent gaseous mixture collected in step (1d) is admixed with the gaseous feed mixture in subsequent cycles.

38. The process of claim 33 wherein the purge gas comprises hydrogen, and wherein steps (1b) through (1e) are repeated with a cycle time of from about 3 minutes to about 30 minutes under substantially isothermal conditions at a temperature of about 350° F. to about 750° F. and at constant operating pressure at a pressure of at least about 30 psia.

39. The process of claim 33 wherein the flow of said purge gas is counter current to the flow of said gaseous feed mixture.

40. The process of claim 1 wherein the pressure swing adsorption in step (a) comprises a pressure swing adsorption process for separating para-xylene and ethylbenzene from a feed comprising a gaseous mixture comprising $C_8$ aromatics containing para-xylene, ethylbenzene, meta-xylene and ortho-xylene under substantially isothermal conditions comprising:

(1a) providing an adsorbent bed comprising a para-selective adsorbent which exhibits capacity to selectively adsorb and desorb para-xylene and ethylbenzene under substantially isothermal conditions at operating pressure, disposed in a vessel having at least one inlet and at least one outlet such that gas entering an inlet passes through the particulate bed to an outlet and pressurizing the vessel with a mixture comprising meta-xylene and ortho-xylene to a preselected pressure for adsorption;

(1b) flowing a gaseous feed mixture comprising xylene isomers and ethylbenzene into the adsorbent bed through one or more inlets and displacing the meta-xylene and ortho-xylene in the vessel while selectively adsorbing ethylbenzene and para-xylene from the gaseous feed mixture under substantially isothermal conditions in the adsorbent bed;

(1c) collecting from one or more of the outlets a first effluent product comprising meta-xylene and ortho-xylene which contains no more than a total of about 25 mole percent of ethylbenzene and para-xylene based on total $C_8$ aromatics while maintaining substantially isothermal conditions in the adsorbent bed and the flow of feed at the pressure for adsorption;

(1d) replacing the feed mixture flowing into the bed though one or more inlets with a purge gas comprising para-xylene and ethylbenzene substantially free of meta-xylene and ortho-xylene while maintaining the pressure for adsorption and substantially isothermal conditions in the bed, and collecting from one or more of the outlets a gaseous mixture comprising feed;

(1e) reducing the pressure to desorb ethylbenzene and para-xylene while maintaining substantially isothermal conditions in the bed; and (1f) collecting a second effluent product comprising ethylbenzene and para-xylene which contains no more than a total of about 50 mole percent of meta-xylene and ortho-xylene based on total $C_8$ aromatics.

41. The process of claim 40 wherein the flow of said para-xylene and ethylbenzene purge gas is countercurrent to the flow of the gaseous feed mixture.

42. The process of claim 40 wherein the para-xylene and ethylbenzene effluent flow during depressurization is countercurrent to the flow of the gaseous feed mixture.

43. The process of claim 40 wherein the flow of meta-xylene and ortho-xylene to pressurize the vessel is countercurrent to the feed gas flow.

44. The process of claim 1 wherein the pressure swing adsorption in step (a) comprises a pressure swing adsorption process for separating para-xylene and ethylbenzene from a feed comprising a gaseous mixture comprising $C_8$ aromatics containing para-xylene, ethylbenzene, meta-xylene and ortho-xylene under substantially isothermal conditions comprising:

(1a) providing at least two adsorbent beds containing an adsorbent comprising a para-selective adsorbent which exhibits capacity to selectively adsorb and desorb para-xylene and ethylbenzene under substantially isothermal conditions at operating pressure, disposed in connected vessels, each having at least one inlet and at least one outlet such that gas entering an inlet passes through the particulate bed to an outlet, and pressurizing a first vessel with a mixture comprising meta-xylene and ortho-xylene to a preselected pressure for adsorption;

(1b) flowing a gaseous feed mixture comprising xylene isomers and ethylbenzene into the adsorbent bed in the first vessel though one or more inlets and displacing the meta-xylene and ortho-xylene in the vessel while selectively adsorbing ethylbenzene and para-xylene from the gaseous feed mixture under substantially isothermal conditions in the adsorbent bed;

(1c) collecting from one or more of the outlets a first effluent product comprising meta-xylene and ortho-xylene which contains no more than a total of about 25 mole percent of ethylbenzene and para-xylene based on total $C_8$ aromatics while maintaining substantially isothermal conditions in the adsorbent bed and the flow of feed at the pressure for adsorption;

(1d) stopping the flow of feed and reducing the pressure in the first vessel sufficiently to permit removal of at least a portion of the feed from non-selective voids while maintaining substantially isothermal conditions in the bed by equalizing the pressure in the first vessel with the pressure in the second vessel which is at a lower pressure;

(1e) further reducing the pressure in the first vessel to desorb ethylbenzene and para-xylene while maintaining substantially isothermal conditions in the bed; and (1f) collecting a second effluent product comprising ethylbenzene and para-xylene which contains no more than a total of about 50 mole percent of meta-xylene and ortho-xylene based on total $C_8$ aromatics.

45. The process of claim 44 wherein, following step (1f), a purge gas comprising meta-xylene and ortho-xylene is added to the first vessel to displace para-xylene and ethylbenzene in the non-selective voids, and an effluent comprising the para-xylene and ethylbenzene is collected.

46. The process of claim 44 wherein prior to step (1d) a rinse comprising para-xylene and ethylbenzene is introduced into the vessel to displace meta-xylene and ortho-xylene in non-selective voids.

47. The process of claim 1 wherein the pressure swing adsorption in step (a) comprises a pressure swing adsorption process for separating para-xylene and ethylbenzene from a feed comprising a gaseous mixture comprising $C_8$ aromatics containing para-xylene, ethylbenzene, meta-xylene and ortho-xylene under substantially isothermal conditions comprising:

(1a) providing an adsorbent bed comprising a para-selective adsorbent which exhibits capacity to selectively adsorb and desorb para-xylene and ethylbenzene under substantially isothermal conditions at operating pressure, disposed in a vessel having at least one inlet and at least one outlet such that gas entering an inlet passes through the particulate bed to an outlet and pressurizing the vessel with a mixture comprising meta-xylene and ortho-xylene to a preselected pressure for adsorption;

(1b) flowing a gaseous feed mixture comprising xylene isomers and ethylbenzene into the adsorbent bed though one or more inlets and displacing the meta-xylene and ortho-xylene in the vessel while selectively adsorbing ethylbenzene and para-xylene from the gaseous feed mixture under substantially isothermal conditions in the adsorbent bed;

(1c) collecting from one or more of the outlets a first effluent product comprising meta-xylene and ortho-xylene which contains no more than a total of about 25 mole percent of ethylbenzene and para-xylene based on total $C_8$ aromatics while maintaining substantially isothermal conditions in the adsorbent bed and the flow of feed at the pressure for adsorption;

(1d) stopping the flow of feed and reducing operating pressure to a pressure at which para-xylene and ethylbenzene desorb while maintaining substantially isothermal conditions in the bed; and (1e) collecting a second effluent product comprising ethylbenzene and para-xylene which contains no more than a total of about 50 mole percent of meta-xylene and ortho-xylene based on total $C_8$ aromatics.

48. The process of claim 47 wherein, following step (1e), a purge gas of meta-xylene and ortho-xylene is added to the first vessel to displace para-xylene and ethylbenzene in the non-selective voids, and an effluent comprising the para-xylene and ethylbenzene is collected.

49. The process of claim 6 wherein the para-selective, non-acidic medium pore molecular sieve is selected from the group of molecular sieve structure types consisting of MFI, TON, MTT, EUO, MEL, and FER.

50. The process of claim 30 wherein the adsorbent used in the pressure swing adsorption in step (1a) comprises a para-selective, non-acidic, medium pore molecular sieve, and wherein the pressure swing adsorption in step (1a) is operated at a temperature of at least about 350° F. and a pressure of at least about 30 psia.

51. The process of claim 33 wherein the adsorbent used in the pressure swing adsorption in step (1a) comprises a para-selective, non-acidic, medium pore molecular sieve, and wherein the pressure swing adsorption in step (1a) is operated at a temperature of at least about 350° F. and a pressure of at least about 30 psia.

52. The process of claim 40 wherein the adsorbent used in the pressure swing adsorption in step (1a) comprises a para-selective, non-acidic, medium pore molecular sieve, and wherein the pressure swing adsorption in step (1a) is operated at a temperature of at least about 350° F. and a pressure of at least about 30 psia.

53. The process of claim 44 wherein the adsorbent used in the pressure swing adsorption in step (1a) comprises a para-selective, non-acidic, medium pore molecular sieve, and wherein the pressure swing adsorption in step (1a) is operated at a temperature of at least about 350° F. and a pressure of at least about 30 psia.

54. The process of claim 47 wherein the adsorbent used in the pressure swing adsorption in step (1a) comprises a para-selective, non-acidic, medium pore molecular sieve, and wherein the pressure swing adsorption in step (1a) is operated at a temperature of at least about 350° F. and a pressure of at least about 30 psia.

55. A process for separating and recovering para-xylene from a gaseous mixture comprising $C_8$ aromatic hydrocarbons, the process comprising:
  (a) introducing a gaseous mixture comprising meta-xylene, ortho-xylene, and para-xylene into a pressure swing adsorption unit and subjecting the mixture to pressure swing adsorption under substantially isothermal conditions using an adsorbent comprising a para-selective adsorbent capable of selectively adsorbing para-xylene at a temperature and pressure at which at least 0.01 grams of para-xylene and ethylbenzene are adsorbed per gram of adsorbent to produce a meta-xylene and ortho-xylene-rich effluent stream comprising a mixture of ortho-xylene and meta-xylene, which contains no more than a total of about 20 mole percent of para-xylene based on total $C_8$ aromatics, and a para-xylene-rich effluent stream which contains no more than a total of about 50 mole percent of meta-xylene and ortho-xylene based on total $C_8$ aromatics;
  (b) sending at least a portion of the para-xylene-rich stream to a crystallization unit and crystallizing said para-xylene-rich stream to produce a para-xylene product stream and a para-xylene-lean mother liquor stream;
  (c) sending at least a portion of the meta-xylene and ortho-xylene-rich stream to an isomerization unit and isomerizing said stream to produce an isomerizate comprising an equilibrium mixture of xylenes;
  (d) recycling at least a portion of the isomerizate from step (c) to step (a);
  (e) sending at least a portion of the para-xylene-lean mother liquor stream from step (b) to an isomerization unit and isomerizing said stream to produce an isomerizate comprising an equilibrium mixture of xylenes; and
  (f) recycling at least a portion of the isomerizate from step (e) to step (a).

56. The process of claim 55 wherein the adsorbent used in the pressure swing adsorption in step (a) comprises a para-selective, non-acidic, medium pore molecular sieve, and wherein the pressure swing adsorption in step (a) is operated at a temperature of at least about 350° F. and a pressure of at least about 30 psia.

57. A process for separating and recovering para-xylene from a gaseous mixture comprising $C_8$ aromatic hydrocarbons, the process comprising:
  (a) introducing a gaseous mixture comprising meta-xylene, ortho-xylene, and para-xylene, into a pressure swing adsorption unit and subjecting the mixture to pressure swing adsorption under substantially isothermal conditions using an adsorbent comprising a para-selective adsorbent capable of selectively adsorbing para-xylene at a temperature and pressure at which at least 0.01 grams of para-xylene and ethylbenzene may be adsorbed per gram of adsorbent to produce a meta-xylene and ortho-xylene-rich effluent stream, and a para-xylene-rich effluent stream;
  (b) sending at least a portion of the para-xylene-rich stream to a crystallization unit and crystallizing said para-xylene-rich stream to produce a para-xylene product stream and a para-xylene-lean mother liquor stream;
  (c) sending at least a portion of the meta-xylene and ortho-xylene-rich stream to an isomerization unit and isomerizing said stream to produce an isomerizate comprising an equilibrium mixture of xylenes;
  (d) recycling at least a portion of the isomerizate from step (c) to step (a);
  (e) sending at least a portion of the para-xylene-lean mother liquor stream from step (b) to an isomerization unit and isomerizing said stream to produce an isomerizate comprising an equilibrium mixture of xylenes; and
  (f) recycling at least a portion of the isomerizate from step (e) to step (a).

58. The process of claim 57 wherein the adsorbent used in the pressure swing adsorption in step (a) comprises a para-selective, non-acidic, medium pore molecular sieve, and wherein the pressure swing adsorption in step (a) is operated at a temperature of at least about 350° F. and a pressure of at least about 30 psia.

59. A process for separating and recovering para-xylene from a gaseous mixture comprising $C_8$ aromatic hydrocarbons, the process comprising:
  (a) introducing a gaseous mixture comprising meta-xylene, ortho-xylene, para-xylene, and ethylbenzene into a pressure swing adsorption unit and subjecting the mixture to pressure swing adsorption under substantially isothermal conditions using an adsorbent comprising a para-selective adsorbent capable of selectively adsorbing para-xylene at a temperature and pressure at which at least 0.01 grams of para-xylene and ethylbenzene are adsorbed per gram of adsorbent to produce a meta-xylene and ortho-xylene-rich effluent stream, and a para-xylene-rich effluent stream comprising para-xylene and ethylbenzene;
  (b) sending at least a portion of the para-xylene-rich stream to a crystallization unit and crystallizing said para-xylene-rich stream to produce a para-xylene product stream and a para-xylene-lean mother liquor stream;
  (c) sending at least a portion of the meta-xylene and ortho-xylene-rich stream to an isomerization unit and isomerizing said stream to produce an isomerizate comprising an equilibrium mixture of xylenes;
  (d) recycling at least a portion of the isomerizate from step (c) to step (a);
  (e) sending at least a portion of the para-xylene-lean mother liquor stream from step (b) to an isomerization unit and isomerizing said stream to produce an isomerizate comprising an equilibrium mixture of xylenes; and
  (f) recycling at least a portion of the isomerizate from step (e) to step (a).

60. The process of claim 59 wherein the adsorbent used in the pressure swing adsorption in step (a) comprises a para-selective, non-acidic, medium pore molecular sieve, and wherein the pressure swing adsorption in step (a) is operated at a temperature of at least about 350° F. and a pressure of at least about 30 psia.

61. The process of claim 1 wherein the adsorbent contains about 5 to about 100 weight percent para-selective adsorbent.

62. The process of claim 1, wherein the crystallizing in step (b) comprises:
  contacting the para-xylene-rich stream with a para-xylene-containing liquid to produce a first slurry enriched in para-xylene relative to the para-xylene-rich stream;

separating crystalline para-xylene from the first slurry to produce a filtrate, a first mother liquor, and a first cake enriched in para-xylene relative to the first slurry;

contacting the first cake with a para-xylene-containing liquid to produce a second slurry enriched in para-xylene relative to the first slurry;

separating crystalline para-xylene from the second slurry to produce a filtrate, a second mother liquor, and the para-xylene-rich product stream; and, optionally combining the first and second mother liquors to produce the para-xylene-lean mother liquor stream.

63. The process of claim 62 wherein the first slurry is at a temperature of about −20° F. to about 20° F.;

the second slurry is at a temperature of about 35 ° F. to about 45° F.; and the para-xylene-containing liquid is liquid para-xylene.

64. The process of claim 62 wherein at least a portion of the filtrates is combined with one or more of the first and second slurries.

* * * * *